United States Patent
Shibayama et al.

(10) Patent No.: US 9,060,517 B2
(45) Date of Patent: Jun. 23, 2015

(54) NITROGENATED HETEROCYCLIC COMPOUND AND AGRICULTURAL OR HORTICULTURAL FUNGICIDE

(75) Inventors: Kotaro Shibayama, Odawara (JP); Raito Kuwahara, Odawara (JP); Motoaki Sato, Odawara (JP); Satoshi Nishimura, Odawara (JP); Yasuyuki Shiinoki, Odawara (JP); Masahiro Yokoyama, Odawara (JP); Juri Kitamura, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 14/116,695

(22) PCT Filed: May 17, 2012

(86) PCT No.: PCT/JP2012/062618
§ 371 (c)(1),
(2), (4) Date: Nov. 8, 2013

(87) PCT Pub. No.: WO2012/161071
PCT Pub. Date: Nov. 29, 2012

(65) Prior Publication Data
US 2014/0073792 A1    Mar. 13, 2014

(30) Foreign Application Priority Data

May 20, 2011 (JP) ................. 2011-113174
Jun. 28, 2011 (JP) ................. 2011-143478
Nov. 21, 2011 (JP) ................. 2011-254368
Dec. 15, 2011 (JP) ................. 2011-274141

(51) Int. Cl.
| | |
|---|---|
| A01N 43/60 | (2006.01) |
| C07D 401/12 | (2006.01) |
| C07D 241/52 | (2006.01) |
| C07D 471/04 | (2006.01) |
| A01N 43/90 | (2006.01) |
| A01N 43/42 | (2006.01) |

(52) U.S. Cl.
CPC .............. *A01N 43/60* (2013.01); *C07D 401/12* (2013.01); *C07D 241/52* (2013.01); *C07D 471/04* (2013.01); *A01N 43/90* (2013.01); *A01N 43/42* (2013.01)

(58) Field of Classification Search
CPC .............................. C07D 401/12; A01N 43/60
See application file for complete search history.

(56) References Cited

U.S. PATENT DOCUMENTS

| | | |
|---|---|---|
| 4,462,994 A | 7/1984 | Sakata et al. |
| 4,533,381 A | 8/1985 | Turner |
| 5,578,596 A | 11/1996 | Watanabe et al. |
| 8,772,200 B2 * | 7/2014 | Sato et al. .............. 504/247 |
| 2006/0211739 A1 | 9/2006 | Perez-Medrano et al. |
| 2008/0275242 A1 | 11/2008 | Ito et al. |

FOREIGN PATENT DOCUMENTS

| | | |
|---|---|---|
| EP | 0860433 A1 | 8/1998 |
| JP | 54-014977 | 2/1979 |
| JP | 58-092690 | 6/1983 |
| JP | 62-103051 | 5/1987 |
| JP | 05-032639 | 2/1993 |
| JP | 05-148235 | 6/1993 |
| JP | 07-285938 | 10/1995 |
| JP | 10-067746 | 3/1998 |
| JP | 2002-501945 | 1/2002 |
| JP | 2004-514663 | 5/2004 |
| JP | 2005-522428 | 7/2005 |
| JP | 2005-531518 | 10/2005 |

(Continued)

OTHER PUBLICATIONS

Notice of Opposition issued in CR Appln. No. 2013-0599, dated Jun. 9, 2014, 14 pages (with English translation).
International Search Report dated Jun. 19, 2012, issued in corresponding PCT Application No. PCT/JP2012/062618, 4 pages.
Office Action issued in TW Application No. 101117540, dated Oct. 22, 2013, 10 pages (with EN translation).
Lumma, Jr. et al., "Piperazinylquinoxalines With Central Serotoninmimetic Activity," Journal of Medicinal Chemistry, 1981, vol. 24, No. 1, pp. 93-101.

(Continued)

*Primary Examiner* — Noble Jarrell
*Assistant Examiner* — John S Kenyon
(74) *Attorney, Agent, or Firm* — Kenyon & Kenyon, LLP

(57) ABSTRACT

An agricultural or horticultural fungicide contains as an active ingredient thereof at least one compound selected from the group consisting of nitrogenated heterocyclic compounds represented by formula (I) (wherein, R represents a group represented by $CR^1R^2R^3$ or a cyano group, $R^1$ to $R^3$ represent hydrogen atoms, alkyl groups or hydroxyl groups, or the like, $X^1$ represents a halogeno group or the like, m represents an integer of 0 to 5, $X^2$ represents a halogeno group or the like, n represents an integer of 0 to 3, B represents a carbon atom or a nitrogen atom, D represents a 5- to 7-membered hydrocarbon ring, and $A^1$ to $A^4$ represent carbon atoms or nitrogen atoms, provided that $A^1$ to $A^4$ do not all represent carbon atoms when B represents a carbon atom) and salts thereof.

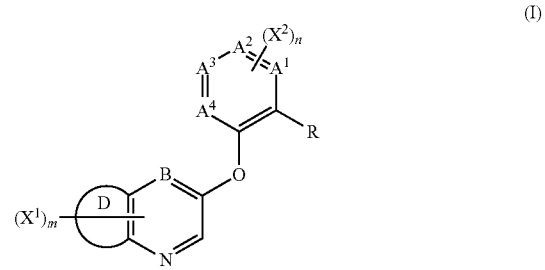

(I)

2 Claims, No Drawings

(56) References Cited

FOREIGN PATENT DOCUMENTS

| | | |
|---|---|---|
| JP | 2006-507336 | 3/2006 |
| JP | 2008-088139 | 4/2008 |
| JP | 2008-515971 | 5/2008 |
| JP | 2008-521872 | 6/2008 |
| JP | 2008-528590 | 7/2008 |
| JP | 2009-507024 | 2/2009 |
| JP | 2009-091320 | 4/2009 |
| WO | 92/17452 | 10/1992 |
| WO | 99/38845 A1 | 8/1999 |
| WO | 03/063861 | 8/2003 |
| WO | 03/064413 | 8/2003 |
| WO | 2005/070917 | 8/2005 |
| WO | 2006/044000 A1 | 4/2006 |
| WO | 2006/083612 | 8/2006 |
| WO | 2006/098308 A1 | 9/2006 |
| WO | 2007/011022 | 1/2007 |
| WO | 2007/088978 A1 | 8/2007 |
| WO | 2007/117180 | 10/2007 |
| WO | 2008/068270 | 6/2008 |
| WO | 2008/101682 A2 | 8/2008 |
| WO | 2009/021696 A1 | 2/2009 |
| WO | 2010/026771 | 3/2010 |
| WO | 2011/081174 | 7/2011 |

OTHER PUBLICATIONS

Erdogmus et al., "Synthesis, Photophysics and Photochemistry of Novel Tetra(quinoxalinyl)phthalocyaninato Zinc(II) Complexes," Journal of Photochemistry and Photobiology A: Chemistry, 2009, vol. 205, pp. 12-18.
Zhou et al., "3-Acrylamide-4-aryloxyindoles: Synthesis, Biological Evaluation and Metabolic Stability of potent and Selective EP3 Receptor Antagonists," Bioorganic & Medicinal Chemistry Letters, 2009, vol. 19, pp. 1528-1531.
International Search Report issued for PCT/JP2010/073683, dated Mar. 1, 2011, 10 pages (with English translation).
Yamamoto, Yasunori, et al., "Cyclic Triolborates: Air- and Water-Stable Ate Complexes of Organoboronic Acids", Angew. Chem. Int. Ed., 2008, vol. 47, pp. 928-931.
Calaway, Paul K., et al., "Utilization of Aryloxy Ketones in the Synthesis of Quinolines by the Pfitzinger Reaction", Jun. 1939, vol. 61, No. 6, pp. 1355-1358.
Royer, Rene, et al., "Sur la formation des aldehydes aromatiques par pyrodecomposition des aryloxyacetophenones", Helvetica Chimica Acta, 1959, vol. 42, No. 7, pp. 2364-2370.
Ruiz, Javier, et al., "Intramolecular cyclisation of functionalised heteroaryllithiums. Synthesis of novel indolizinone-based compounds", Tetrahedron, 2006, vol. 62, No. 26, pp. 6182-6189.
Chan, David C. M., et al., "Design, Synthesis, and Antifolate Activity of New Analogues of Piritrexim and Other Diamonopyrimidine Dihdryofolate Reductase Inhibitors with ω-Carboxyalkoxy or ω-Carboxy-1-alkynyl Substitution in the Side Chain", Journal of Medicinal Chemistry, 2005, vol. 48, No. 13, pp. 4420-4431.
EP Communication including Supplementary European Search Report from EP Appln. No. 10841029.1, May 8, 2013, 6 pages.
Burgos et al., "Significantly Improved Method for the Pd-Catalyzed Coupling of Phenols with Aryl Halides: Understanding Ligand Effects", Angewandte Chemie International Edition, vol. 45, Issue 26, pp. 4321-4326, Jun. 26, 2006.
Office Action issued in KR Appln. No. 10-2012-7016781, dated Oct. 29, 2013, 10 pages (with English translation).
Office Action issued in JP Appln. No. 2011-547711, dated Nov. 19, 2013, 10 pages (with English translation).
Nakashima et al., "Ring Contraction of 3-Hydroxyquinolines to Oxindoles with Hydrogen Peroxide in Acetic Acid," Chem. Pharm. Bull, Japan, 1969, 17(11), pp. 2293-2298.
Bhimani, "Studies on Compounds of Therapeutic Interest," Saurashtra University, doctorate thesis, India, 2004, 280 pages.
Notice of Allowance issued in the JP Application No. 2011-547711, dated Feb. 12, 2014, 8 pages.
Altman et al., "Cu-Catalyzed N- and O-Arylation of 2-, 3-, and 4-Hydroxypyridines and Hydroxyquinolines", Organic Letters, 2007, vol. 9, No. 4, pp. 643-646.
Toffano, M. "Applications of Tricoordinated Phosphorus Compounds in Homogeneous Catalysis", CA 153:555220, abstract only of Science of Synthesis, Volume Date 2008, 42, pp. 347-389, 2009, 1 page.
Notice of Allowance issued in U.S. Appl. No. 13/519,209, dated Apr. 29, 2014, 7 pages.
Office Action issued in JP Appln. No. 2013-516324, dated Nov. 11, 2014, 6 pages (with English translation).
EP Communication including Supplementary European Search Report from EP Appln. No. 12790304.5, dated Oct. 16, 2014, 6 pages.
Rizzo et al., "Silver(I)-Catalyzed Synthesis of Novel Quinoxaline Derivatives", Synthetic Communications, 2002, vol. 32, pp. 813-817.
Hassan et al., "1-Naphthyl Quinoxalin-2-yl Ether", Acta Cryst., 2009, E65, o731, 1 page.

* cited by examiner

NITROGENATED HETEROCYCLIC COMPOUND AND AGRICULTURAL OR HORTICULTURAL FUNGICIDE

TECHNICAL FIELD

The present invention relates to an agricultural or horticultural fungicide that demonstrates reliable effects and can be used safely, and to a nitrogenated heterocyclic compound that is useful as an active ingredient of an agricultural or horticultural fungicide.

The present application is a national stage application of International Application No. PCT/JP2012/062618, filed on May 17, 2012, which claims priority on Japanese Patent Application No. 2011-113174 filed in Japan on May 20, 2011, Japanese Patent Application No. 2011-143478 filed in Japan on Jun. 28, 2011, Japanese Patent Application No. 2011-254368 filed in Japan on Nov. 21, 2011, and Japanese Patent Application No. 2011-274141 filed in Japan on Dec. 15, 2011, the contents of which are incorporated herein by reference.

BACKGROUND ART

Numerous control agents are used against diseases of agricultural and horticultural crops. However, since the control effects of many control agents are inadequate, their use has been limited for reasons of the appearance of drug-resistant pathogens, chemical damage or contamination of plants, toxicity to humans, livestock and fish or significant effects on the environment, and none of these control agents have been sufficiently satisfactory. Consequently, there is a strong desire for the development of a drug that has few of these shortcomings.

In relation to the present invention, Patent Document 1 discloses 3-(dihydro(tetrahydro)isoquinolin-1-yl) quinoline compounds represented by the following formulas:

[Chemical Formula 1]

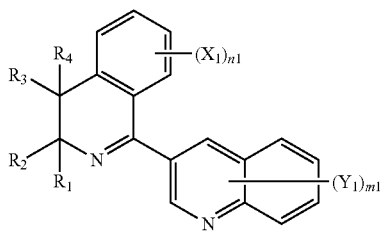

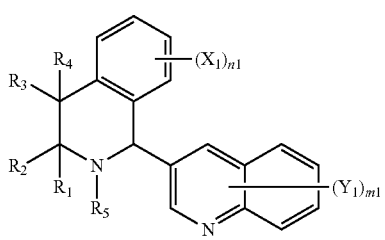

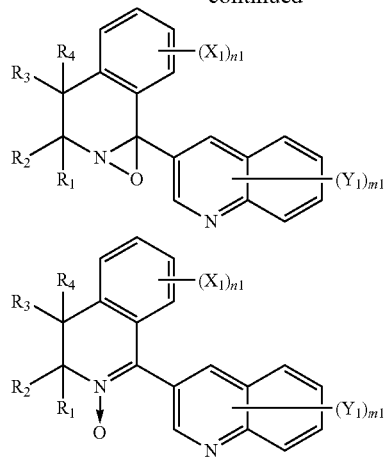

(wherein, $R_1$ and $R_2$ represent alkyl groups or the like, $R_3$ and $R_4$ represent hydrogen atoms, halogen atoms, or the like, $R_5$ represents a hydrogen atom, alkyl group, or the like, $X_1$ represents a halogen atom, an alkyl group, or the like, $Y_1$ represents a halogen atom, an alkyl group, or the like, n represents an integer of 0 to 4 and m represents an integer of 0 to 6), and an herbicide having these compounds as an active ingredient thereof.

In addition, Patent Document 2 discloses a 3-(isoquinolin-1-yl) quinoline compound represented by the following formula:

[Chemical Formula 2]

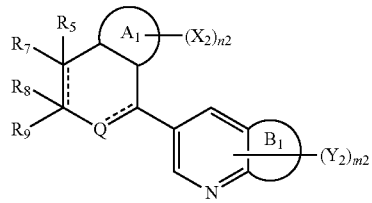

(wherein, ring $A_1$ and ring $B_1$ represent benzene rings or the like, $R_6$ to $R_9$ represent halogen atoms, alkyl groups, hydroxyl groups, alkoxy groups, or the like, Q represents N or N—$R_{10}$ (wherein $R_{10}$ represents a hydrogen atom, hydroxyl group, alkyl group, or the like), $X_2$ represents a halogen atom, alkyl group, or the like, $Y_2$ represents a halogen atom, alkyl group, or the like, $n_2$ represents an integer of 0 to 4, $m_2$ represents an integer of 0 to 6, and bonds containing dotted lines represent single bonds or double bonds), and an insecticide having that compound as an active ingredient thereof.

Moreover, Patent Document 3 discloses a phenoxypropionic acid ester derivative represented by the following formula:

[Chemical Formula 3]

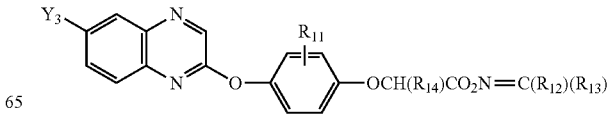

(wherein, Y₃ represents a halogen atom, R₁₁, R₁₂ and R₁₃ respectively and independently represent a lower alkyl group or lower alkoxy group, and R₁₄ represents a lower alkyl group), and a herbicide having that compound as an active ingredient thereof.

In addition, Patent Document 4 discloses a quinoxaline compound represented by the following formula:

[Chemical Formula 4]

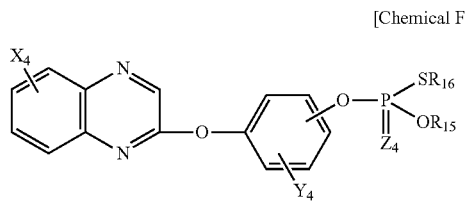

(wherein, X₄ represents a hydrogen atom, halogen atom, or the like, Y₄ represents a halogen atom or alkyl group, Z₄ represents an oxygen atom or sulfur atom, and R₁₅ and R₁₆ represent alkyl groups), and an insecticide having that compound as an active ingredient thereof.

In addition, Patent Document 5 discloses a pharmaceutical composition containing a compound represented by the following formula:

[Chemical Formula 5]

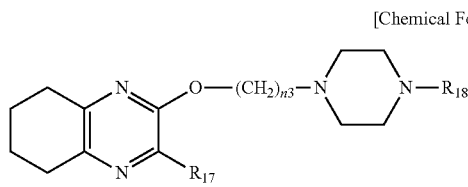

(wherein, R₁₇ represents a hydrogen atom, alkyl group, or the like, R₁₈ represents a pyridyl group, aryl group, or the like, and n₃ represents an integer of 2 to 5).

PRIOR ART DOCUMENTS

Patent Documents

Patent Document 1: International Publication No. WO 2005/070917
Patent Document 2: International Publication No. WO 2007/011022
Patent Document 3: Japanese Unexamined Patent Application, First Publication No. H05-148235
Patent Document 4: Japanese Unexamined Patent Application, First Publication No. S58-92690
Patent Document 5: U.S. Pat. No. 5,578,596

Non-Patent Documents

Non-Patent Document 1: Journal of Medicinal Chemistry, 1981, Vol. 24, (1), pp. 93-101

DISCLOSURE OF THE INVENTION

Problems to be Solved by the Invention

An object of the present invention is to provide an agricultural or horticultural fungicide that demonstrates reliable effects and can be used safely, and a nitrogenated heterocyclic compound, or a salt thereof, that is useful as an active ingredient of an agricultural or horticultural fungicide.

Means to Solve the Problems

The inventors of the present invention conducted extensive studies to solve the aforementioned problems. The results thereof led to the obtaining of a nitrogenated heterocyclic compound represented by formula (I) and salts thereof. The inventors of the present invention found that this nitrogenated heterocyclic compound demonstrates reliable effects and can be used safely as an active ingredient of an agricultural or horticultural fungicide. Further studies were then additionally conducted on the basis of these findings, thereby leading to completion of the present invention.

Namely, the present invention includes the aspects described below.

[1] A nitrogenated heterocyclic compound represented by formula (I), or a salt thereof:

[Chemical Formula 6]

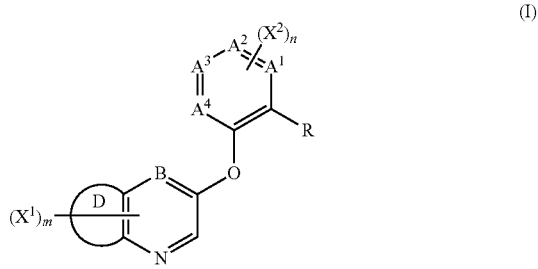

(wherein,

R represents a group represented by $CR^1R^2R^3$ or a cyano group;

$R^1$ to $R^3$ respectively and independently represent a hydrogen atom, an unsubstituted or substituted C1-8 alkyl group, an unsubstituted or substituted C2-8 alkenyl group, an unsubstituted or substituted C2-8 alkynyl group, an unsubstituted or substituted C3-8 cycloalkyl group, an unsubstituted or substituted C4-8 cycloalkenyl group, an unsubstituted or substituted C6-10 aryl group, an unsubstituted or substituted heterocyclic group, an unsubstituted or substituted C1-8 acyl group, an unsubstituted or substituted (1-imino)C1-8 alkyl group, an unsubstituted or substituted carboxyl group, an unsubstituted or substituted carbamoyl group, an unsubstituted or substituted hydroxyl group, an unsubstituted or substituted amino group, an unsubstituted or substituted mercapto group, a substituted sulfonyl group, a halogeno group, a cyano group or a nitro group, provided that, $R^1$ to $R^3$ are not all hydrogen atoms, $R^1$ to $R^3$ are not all unsubstituted C1-8 alkyl groups, in the case any one of $R^1$ to $R^3$ is a hydrogen atom, the remaining two are not unsubstituted C1-8 alkyl groups, in the case any one of $R^1$ to $R^3$ is an unsubstituted C1-8 alkyl group, the remaining two are not hydrogen atoms, and $R^1$ to $R^3$ may together form an unsubstituted or substituted 5- to 8-membered ring or may form a group represented by =O, a group represented by =$CR^aR^b$ (wherein, $R^a$ and $R^b$ respectively and independently represent a hydrogen atom or an unsubstituted or substituted C1-8 alkyl group), or a group represented by =N—R' (wherein, R' represents an unsubstituted or substituted hydroxyl group or an unsubstituted or substituted C1-8 alkyl group);

$X^1$ respectively and independently represents an unsubstituted or substituted C1-8 alkyl group, an unsubstituted or substituted C2-8 alkenyl group, an unsubstituted or substituted C2-8 alkynyl group, an unsubstituted or substituted hydroxyl group, a halogeno group, a cyano group or a nitro group;

m represents the number of $X^1$ and is an integer of 0 to 5;

$X^2$ respectively and independently represents an unsubstituted or substituted C1-8 alkyl group, an unsubstituted or substituted C2-8 alkenyl group, an unsubstituted or substituted C2-8 alkynyl group, an unsubstituted or substituted C3-8 cycloalkyl group, an unsubstituted or substituted C4-8 cycloalkenyl group, an unsubstituted or substituted C6-10 aryl group, an unsubstituted or substituted heterocyclic group, an unsubstituted or substituted C1-8 acyl group, an unsubstituted or substituted (1-imino) C1-8 alkyl group, an unsubstituted or substituted carboxyl group, an unsubstituted or substituted carbamoyl group, an unsubstituted or substituted hydroxyl group, an unsubstituted or substituted amino group, an unsubstituted or substituted mercapto group, a substituted sulfonyl group, a halogeno group, a cyano group or a nitro group;

n represents the number of $X^2$ and is an integer of 0 to 3; any one of $R^1$ to $R^3$ and any one of $X^2$ may together form an unsubstituted or substituted 5- to 8-member ring;

B represents a carbon atom or a nitrogen atom;

D represents an unsubstituted or $X^1$-substituted 5- to 7-membered hydrocarbon ring or an unsubstituted or $X^1$-substituted 5- to 7-membered heterocycle; and, $A^1, A^2, A^3$ and $A^4$ respectively and independently represent a carbon atom or a nitrogen atom, provided that in the case B is a carbon atom, $A^1$ to $A^4$ are not all carbon atoms.

[2] A nitrogenated heterocyclic compound, or salt thereof, wherein formula (I) described in [1] above is represented by formula (II):

[Chemical Formula 7]

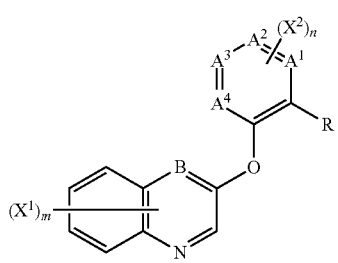

(II)

(wherein, R, $X^1$, m, $X^2$, n, $A^1, A^2, A^3, A^4$ and B respectively have the same meanings as those in formula (I) described in [1] above).

[3] A nitrogenated heterocyclic compound, or salt thereof, wherein formula (I) described in [1] above is represented by formula (III).

[Chemical Formula 8]

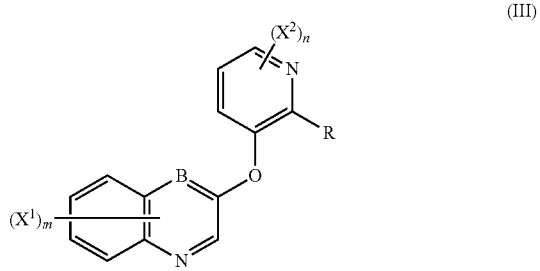

(III)

In the formula (III), R, $X^1$, m, $X^2$, n and B respectively have the same meanings as those in formula (I) described in [1] above.

[4] A nitrogenated heterocyclic compound, or salt thereof, wherein formula (I) described in [1] above is represented by formula (IV):

[Chemical Formula 9]

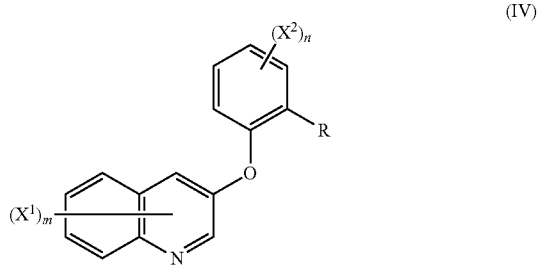

(IV)

(in the formula (IV), R, $X^1$, m, $X^2$ and n respectively have the same meanings as those in formula (I) described in [1] above).

[5] A nitrogenated heterocyclic compound, or salt thereof, wherein formula (I) described in [1] above is represented by formula (V):

[Chemical Formula 10]

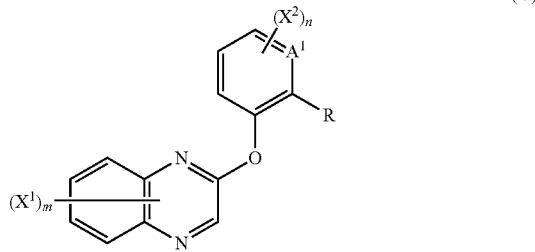

(V)

(in the formula (V), R, $X^1$, m, $X^2$, n and $A^1$ respectively have the same meanings as those in formula (I) described in [1] above).

[6] A nitrogenated heterocyclic compound, or salt thereof, wherein formula (I) described in [1] above is represented by formula (VI):

[Chemical Formula 11]

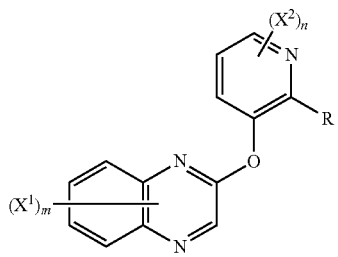

(VI)

(in the formula (VI), R, $X^1$, m, $X^2$ and n respectively have the same meanings as those in formula (I) described in [1] above).

[7] An agricultural or horticultural fungicide having as an active ingredient thereof at least one type of compound selected from the group consisting of the nitrogenated heterocyclic compounds and salts thereof, described in any of [1] to [6] above.

Effects of the Invention

The nitrogenated heterocyclic compound of the present invention is a novel compound that is useful as an active ingredient of an agricultural or horticultural fungicide.

The agricultural or horticultural fungicide of the present invention is a safe chemical agent that has reliable and excellent control effects, does not cause chemical damage to plants, and has little toxicity to humans, livestock or fish and has little effect on the environment.

EMBODIMENTS OF THE INVENTION

The following provides a detailed description of the present invention by dividing into sections on 1) the nitrogenated heterocyclic compound, and 2) the agricultural or horticultural fungicide.

1) Nitrogenated Heterocyclic Compound

The nitrogenated heterocyclic compound according to the present invention is a compound represented by formula (I) (to also be indicated as "Compound (I)").

[Chemical Formula 12]

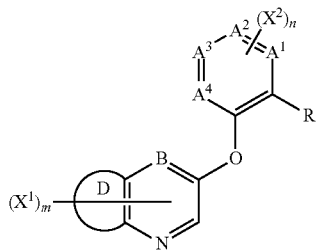

(I)

The nitrogenated heterocyclic compound according to the present invention include hydrates, various types of solvates, crystalline polymorphs, or the like. Moreover, the nitrogenated heterocyclic compound according to the present invention includes stereoisomers based on an asymmetric carbon atom or double bond and the like as well as mixtures thereof.

First, an explanation is provided of the meanings of "unsubstituted" and "substituted" in formula (I).

The term "unsubstituted" refers to the group being the only group serving as a mother nucleus. When there is no description of being "substituted" and a description is only provided for the name of the group serving as a mother nucleus, this refers to "unsubstituted" unless specifically indicated otherwise.

On the other hand, the term "substituted" refers to any hydrogen atom of a group serving as a mother nucleus being substituted with a group having a structure that is the same as or different from the mother nucleus. Thus, a "substituent" is another group bound to a group serving as the mother nucleus. There may be one substituent or two or more substituents. Two or more substituents may be the same or different.

The term "C1-6", for example, indicates that the number of carbon atoms of the group serving as the mother nucleus is 1 to 6. This number of carbon atoms does not include the number of carbon atoms present in substituents. For example, a butyl group having an ethoxy group as a substituent thereof is classified as a C2 alkoxy C4 alkyl group.

There are no particular limitations on "substituents" provided they are chemically allowed and have the effect of the present invention.

Examples of groups able to be "substituents" include halogen atoms such as a fluorine atom, chlorine atom, bromine atom or iodine atom; C1-6 alkyl groups such as a methyl group, ethyl group, n-propyl group, i-propyl group, n-butyl group, s-butyl group, i-butyl group, t-butyl group, n-pentyl group, or n-hexyl group; C3-6 cycloalkyl groups such as a cyclopropyl group, cyclobutyl group, cyclopentyl group or cyclohexyl group; C2-6 alkenyl groups such as a vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group or 5-hexenyl group; C3-6 cycloalkenyl groups such as a 2-cyclopropenyl group, 2-cyclopentenyl group or 3-cyclohexenyl group; C2-6 alkynyl groups such as an ethynyl group, 1-propynyl group, 2-propynyl group, 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group or 1,1-dimethyl-2-butynyl group;

C1-6 alkoxy groups such as a methoxy group, ethoxy group, n-propoxy group, i-propoxy group, n-butoxy group, s-butoxy group, i-butoxy group or t-butoxy group; C2-6 alkenyloxy groups such as a vinyloxy group, allyloxy group, propenyloxy group or butenyloxy group; C2-6 alkynyloxy groups such as an ethynyloxy group or propargyloxy group; C6-10 aryl groups such as a phenyl group or naphthyl group; C6-10 aryloxy groups such as a phenoxy group or 1-naphthoxy group; C7-11 aralkyl groups such as a benzyl group or phenethyl group; C7-11 aralkyloxy groups such as a benzyloxy group or phenethyloxy group; C1-7 acyl groups such as a formyl group, acetyl group, propionyl group, benzoyl group or cyclohexylcarbonyl group; C1-7 acyloxy groups such as a formyloxy group, acetyloxy group, propionyloxy group, benzoyloxy group or cyclohexylcarbonyloxy group; C1-6 alkoxycarbonyl groups such as a methoxycarbonyl group, ethoxycarbonyl group, n-propoxycarbonyl group, i-propoxycarbonyl group, n-butoxycarbonyl group or t-butoxycarbonyl group; carboxyl group;

hydroxyl group; oxo group; C1-6 haloalkyl groups such as a chloromethyl group, chloroethyl group, trifluoromethyl group, 1,2-dichloro-n-propyl group, 1-fluoro-n-butyl group or perfluoro-n-pentyl group; C2-6 haloalkenyl groups such as a 2-chloro-1-propenyl group or 2-fluoro-1-butenyl group; C2-6 haloalkynyl groups such as a 4,4-dichloro-1-butynyl group, 4-fluoro-1-pentynyl group or 5-bromo-2-pentynyl group; C1-6 haloalkoxy groups such as a 2-chloro-n-propoxy group or 2,3-dichlorobutoxy group; C2-6 haloalkenyloxy groups such as a 2-chloropropenyloxy group or 3-bromobutenyloxy group; C6-10 haloaryl groups such as a 4-chlorophenyl group, 4-fluorophenyl group or 2,4-dichlorophenyl group; C6-10 haloaryloxy groups such as a 4-fluorophenyloxy group or 4-chloro-1-napthoxy group; C1-7 haloacyl groups such as a chloroacetyl group, trifluoroacetyl group, trichloroacetyl group or 4-chlorobenzoyl group;

cyano group; isocyano group; nitro group; isocyanato group; cyanato group; azide group; amino group; C1-6 alkylamino groups such as a methylamino group, dimethylamino group or diethylamino group; C6-10 arylamino groups such as an anilino group or naphthylamino group; C7-11 aralkylamino groups such as a benzylamino group or phenylethylamino group; C1-7 acylamino groups such as a formylamino group, acetylamino group, propanoylamino group, butyrylamino group, i-propylcarbonylamino group or benzoylamino group; C1-6 alkoxycarbonylamino groups such as a methoxycarbonylamino group, ethoxycarbonylamino group, n-propoxycarbonylamino group or i-propoxycarbonylamino group; carbamoyl group; substituted carbamoyl groups such as a dimethylcarbamoyl group, phenylcarbamoyl group or N-phenyl-N-methylcarbamoyl group; imino C1-6 alkyl groups such as an iminomethyl group, (1-imino)ethyl group or (1-imino)-n-propyl group; hydroxyimino C1-6 alkyl groups such as a hydroxyiminomethyl group, (1-hydroxyimino)ethyl group or (1-hydroxyimino)propyl group; C1-6 alkoxyimino C1-6 alkyl groups such as a methoxyiminomethyl group or (1-methoxyimino)ethyl group;

mercapto group; isothiocyanato group; thiocyanato group; C1-6 alkylthio groups such as a methylthio group, ethylthio group, n-propylthio group, i-propylthio group, n-butylthio group, i-butylthio group, s-butylthio group or t-butylthio group; C2-6 alkenylthio groups such as a vinylthio group or allylthio group; C2-6 alkynylthio groups such as an ethynylthio group or propargylthio group; C6-10 arylthio groups such as a phenylthio group or napthylthio group; heteroarylthio groups such as a thiazolylthio group or pyridylthio group; C7-11 aralkylthio groups such as a benzylthio group or phenethylthio group; (C1-6 alkylthio)carbonyl groups such as a (methylthio)carbonyl group, (ethylthio)carbonyl group, (n-propylthio)carbonyl group, (i-propylthio)carbonyl group, (n-butylthio)carbonyl group, (i-butylthio)carbonyl group, (s-butylthio)carbonyl group or (t-butylthio)carbonyl group;

C1-6 alkylsulfinyl groups such as a methylsulfinyl group, ethylsulfinyl group or t-butylsulfinyl group; C2-6 alkenylsulfinyl groups such as an allylsulfinyl group; C2-6 alkynylsulfinyl groups such as a propargylsulfinyl group; C6-10 arylsulfinyl groups such as a phenylsulfinyl group; heteroarylsulfinyl groups such as a thiazolylsulfinyl group or pyridylsulfinyl group; C7-11 aralkylsulfinyl groups such as a benzylsulfinyl group or phenethylsulfinyl group; C1-6 alkylsulfonyl groups such as a methylsulfonyl group, ethylsulfonyl group or t-butylsulfonyl group; C2-6 alkenylsulfonyl groups such as an allylsulfonyl group; C2-6 alkynylsulfonyl groups such as a propargylsulfonyl group; C6-10 arylsulfonyl groups such as a phenylsulfonyl group; heteroarylsulfonyl groups such as a thiazolylsulfonyl group or pyridylsulfonyl group; C7-11 aralkylsulfonyl groups such as a benzylsulfonyl group or phenethylsulfonyl group;

5-membered heteroaryl groups such as a pyrrolyl group, furyl group, thienyl group, imidazolyl group, pyrazolyl group, oxazolyl group, isoxazolyl group, triazolyl group, isothiazolyl group, triazolyl group, oxadiazolyl group, thiadiazolyl group or tetrazolyl group; 6-membered heteroaryl groups such as pyridyl group, pyrazinyl group, pyrimidinyl group, pyridazinyl group or triazinyl group; saturated heterocyclic groups such as aziridinyl group, epoxy group, pyrrolidinyl group, tetrahydrofuranyl group, piperidyl group, piperazinyl group or morpholinyl group; tri-C1-6 alkylsilyl groups such as a trimethylsilyl group, triethylsilyl group or t-butyldimethylsilyl group; and, a triphenylsilyl group.

In addition, these "substituents" may also have other "substituents" therein. For example, a substituent may be that having an ethoxy group as another substituent in a substituent in the form of a butyl group, or in other words, an ethoxybutyl group.

[R]

R represents a group represented by $CR^1R^2R^3$ or a cyano group.

$R^1$ to $R^3$ respectively and independently represent a hydrogen atom, an unsubstituted or substituted C1-8 alkyl group, an unsubstituted or substituted C2-8 alkenyl group, an unsubstituted or substituted C2-8 alkynyl group, an unsubstituted or substituted C3-8 cycloalkyl group, an unsubstituted or substituted C4-8 cycloalkenyl group, an unsubstituted or substituted C6-10 aryl group, an unsubstituted or substituted heterocyclic group, an unsubstituted or substituted C1-8 acyl group, an unsubstituted or substituted (1-imino)C1-8 alkyl group, an unsubstituted or substituted carboxyl group, an unsubstituted or substituted carbamoyl group, an unsubstituted or substituted hydroxyl group, an unsubstituted or substituted amino group, an unsubstituted or substituted mercapto group, a substituted sulfonyl group, a halogeno group, a cyano group or a nitro group, provided that, $R^1$ to $R^3$ are not all hydrogen atoms, $R^1$ to $R^3$ are not all unsubstituted C1-8 alkyl groups, in the case any one of $R^1$ to $R^3$ is a hydrogen atom, the remaining two are not unsubstituted C1-8 alkyl groups, and in the case any one of $R^1$ to $R^3$ is an unsubstituted C1-8 alkyl group, the remaining two are not hydrogen atoms.

A "C1-8 alkyl group" is a saturated hydrocarbon group composed of 1 to 8 carbon atoms. The C1-8 alkyl group may be linear or branched. Examples of C1-8 alkyl groups include a methyl group, ethyl group, n-propyl group, n-butyl group, n-pentyl group, n-hexyl group, n-heptyl group, n-octyl group, i-propyl group, i-butyl group, s-butyl group, t-butyl group, i-pentyl group, neopentyl group, 2-methylbutyl group, 2,2-dimethylpropyl group and i-hexyl group. Among these, C1-6 alkyl groups are preferable.

Examples of "substituted C1-8 alkyl groups" include:

cycloalkylalkyl groups such as a cyclopropylmethyl group, 2-cyclopropylethyl group, cyclopentylmethyl group or 2-cyclohexylethyl group, and preferably C3-6 cycloalkyl C1-8 alkyl groups;

cycloalkenylalkyl groups such as a cyclopentenylmethyl group, 3-cyclopentenylmethyl group, 3-cyclohexenylmethyl group or 2-(3-cyclohexenyl)ethyl group, and preferably C4-6 cycloalkenyl C1-6 alkyl groups;

haloalkyl groups such as a fluoromethyl group, chloromethyl group, bromomethyl group, difluoromethyl group, dichloromethyl group, dibromomethyl group, trifluoromethyl group, trichloromethyl group, tribromomethyl group, 2,2,2-trifluoroethyl group, 2,2,2-trichloroethyl group, pentafluoroethyl group, 4-fluorobutyl group, 4-chlorobutyl group, 3,3,3-trifluoropropyl group, 2,2,2-trifluoro-1-trifluoromethylethyl group, perfluorohexyl group, perchlorohexyl group, perfluorooctyl group, perchlorooctyl group, 2,4,6-trichlorohexyl group, perfluorodecyl group or 2,2,4,4,6,6-hexafluorooctyl group, and preferably C1-6 haloalkyl groups;

arylalkyl(aralkyl) groups such as a benzyl group, phenethyl group, 3-phenylpropyl group, 1-naphthylmethyl group or 2-naphthylmethyl group, and preferably C6-10 aryl C1-6 alkyl groups;

heteroarylalkyl groups such as a 2-pyridylmethyl group, 3-pyridylmethyl group, 4-pyridylmethyl group, 2-(2-pyridyl)ethyl group, 2-(3-pyridyl)ethyl group, 2-(4-pyridyl)ethyl group, 3-(2-pyridyl)propyl group, 3-(3-pyridyl)propyl group, 3-(4-pyridyl)propyl group, 2-pyridinylmethyl group, 3-pyrazinylmethyl group, 2-(2-pyrazinyl)ethyl group, 2-(3-pyrazinyl)ethyl group, 3-(2-pyrazinyl)propyl group, 3-(3-pyrazinyl)propyl group, 2-pyrimidylmethyl group, 4-pyrimidylmethyl group, 2-(2-pyrimidyl)ethyl group, 2-(4-pyrimidyl)ethyl group, 3-(2-pyrimidyl)propyl group, 3-(4-pyrimidyl)propyl group, 2-furylmethyl group, 3-furylmethyl group, 2-(2-furyl)ethyl group, 2-(3-furyl)ethyl group, 3-(2-furyl)propyl group or 3-(3-furyl)propyl group, and preferably 5- to 6-membered heteroaryl C1-6 alkyl groups;

hydroxyalkyl groups such as a hydroxymethyl group, 1-hydroxyethyl group, 2-hydroxyethyl group, 1-hydroxypropyl group, 3-hydroxypropyl group, 1-hydroxy-1-methylethyl group, 2-hydroxy-1,1-dimethylethyl group, 2-hydroxy-1,1-dimethylpropyl group or 2-hydroxy-2-methylpropyl group, and preferably hydroxyl C1-6 alkyl groups;

alkoxyalkyl groups such as a methoxymethyl group, ethoxymethyl group, 2-methoxyethyl group, 2-ethoxyethyl group, methoxy-n-propyl group, n-propoxymethyl group, i-propoxyethyl group, s-butoxymethyl group, t-butoxyethyl group, 2,2-dimethoxyethyl group or 2,2-dimethoxy-1,1-dimethylethyl group, and preferably C1-6 alkoxy C1-6 alkyl groups;

acyloxyalkyl groups such as a formyloxymethyl group, acetoxymethyl group, 2-acetoxyethyl group, propionyloxymethyl group or propionyloxyethyl group, and preferably C1-7 acyloxy C1-6 alkyl groups;

trialkylsilyloxyalkyl groups such as a trimethylsilyloxymethyl group or t-butyldimethylsilyloxymethyl group, and preferably tri-C1-6 alkylsilyloxy C1-6 alkyl groups;

arylsulfonyloxyalkyl groups such as a tosyloxymethyl group or 2-tosyloxy-1,1-dimethylethyl group, and preferably C1-6 alkyl-substituted C6-10 arylsulfonyloxy C1-6 alkyl groups;

cyanoalkyl groups such as a cyanomethyl group, 2-cyanoethyl group or 1-cyano-1-methylethyl group, and preferably cyano C1-6 alkyl groups;

acylalkyl groups such as a formylmethyl group, 2-formylethyl group, 3-formylpropyl group, 1-formyl-1-methylethyl group, 2-formyl-1,1-dimethylethyl group, acetylmethyl group, 2-acetylethyl group, 3-acetylpropyl group, 1-acetyl-1-methylethyl group or 2-acetyl-1,1-dimethylethyl group, and preferably C1-7 acyl C1-6 alkyl groups;

2-hydroxyiminoalkyl groups such as a 2-hydroxyiminoethyl group, 2-hydroxyimino-1-methylethyl group, 2-hydroxy-1,1-dimethylethyl group or 2-hydroxyiminopropyl group, and preferably 2-hydroxyimino C2-6 alkyl groups;

acylalkyl groups such as an acetylmethyl group, 2-acetylethyl group, 3-acetylpropyl group, 1-acetyl-1-methylethyl group or 2-acetyl-1,1-dimethylethyl group, and preferably C1-7 acyl C1-6 alkyl groups;

carboxyalkyl groups such as a carboxymethyl group, 2-carboxyethyl group, 3-carboxypropyl group, 1-carboxy-1-methylethyl group or 2-carboxy-1,1-dimethylethyl group, and preferably carboxy C1-6 alkyl groups;

alkoxycarbonylalkyl groups such as a methoxycarbonylmethyl group, 2-methoxycarbonylethyl group, 3-methoxycarbonylpropyl group, 1-methoxycarbonyl-1-methylethyl group or 2-methoxycarbonyl-1,1-dimethylethyl group, and preferably C1-6 alkoxycarbonyl C1-6 alkyl groups; and, azidoalkyl groups such as an azidomethyl group, 2-azidoethyl group or 1-azido-1-methylethyl group, and preferably azido C1-6 alkyl groups.

A "C2-8 alkenyl group" is an unsaturated hydrocarbon group composed of 2 to 8 carbon atoms having at least one carbon-carbon double bond. The C2-8 alkenyl group may be linear or branched. Examples of C2-8 alkenyl groups include a vinyl group, 1-propenyl group, isopropenyl group, allyl group, 1-butenyl group, 2-butenyl group, 3-butenyl group, 1-pentenyl group, 2-pentenyl group, 3-pentenyl group, 4-pentenyl group, 1-hexenyl group, 2-hexenyl group, 3-hexenyl group, 4-hexenyl group, 5-hexenyl group, 1-heptenyl group, 6-heptenyl group, 1-octenyl group, 7-octenyl group, 1-methylallyl group, 2-methylallyl group, 1-methyl-2-butenyl group and 2-methyl-2-butenyl group. Among these, C2-6 alkenyl groups are preferable.

Examples of "substituted C2-8 alkenyl groups" include haloalkenyl groups such as a 3-chloro-2-propenyl group, 4-chloro-2-butenyl group, 4,4-dichloro-3-butenyl group, 4,4-difluoro-3-butenyl group, 3,3-dichloro-2-propenyl group, 2,3-dichloro-2-propenyl group, 3,3-difluoro-2-propenyl group or 2,4,6-trichloro-2-hexenyl group, and preferably C2-6 haloalkenyl groups; and, hydroxyalkenyl groups such as a 3-hydroxy-1-propenyl group, 4-hydroxy-1-butenyl group, 1-hydroxyallyl group or 1-hydroxy-2-methylallyl group, and preferably hydroxyl C2-6 alkenyl groups.

A "C2-8 alkynyl group" is an unsaturated hydrocarbon group composed of 2-8 carbon atoms having at least one carbon-carbon triple bond. The C2-8 alkynyl group may be linear or branched. Examples of C2-8 alkynyl groups include an ethynyl group, 1-propynyl group, propargyl group, 1-butynyl group, 2-butynyl group, 3-butynyl group, 1-pentynyl group, 2-pentynyl group, 3-pentynyl group, 4-pentynyl group, 1-hexynyl group, 1-methyl-2-propynyl group, 2-methyl-3-butynyl group, 1-methyl-2-butynyl group, 2-methyl-3-pentynyl group and 1,1-dimethyl-2-butynyl group. Among these, C2-6 alkynyl groups are preferable.

Examples of "substituted C2-8 alkynyl groups" include haloalkynyl groups such as a 3-chloro-1-propynyl group, 3-chloro-1-butynyl group, 3-bromo-1-butynyl group, 3-bromo-2-propynyl group, 3-iodo-2-propynyl group, 3-bromo-1-hexynyl group, 4,4,6,6-tetrafluoro-1-dodecynyl group, 5,5-dichloro-2-methyl-3-pentynyl group or 4-chloro-1,1-dimethyl-2-butynyl group, and preferably C2-6 haloalkynyl groups.

A "C3-8 cycloalkyl group" is an alkyl group composed of 3 to 8 carbon atoms having a cyclic moiety. Examples of C3-8 cycloalkyl groups include a cyclopropyl group, cyclobutyl group, cyclopentyl group, cyclohexyl group, cycloheptyl group and cyclooctyl group. Among these, C3-6 cycloalkyl groups are preferable.

Examples of "C3-8 cycloalkyl groups" include alkyl-substituted cycloalkyl groups such as a 2,3,3-trimethylcyclobutyl group, 4,4,6,6-tetramethylcyclohexyl group or 1,3-dibutylcyclohexyl group, and preferably C3-6 cycloalkyl groups substituted with 1 to 3 C1-6 alkyl groups.

A "C4-8 cycloalkenyl group" is an alkenyl group composed of 4 to 8 carbon atoms having a cyclic moiety. Examples of C4-8 cycloalkenyl groups include a 1-cyclobutenyl group, 1-cyclopentenyl group, 3-cyclopentenyl group, 1-cyclohexenyl group, 3-cyclohexenyl group, 3-cycloheptenyl group and 4-cyclooctenyl group.

Examples of "substituted C4-8 cycloalkenyl groups" include alkyl-substituted cycloalkenyl groups such as a 2-methyl-3-cyclohexenyl group or 3,4-dimethyl-3-cyclohexenyl group, and preferably C4-6 cycloalkenyl groups substituted with 1 to 3 C1-6 alkyl groups.

A "C6-10 aryl group" is a monocyclic or polycyclic aryl group having 6 to 10 carbon atoms. Furthermore, as long as at least one of the rings of a polycyclic aryl group is an aromatic ring, the remaining rings may be saturated alicyclic rings, unsaturated alicyclic rings, or aromatic rings. Examples of C6-10 aryl groups include a phenyl group, naphthyl group, azulenyl group, indenyl group, indanyl group and tetralinyl group. Among these, a phenyl group is preferable.

Examples of "substituted C6-10 aryl groups" include alkyl-substituted aryl groups, halogeno-substituted aryl groups, and alkoxy-substituted aryl groups, such as a 2-chlorophenyl group, 3,5-dichlorophenyl group, 4-fluorophenyl group, 3,5-difluorophenyl group, 4-trifluoromethylphenyl group or 2-methoxy-1-napthyl group, and preferably C1-6 alkyl-substituted C6-10 aryl groups, halogeno-substituted C6-10 aryl groups, and C1-6 alkoxy-substituted aryl groups.

A "heterocyclic group" is a group that contains as constituent elements of the ring 1 to 4 heteroatoms selected from the group consisting of a nitrogen atom, oxygen atom and sulfur atom. The heterocyclic group may be monocyclic or polycyclic.

Examples of heterocyclic groups include 5-membered heteroaryl groups, 6-membered heteroaryl groups, condensed heteroaryl groups, saturated heterocyclic groups and partially unsaturated heterocyclic groups.

Examples of 5-membered heteroaryl groups include pyrrolyl groups such as a pyrrol-1-yl group, pyrrol-2-yl group or pyrrol-3-yl group; furyl groups such as a furan-2-yl group or furan-3-yl group; thienyl groups such as a thiophen-2-yl group or thiophen-3-yl group; imidazolyl groups such as a imidazol-1-yl group, imidazol-2-yl group, imidazol-4-yl group or imidazol-5-yl group; pyrazolyl groups such as a pyrazol-1-yl group, pyrazol-3-yl group, pyrazol-4-yl group or pyrazol-5-yl group; oxazolyl groups such as an oxazol-2-yl group, oxazol-4-yl group or oxazol-5-yl group; isoxazolyl groups such as an isoxazol-3-yl group, isoxazol-4-yl group or isoxazol-5-yl group; triazolyl groups such as a thiazol-2-yl group, thiazol-4-yl group or thiazol-5-yl group; isothiazolyl groups such as an isothiazol-3-yl group, isothiazol-4-yl group or isothiazol-5-yl group; triazolyl groups such as a 1,2,3-triazol-1-yl group, 1,2,3-triazol-4-yl group, 1,2,3-triazol-5-yl group, 1,2,4-triazol-1-yl group, 1,2,4-triazol-3-yl group or 1,2,4-triazol-5-yl group; oxadiazolyl groups such as a 1,2,4-oxadiazol-3-yl group, 1,2,4-oxadiazol-5-yl group or 1,3,4-oxadiazol-2-yl group; thiadiazolyl groups such as a 1,2,4-thiadiazol-3-yl group, 1,2,4-thiadiazol-5-yl group or 1,3,4-thiadiazol-2-yl group; and, tetrazolyl groups such as a tetrazol-1-yl group or tetrazol-2-yl group.

Examples of 6-membered heteroaryl groups include pyridyl groups such as a pyridin-2-yl group, pyridin-3-yl group or pyridin-4-yl group; pyrazinyl groups such as a pyrazin-2-yl group or pyrazin-3-yl group; pyrimidinyl groups such as a pyrimidin-2-yl group, pyrimidin-4-yl group or pyrimidin-5-yl group; and, pyridazinyl groups such as a pyridazin-3-yl group or pyridazin-4-yl group.

Examples of condensed heteroaryl groups include an indol-1-yl group, indol-2-yl group, indol-3-yl group, indol-4-yl group, indol-5-yl group, indol-6-yl group, indol-7-yl group, benzofuran-2-yl group, benzofuran-3-yl group, benzofuran-4-yl group, benzofuran-5-yl group, benzofuran-6-yl group, benzofuran-7-yl group, benzothiophen-2-yl group, benzothiophen-3-yl group, benzothiophen-4-yl group, benzothiophen-5-yl group, benzothiophen-6-yl group, benzothiophen-7-yl group, benzoimidazol-1-yl group, benzoimidazol-2-yl group, benzoimidazol-4-yl group, benzoimidazol-5-yl group, benzoxazol-2-yl group, benzoxazol-4-yl group, benzoxazol-5-yl group, benzothiazol-2-yl group, benzothiazol-4-yl group, benzothiazol-5-yl group, quinolin-2-yl group, quinolin-3-yl group, quinolin-4-yl group, quinolin-5-yl group, quinolin-6-yl group, quinolin-7-yl group, quinolin-8-yl group, and the like.

Examples of other heterocyclic groups include 3-membered saturated heterocyclic groups such as an aziridin-1-yl group, aziridin-2-yl group or oxiranyl group; 5-membered saturated heterocyclic groups such as a pyrrolidin-1-yl group, pyrrolidin-2-yl group, pyrrolidin-3-yl group, tetrahydrofuran-2-yl group, tetrahydrofuran-3-yl group or [1,3]dioxiran-2-yl group; 6-membered saturated heterocyclic groups such as a piperidin-1-yl group, piperidin-2-yl group, piperidin-3-yl group, piperidin-4-yl group, piperazin-1-yl group, piperazin-2-yl group, morpholin-2-yl group, morpholin-3-yl group or morpholin-4-yl group; and, a 1,3-benzodioxole-4-yl group, 1,3-benzodioxole-5-yl group, 1,4-benzodioxole-5-yl group, 1,4-benzodioxane-6-yl group, 3,4-dihydro-2H-1,5-benzodioxepin-6-yl group, 3,4-dihydro-2H-1,5-benzodioxepin-7-yl group, 2,3-dihydrobenzofuran-4-yl group, 2,3-dihydrobenzofuran-5-yl group, 2,3-dihydrobenzofuran-6-yl group and 2,3-dihydrobenzofuran-7-yl group.

Examples of "substituted heterocyclic groups" include a 4-chloro-2-pyridinyl group, 3-chloro-2-pyrazinyl group, 4-methyl-2-pyridinyl group, 5-trifluoromethyl-2-pyrimidinyl group and 3-methyl-2-quinolyl group.

A "C1-8 acyl group" is a group in which a hydrogen atom, C1-6 alkyl group, C2-6 alkenyl group, C2-6 alkynyl group, C6-7 aryl group or 5- to 7-membered heterocyclic group is bonded to a carbonyl group.

Examples of C1-8 acyl groups include a formyl group; alkylcarbonyl groups such as an acetyl group, propionyl group, n-propylcarbonyl group, n-butylcarbonyl group, pentanoyl group, valeryl group, octanoyl group, i-propylcarbonyl group, i-butylcarbonyl group, pivaloyl group or isovaleryl group, and preferably C1-6 alkylcarbonyl groups; alkenylcarbonyl groups such as an acryloyl group or methacryloyl group, and preferably C2-6 alkenylcarbonyl groups; alkynylcarbonyl groups such as a propionoyl group, and preferably C2-6 alkynylcarbonyl groups; C6-C7 arylcarbonyl groups such as a benzoyl group; and heterocyclic carbonyl groups such as a 2-pyridylcarbonyl group or thienylcarbonyl group.

Examples of "substituted C1-8 acyl groups" include haloacyl groups such as a monofluoroacetyl group, monochloroacetyl group, monobromoacetyl group, difluoroacetyl group, dichloroacetyl group, dibromoacetyl group, trifluoroacetyl group, trichloroacetyl group, tribromoacetyl group, 3,3,3-trifluoropropionyl group, 3,3,3-trichloropropionyl group or 2,2,3,3,3-pentafluoropropionyl group, and preferably C1-8 haloacyl groups.

A "(1-imino)C1-8 alkyl group" is an iminomethyl group or a group in which a C1-7 alkyl group is bonded to an iminomethyl group. Examples of (1-imino)C1-8 alkyl groups include an iminomethyl group, (1-imino)ethyl group, (1-imino)propyl group, (1-imino)butyl group, (1-imino)pentyl group, (1-imino)hexyl group and (1-imino)heptyl group. Among these, (1-imino)C1-6 alkyl groups are preferable.

Examples of "substituted (1-imino)C1-8 alkyl groups" include (1-hydroxyimino)alkyl groups such as a hydroxyiminomethyl group, (1-hydroxyimino)ethyl group, (1-hydroxyimino)propyl group or (1-hydroxyimino)butyl group, and preferably (1-hydroxyimino)C1-6 alkyl groups; and (1-alkoxyimino) alkyl groups such as a methoxyiminomethyl group, (1-ethoxyimino)methyl group, (1-methoxyimino) ethyl group, (1-t-butoxyimino)ethyl group or (1-ethoxyimino)ethyl group, and preferably (1-(C1-6 alkoxy)imino) C1-6 alkyl groups.

A "substituted carboxyl group" is a group in which a C1-6 alkyl group, C2-6 alkenyl group, C2-6 alkynyl group, C6-10 aryl group, C6-10 aryl C1-6 alkyl group or 5- to 6-membered heterocyclic group is bonded to a carbonyl group.

Examples of "substituted carboxyl groups" include alkoxycarbonyl groups such as a methoxycarbonyl group, ethoxycarbonyl group, n-propoxycarbonyl group, i-propoxycarbonyl group, n-butoxycarbonyl group, i-butoxycarbonyl group, t-butoxycarbonyl group, n-pentyloxycarbonyl group or n-hexyloxycarbonyl group, and preferably C1-6 alkoxycarbonyl groups;

alkenyloxycarbonyl groups such as a vinyloxycarbonyl group or allyloxycarbonyl group, and preferably C2-6 alkenyloxycarbonyl groups;

alkynyloxycarbonyl groups such as an ethynyloxycarbonyl group or propargyloxycarbonyl group, and preferably C2-6 alkynyloxycarbonyl groups;

aryloxycarbonyl groups such as a phenoxycarbonyl group or naphthoxycarbonyl group, and preferably C6-10 aryloxycarbonyl groups; and, aralkyloxycarbonyl groups such as a benzyloxycarbonyl group, and preferably C6-10 aryl C1-6 alkoxycarbonyl groups.

A "substituted carbamoyl group" is a group in which a C1-6 alkyl group, C2-6 alkenyl group, C2-6 alkynyl group, C6-10 aryl group, C6-10 aryl C1-6 alkyl group or 5- to 6-membered heterocyclic group is bonded to a carbamoyl group.

Examples of "substituted carbamoyl groups" include monoalkylcarbamoyl groups or dialkylcarbamoyl groups, such as a methylcarbamoyl group, ethylcarbamoyl group, dimethylcarbamoyl group or diethylcarbamoyl group, and preferably mono-C1-6 alkylcarbamoyl groups or di-C1-6 alkylcarbamoyl groups; and, monoarylcarbamoyl groups such as a phenylcarbamoyl group or 4-methylphenylcarbamoyl group, and preferably mono-C6-10 arylcarbamoyl groups.

Examples of "substituted hydroxyl groups" include alkoxy groups such as a methoxy group, ethoxy group, n-propoxy group, n-butoxy group, n-pentyloxy group, n-hexyloxy group, decyloxy group, dodecyloxy group, lauryloxy group, i-propoxy group, i-butoxy group, s-butoxy group, t-butoxy group, 1-ethylpropoxy group, i-hexyloxy group, 4-methylpentoxy group, 3-methylpentoxy group, 2-methylpentoxy group, 1-methylpentoxy group, 3,3-dimethylbutoxy group, 2,2-dimethylbutoxy group, 1,1-dimethylbutoxy group, 1,2-dimethylbutoxy group, 1,3-dimethylbutoxy group, 2,3-dimethylbutoxy group, 1-ethylbutoxy group or 2-ethylbutoxy group, and preferably C1-6 alkoxy groups;

cycloalkylalkoxy groups such as a cyclopropylmethyloxy group or 2-cyclopentylethyloxy group, and preferably C3-8 cycloalkyl C1-6 alkoxy groups; aralkyloxy groups such as a benzyloxy group, and preferably C6-10 aryl C1-6 alkoxy groups; haloalkoxy groups such as a chloromethoxy group, dichloromethoxy group, trichloromethoxy group, trifluoromethoxy group, 1-fluoroethoxy group, 1,1-difluoroethoxy group, 2,2,2-trifluoroethoxy group or pentafluoroethoxy group, and preferably C1-6 haloalkoxy groups; alkenyloxy groups such as a vinyloxy group, 1-propenyloxy group, allyloxy group, 1-butenyloxy group, 2-butenyloxy group, 3-butenyloxy group, 1-pentenyloxy group, 2-pentenyloxy group, 3-pentenyloxy group, 4-pentenyloxy group, 1-hexenyloxy group, 2-hexenyloxy group, 3-hexenyloxy group, 4-hexenyloxy group, 5-hexenyloxy group, 1-methyl-2-propenyloxy group, 2-methyl-2-propenyloxy group, 1-methyl-2-butenyloxy group or 2-methyl-2-butenyloxy group, and preferably C2-6 alkenyloxy groups;

alkynyloxy groups such as an ethynyloxy group, propynyloxy group, propargyloxy group, 1-butynyloxy group, 2-butynyloxy group, 3-butynyloxy group, 1-pentynyloxy group, 2-pentynyloxy group, 3-pentynyloxy group, 4-pentynyloxy group, 1-hexynyloxy group, 1-methyl-2-propynyloxy group, 2-methyl-3-butynyloxy group, 1-methyl-2-butynyloxy group, 2-methyl-3-pentynyloxy group or 1,1-dimethyl-2-butynyloxy group, and preferably C2-6 alkynyloxy groups; cycloalkyloxy groups such as a cyclopropyloxy group, cyclobutyloxy group, cyclopentyloxy group, cyclohexyloxy group, cycloheptyloxy group, cyclooctyloxy group, 2-methylcyclopropyloxy group, 2-ethylcyclopropyloxy group, 2,3,3-trimethylcyclobutyloxy group, 2-methylcyclopentyloxy group, 2-ethylcyclohexyloxy group, 2-ethylcyclooctyloxy group, 4,4,6,6-tetramethylcyclohexyloxy group or 1,3-dibutylcyclohexyloxy group, and preferably C3-6 cycloalkyloxy groups; aryloxy groups such as a phenyloxy group, naphthyloxy group, azurenyloxy group, indenyloxy group, indanyloxy group or tetralinyloxy group, and preferably C6-10 aryloxy groups;

arylalkyloxy groups (aralkyloxy groups) such as a benzyloxy group, phenethyloxy group or 2-naphthylmethyloxy group, and preferably C6-10 aryl C1-6 alkyloxy groups;

acyloxy groups such as an acetyloxy group, propionyloxy group, n-propylcarbonyloxy group, i-propylcarbonyloxy group, n-butylcarbonyloxy group, i-butylcarbonyloxy group, pentanoyloxy group or pivaloyloxy group, and preferably C1-7 acyloxy groups;

alkoxycarbonylalkyloxy groups such as a methoxycarbonylmethyloxy group or 1-methoxycarbonyl-1-methylethyloxy group, and preferably C1-6 alkoxycarbonyl C1-6 alkoxy groups; and, trialkylsilyloxy groups such as trimethylsilyloxy group or t-butyldimethylsilyloxy group, and preferably tri-C1-6 alkylsilyloxy groups.

Examples of "substituted amino groups" include alkylamino groups such as a methylamino group, ethylamino group, n-propylamino group, n-butylamino group, dimethylamino group or diethylamino group, and preferably mono-C1-6 alkylamino groups or di-C1-6 alkylamino groups; mono-C1-6 alkylidene amino groups such as a methylidene amino group or ethylidene amino group; monoarylamino groups such as a phenylamino group or 4-methylphenylamino group, and preferably mono-C6-10 arylamino groups; diarylamino groups such as a di-1-naphthylamino group, and preferably di-C6-10 arylamino groups; aralkylamino groups such as a benzylamino group, and preferably C6-10 aryl C1-6 alkylamino groups; acylamino groups such as an acetylamino group, trifluoroacetylamino group or benzoylamino group, and preferably C1-6 acylamino groups; and, alkoxycarbonylamino groups such as a methoxycarbonylamino group or t-butoxycarbonylamino group, and preferably C1-6 alkoxycarbonylamino groups.

Examples of "substituted mercapto groups" include alkylthio groups such as a methylthio group or ethylthio group, and preferably C1-6 alkylthio groups; arylthio groups such as a phenylthio group or 4-methylphenylthio group, and preferably C6-10 arylthio groups; and acylthio groups such as an acetylthio group or benzoylthio group, and preferably C1-6 acylthio groups.

Examples of "substituted sulfonyl groups" include alkylsulfonyl groups such as a methylsulfonyl group, ethylsulfonyl group, n-propylsulfonyl group, i-propylsulfonyl group, n-butylsulfonyl group, i-butylsulfonyl group, s-butylsulfonyl group, t-butylsulfonyl group, n-pentylsulfonyl group, i-pentylsulfonyl group, neopentylsulfonyl group, 1-ethylpropylsulfonyl group, n-hexylsulfonyl group or i-hexylsulfonyl group, and preferably C1-6 alkylsulfonyl groups; haloalkylsulfonyl groups such as a trifluoromethylsulfonyl group, and preferably C1-6 haloalkylsulfonyl groups; arylsulfonyl groups such as a phenylsulfonyl group or 4-methylphenylsulfonyl group, and preferably C6-10 arylsulfonyl groups; sulfo groups; alkoxysulfonyl groups such as a methoxysulfonyl group or ethoxysulfonyl group, and preferably C1-6 alkoxysulfonyl groups; sulfamoyl groups; sulfamoyl groups such as an N-methylsulfamoyl group, N-ethylsulfamoyl group, N,N-dimethylsulfamoyl group or N,N-diethylsulfamoyl group, and preferably mono-C1-6 alkylsulfamoyl groups or di-C1-6 alkylsulfamoyl groups; and, monoarylsulfamoyl groups such as a phenylsulfamoyl group or 4-methylphenylsulfamoyl group, and preferably mono-C6-10 arylsulfamoyl groups.

Examples of "halogeno groups" include a fluorine atom, chlorine atom, bromine atom and iodine atom.

$R^1$ and $R^2$ may together form an unsubstituted or substituted 5- to 8-membered ring or may form a group represented by =O, a group represented by =$CR^aR^b$, or a group represented by =N—R'.

Here, $R^a$ represents a hydrogen atom or an unsubstituted or substituted C1-8 alkyl group. $R^b$ represents a hydrogen atom or an unsubstituted or substituted C1-8 alkyl group. R' represents an unsubstituted or substituted hydroxyl group or unsubstituted or substituted C1-8 alkyl group.

Examples of unsubstituted or substituted C1-8 alkyl groups in $R^a$, $R^b$ and R' are the same as the "C1-8 alkyl groups" exemplified in the aforementioned $R^1$ to $R^3$.

Examples of substituted hydroxyl groups in R' are the same as the "substituted hydroxyl groups" exemplified in the aforementioned $R^1$ to $R^3$.

Examples of unsubstituted or substituted 5- to 8-membered rings able to be jointly formed by $R^1$ and $R^2$ include aliphatic hydrocarbon rings such as a cyclopropane ring, cyclobutane ring, cyclopentane ring, cyclohexane ring, cycloheptane ring or cyclooctane ring, and preferably C3-8 cycloalkane rings; and, unsaturated heterocycles such as an oxirane ring, [1,3]dioxirane ring, dihydro-2H-pyran ring, dihydro-2H-thiopyran ring or tetrahydropyridine ring, and preferably oxygen-containing 3- to 5-membered unsaturated heterocycles.

[$X^1$, m]

$X^1$ respectively and independently represents an unsubstituted or substituted C1-8 alkyl group, an unsubstituted or substituted C2-8 alkenyl group, an unsubstituted or substituted C2-8 alkynyl group, an unsubstituted or substituted hydroxyl group, a halogeno group, a cyano group or a nitro group.

m represents the number of $X^1$ and is an integer of 0 to 5.

Examples of groups represented by $X^1$ are the same as those exemplified as groups represented by $R^1$ to $R^3$.

Preferable examples of $X^1$ include C1-6 alkyl groups, C1-6 haloalkyl groups, C2-6 alkenyl groups, C3-8 cycloalkyl groups, a hydroxyl group, C1-6 alkoxy groups and halogeno groups.

[$X^2$, n]

$X^2$ respectively and independently represents an unsubstituted or substituted C1-8 alkyl group, an unsubstituted or substituted C2-8 alkenyl group, an unsubstituted or substituted C2-8 alkynyl group, an unsubstituted or substituted C3-8 cycloalkyl group, an unsubstituted or substituted C4-8 cycloalkenyl group, an unsubstituted or substituted C6-10 aryl group, an unsubstituted or substituted heterocyclic group, an unsubstituted or substituted C1-8 acyl group, an unsubstituted or substituted (1-imino)C1-8 alkyl group, an unsubstituted or substituted carboxyl group, an unsubstituted or substituted carbamoyl group, an unsubstituted or substituted hydroxyl group, an unsubstituted or substituted amino group, an unsubstituted or substituted mercapto group, a substituted sulfonyl group, a halogeno group, a cyano group or a nitro group.

n represents the number of $X^2$ and is an integer of 0 to 3.

Examples of groups represented by $X^2$ are the same as those groups exemplified as groups represented by $R^1$ to $R^3$.

Preferable examples of $X^2$ include C1-6 alkyl groups, C1-6 haloalkyl groups, C6-10 aryl C1-6 alkyl groups, C3-8 cycloalkyl groups, C6-10 aryl groups, C1-7 acyl groups, C1-6 alkoxycarbonyl groups, C1-6 alkoxy groups, an amino group, mono-C1-6 alkylamino groups, di-C1-6 alkylamino groups, C1-6 alkoxycarbonylamino groups, C1-6 alkylthio groups, C1-6 alkylsulfonyl groups, a halogeno group, a cyano group and a nitro group.

Here, any one of $R^1$ to $R^3$ and any one of $X^2$ may together form an unsubstituted or substituted 5- to 8-membered ring.

Examples of 5- to 8-membered rings include aromatic hydrocarbon rings such as a benzene ring; and, C5-8 cycloalkene rings such as a cyclopentene ring, cyclopentadiene ring, cyclohexene ring, cycloheptene ring or cyclooctene ring.

[B, D]

B represents a carbon atom or a nitrogen atom. In other words, B composes a pyridine ring in which "D" has condensed or a pyrazine ring in which "D" has condensed.

D represents an unsubstituted or $X^1$-substituted 5- to 7-membered hydrocarbon ring or an unsubstituted or $X^1$-substituted 5- to 7-membered heterocycle.

Examples of 5- to 7-membered hydrocarbon rings include aromatic hydrocarbon rings such as a benzene ring; C5-7 cycloalkene rings such as a cyclopentene ring, cyclohexene ring or cycloheptene ring; aromatic 5- to 7-membered heterocycles such as a furan ring, thiophene ring, pyrrole ring, imidazole ring, pyrazole ring, thiazole ring, oxazole ring, isoxazole ring, pyridine ring, pyrazine ring, pyrimidine ring, pyridazine ring, azepine ring or diazepine ring; and, unsaturated 5- to 7-membered heterocycles such as a dihydro-2H-pyran ring, dihydro-2H-thiopyran ring or tetrahydropyridine ring.

Among these, aromatic hydrocarbon rings are preferable, and a benzene ring is more preferable. Namely, the compound according to the present invention is preferably a compound that has a quinoline ring or quinoxaline ring.

[$A^1$, $A^2$, $A^3$, $A^4$]

$A^1$, $A^2$, $A^3$ and $A^4$ respectively and independently represent a carbon atom or a nitrogen atom. Namely, $A^1$, $A^2$, $A^3$ and $A^4$ compose a benzene ring, pyridine ring, pyridazine ring, pyrimidine ring, pyrazine ring or triazine ring.

However, in the case B is a carbon atom, $A^1$ to $A^4$ are not all carbon atoms.

Among these, a pyridine ring is preferable. A pyridine ring in which $A^1$ is a nitrogen atom is more preferable for the pyridine ring.

There are no particular limitations on salts of the compound of the present invention provided they are agriculturally or horticulturally allowable salts. Examples of salts include salts of inorganic acids such as hydrochloric acid or sulfuric acid; salts of organic acids such as acetic acid or lactic acid; salts of alkaline metals such as lithium, sodium or potassium; salts of alkaline earth metals such as calcium or magnesium; salts of transition metals such as iron or copper; and, salts of organic bases such as ammonia, triethylamine, tributylamine, pyridine or hydrazine.

The compound represented by the aforementioned formula (I) is preferably a compound represented by formula (II) (to also be indicated as "Compound (II)").

The compound represented by formula (II) is a compound in which "D" in formula (I) is a benzene ring. Namely, the compound of the present invention is preferably a compound having a quinoline ring or quinoxaline ring.

[Chemical Formula 13]

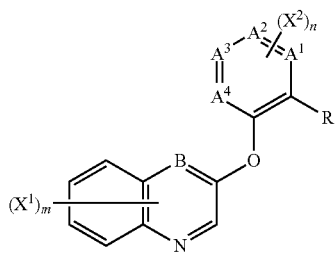

(II)

Here, R, $X^1$, m, $X^2$, n, $A^1$, $A^2$, $A^3$, $A^4$ and B in formula (II) have the same meanings as previously described.

The compound represented by the aforementioned formula (II) is preferably a compound represented by formula (III) (to also be indicated as "Compound (III)") or a compound represented by formula (V) (to also be indicated as "Compound (V)").

[Chemical Formula 14]

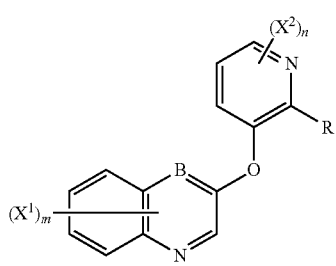

(III)

The compound represented by formula (III) is a compound in which "$A^1$" in formula (II) is a nitrogen atom and "$A^2$ to $A^4$" are carbon atoms. Namely, the compound of the present invention is preferably a compound having either a quinoline ring or quinoxaline ring and a pyridine ring.

Here, R, $X^1$, m, $X^2$, n and B in formula (III) have the same meanings as previously described.

The compound represented by the aforementioned formula (III) is preferably a compound represented by formula (IV) (to also be indicated as "Compound (IV)").

[Chemical Formula 15]

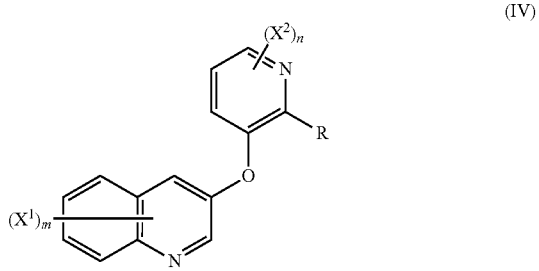

(IV)

R, $X^1$, m, $X^2$ and n in formula (IV) have the same meanings as previously described.

The compound represented by formula (IV) is a compound in which "B" in formula (III) is a carbon atom. Namely, the compound of the present invention is preferably a compound having a quinoline ring and a pyridine ring.

[Chemical Formula 16]

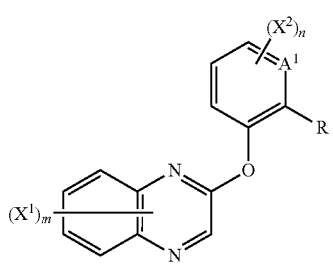

(V)

The compound represented by formula (V) is a compound in which "B" in formula (II) is a nitrogen atom and "$A^2$ to $A^4$" are carbon atoms. Namely, the compound of the present invention is preferably a compound having a quinoxaline ring and either a benzene ring or pyridine ring.

Here, R, $X^1$, m, $X^2$, n and $A^1$ in formula (V) have the same meanings as previously described.

The compound represented by the aforementioned formula (V) is preferably a compound represented by formula (VI) (to also be indicated as "Compound (VI)").

[Chemical Formula 17]

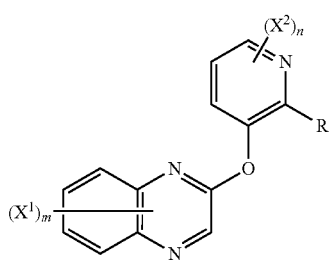

(VI)

The compound represented by formula (VI) is a compound in which "$A^1$" in formula (V) is a nitrogen atom. Namely, the compound of the present invention is preferably a compound having a quinoxaline ring and a pyridine ring.

Here, R, $X^1$, m, $X^2$ and n in formula (VI) have the same meanings as previously described.

(Production Method of Compound of Present Invention)

The compound of the present invention can be produced according to the synthesis methods indicated below.

(Synthesis Method 1)

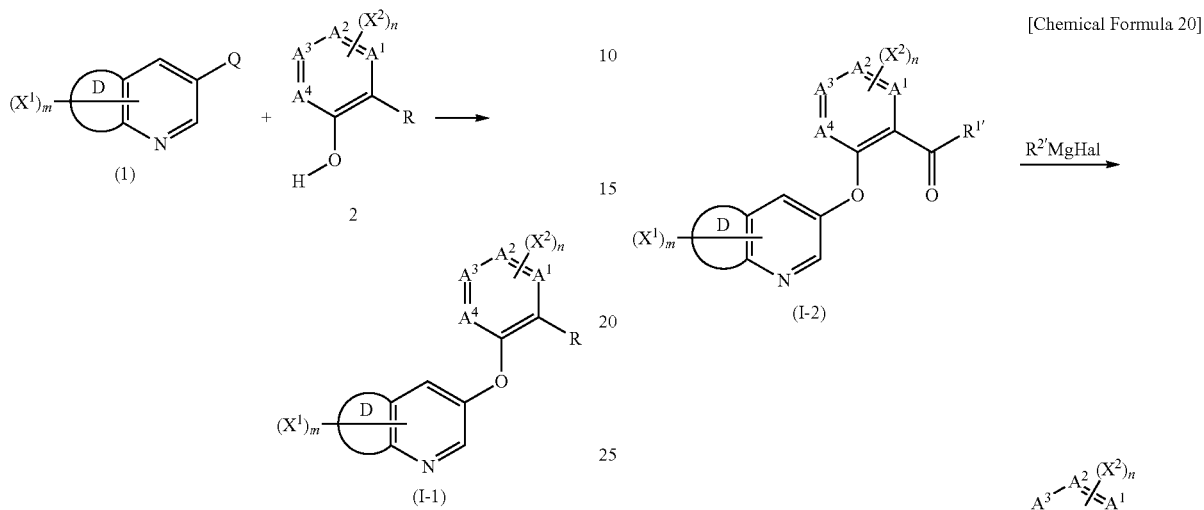

In the above formulas, R, $X^1$, m, $X^2$, n, D and $A^1$ to $A^4$ have the same meanings as previously described. Q represents a halogen atom.

A compound represented by formula (I-1) (to also be indicated as Compound I-1)) can be produced by reacting a compound represented by formula (1) with a compound represented by formula (2) according to a known method.

In synthesis method 1,7,8-difluoro-3-iodoquinoline is a useful production intermediate.

(Synthesis Method 2)

[Chemical Formula 19]

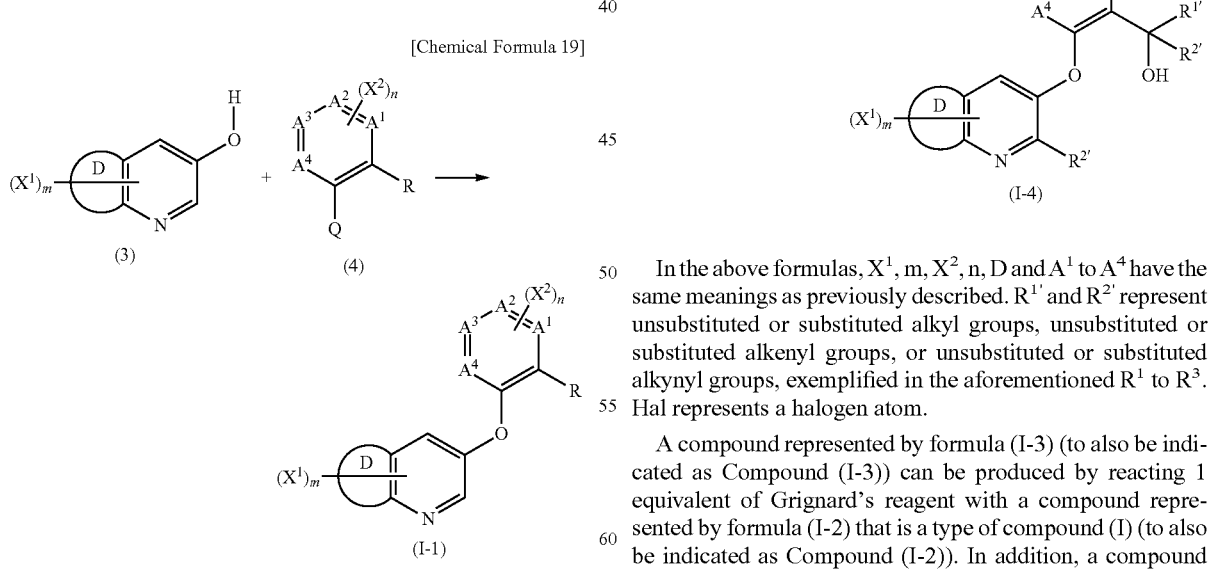

In the above formulas, Q, R, $X^1$, m, $X^2$, n, D and $A^1$ to $A^4$ have the same meanings as previously described.

Compound (I-1) can be produced by reacting a compound represented by formula (3) with a compound represented by formula (4) according to a known method.

In synthesis method 2,8-fluoro-3-hydroxyquinoline, 7,8-difluoro-3-hydroxyquinoline, 8-fluoro-3-hydroxy-2-methylquinoline or 7,8-difluoro-3-hydroxy-2-methylquinoline is a useful production intermediate.

(Synthesis Method 3)

[Chemical Formula 20]

In the above formulas, $X^1$, m, $X^2$, n, D and $A^1$ to $A^4$ have the same meanings as previously described. $R^{1'}$ and $R^{2'}$ represent unsubstituted or substituted alkyl groups, unsubstituted or substituted alkenyl groups, or unsubstituted or substituted alkynyl groups, exemplified in the aforementioned $R^1$ to $R^3$. Hal represents a halogen atom.

A compound represented by formula (I-3) (to also be indicated as Compound (I-3)) can be produced by reacting 1 equivalent of Grignard's reagent with a compound represented by formula (I-2) that is a type of compound (I) (to also be indicated as Compound (I-2)). In addition, a compound represented by formula (I-4) (to also be indicated as Compound (I-4)) is formed in addition to Compound (I-3) when an amount of Grignard's reagent in excess of 1 equivalent is reacted with Compound (I-2), and Compound (I-4) can be produced by reacting with 2 equivalents of Grignard's reagent.

(Synthesis Method 4)

(Synthesis Example 5)

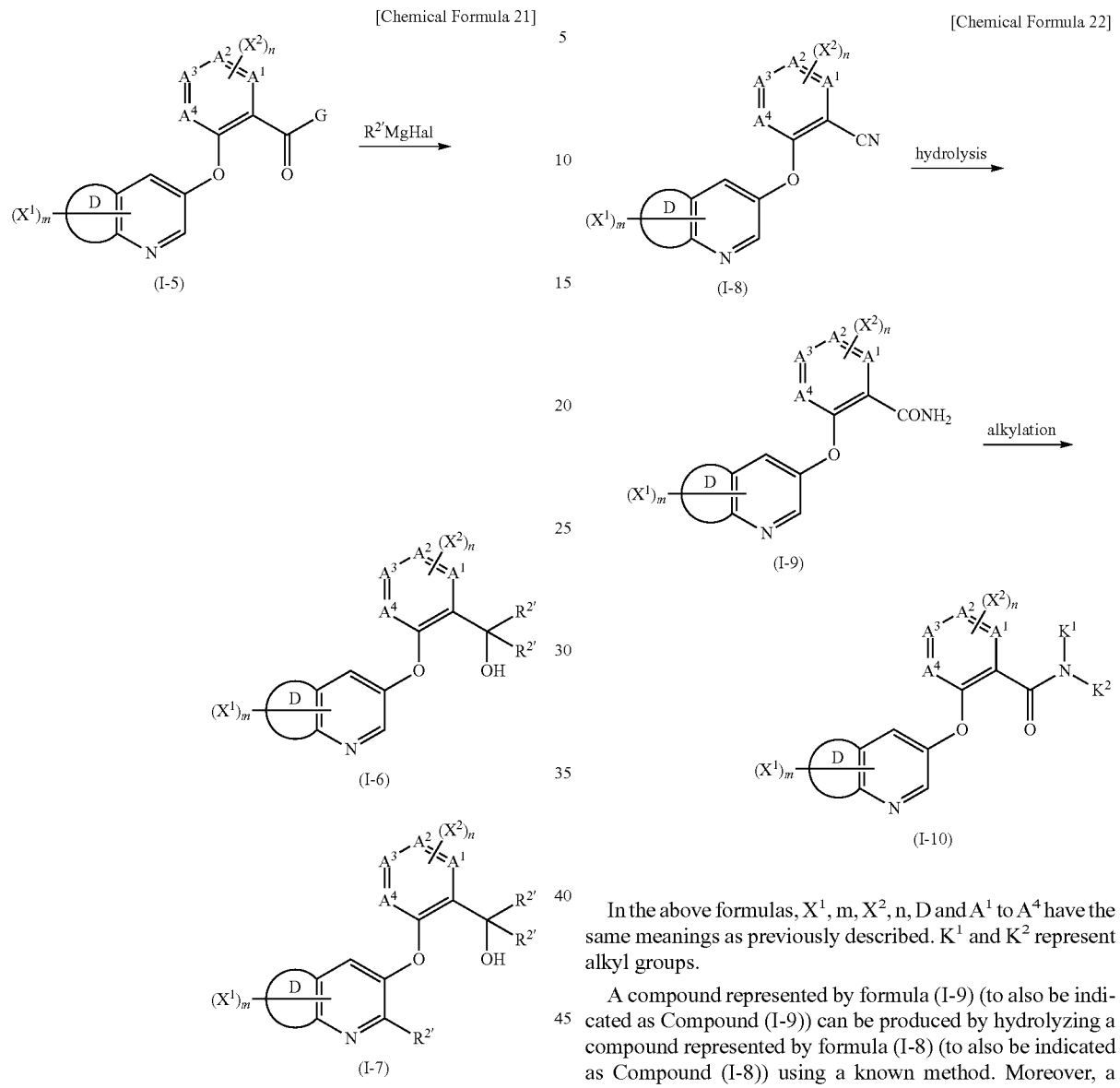

In the above formulas, $R^{2'}$, Hal, $X^1$, m, $X^2$, n, D and $A^1$ to $A^4$ have the same meanings as previously described. G represents a leaving group such as an alkoxy group or halogen atom.

A compound represented by formula (I-6) (to also be indicated as Compound (I-6)) can be produced by reacting 2 equivalents of Grignard's reagent with a compound represented by formula (I-5) that is a type of Compound (I) (to also be indicated as Compound (I-5)). In addition, when an amount of Grignard's reagent in excess of 2 equivalents is reacted with Compound (I-5), a compound represented by formula (I-7) (to also be indicated as Compound (I-7)) is formed in addition to Compound (I-6), and Compound (I-7) can be produced by reacting with 3 equivalents of Grignard's reagent.

In the above formulas, $X^1$, m, $X^2$, n, D and $A^1$ to $A^4$ have the same meanings as previously described. $K^1$ and $K^2$ represent alkyl groups.

A compound represented by formula (I-9) (to also be indicated as Compound (I-9)) can be produced by hydrolyzing a compound represented by formula (I-8) (to also be indicated as Compound (I-8)) using a known method. Moreover, a compound represented by formula (I-10) (to also be indicated as Compound (I-10)) can be synthesized by allowing an alkylating agent to act in the presence of a base.

(Synthesis Method 6)

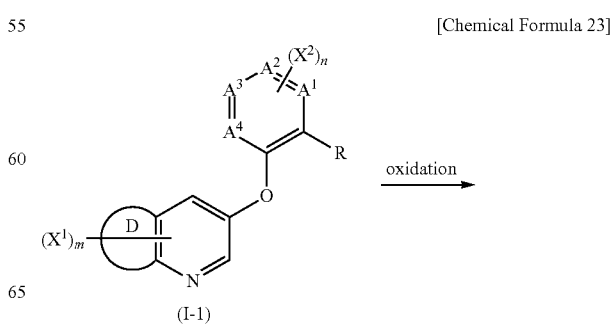

-continued

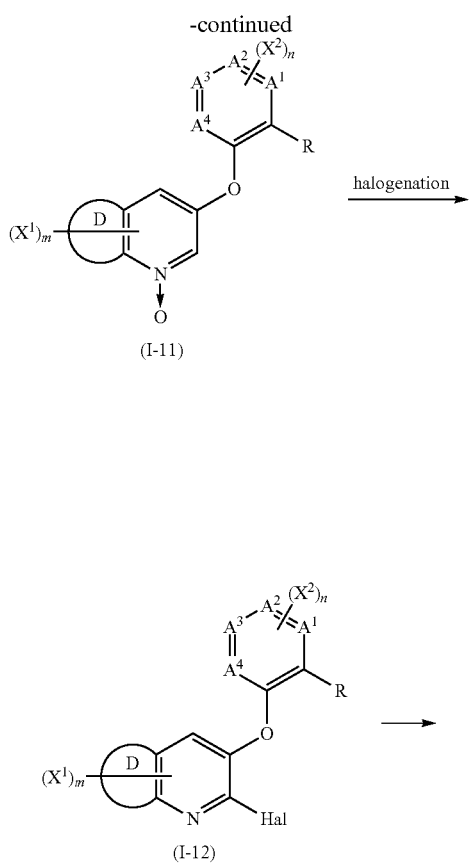

(I-11)

(I-12)

(I-13)

In the above formulas, Hal, R, $X^1$, m, $X^2$, n, D and $A^1$ to $A^4$ have the same meanings as previously described. $X1'$ represents an unsubstituted or substituted alkoxy group, an unsubstituted or substituted alkyl group, an unsubstituted or substituted alkenyl group, or an unsubstituted or substituted alkynyl group.

An N-oxide compound represented by formula (I-11) (to also be indicated as Compound (I-11)) can be produced by oxidizing compound (I-1) using a known method such as by using an oxidizing agent. A compound represented by formula (I-12) (to also be indicated as Compound (I-12)) can be produced by allowing a known halogenating agent such as phosphorous oxychloride to act on Compound (I-11). A compound represented by formula (I-13) (to also be indicated as Compound (I-13)) can be synthesized by carrying out a nucleophilic substitution reaction or a coupling reaction using an organometallic catalyst on Compound (I-12).

(Synthesis Method 7)

[Chemical Formula 24]

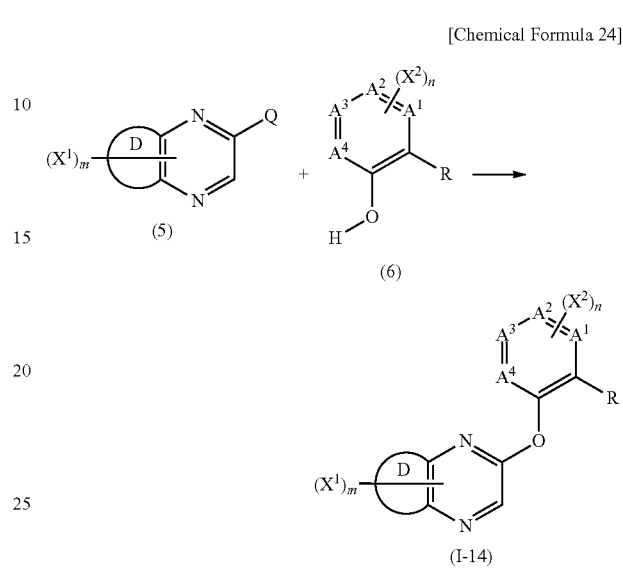

(5)

(6)

(I-14)

In the above formulas, R, $X^1$, m, $X^2$, n, D and $A^1$ to $A^4$ have the same meanings as previously described. Q represents a halogeno group.

A compound represented by formula (I-14) (to also be indicated as Compound (I-14)) can be produced by reacting with a compound represented by formula (5) and a compound represented by formula (6) according to a known method.

(Synthesis Method 8)

[Chemical Formula 25]

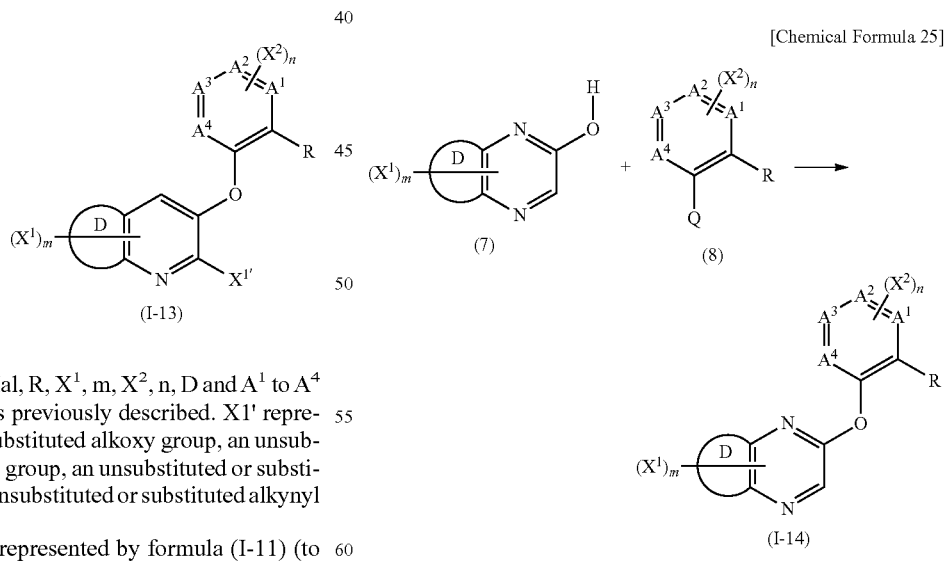

(7)

(8)

(I-14)

In the above formulas, Q, R, $X^1$, m, $X^2$, n, D and $A^1$ to $A^4$ have the same meanings as previously described.

Compound (I-14) can be produced by reacting with a compound represented by formula (7) and a compound represented by formula (8) according to a known method.

(Synthesis Method 9)

[Chemical Formula 26]

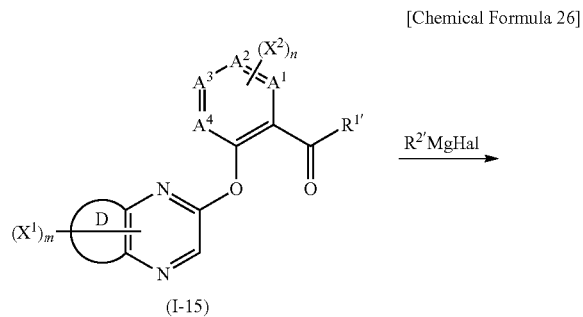

(I-15)

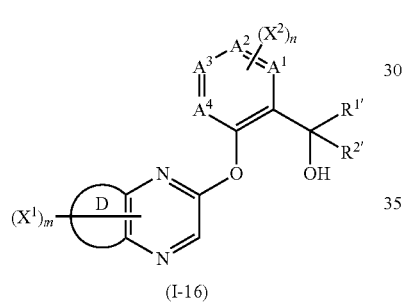

(I-16)

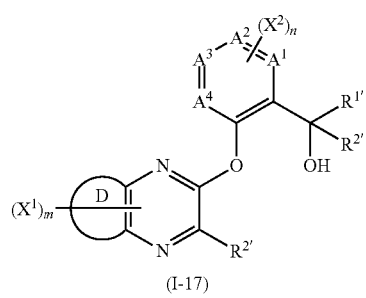

(I-17)

In the above formulas, $X^1$, m, $X^2$, n, D and $A^1$ to $A^4$ have the same meanings as previously described. $R^{1'}$ and $R^{2'}$ represent unsubstituted or substituted alkyl groups, unsubstituted or substituted alkenyl groups, or unsubstituted or substituted alkynyl groups, exemplified in the aforementioned $R^1$ to $R^3$. Hal represents a halogeno group.

A compound represented by formula (I-16) (to also be indicated as Compound (I-16)) can be produced by reacting 1 equivalent of Grignard's reagent ($R^{2'}$MgHal) with a compound represented by formula (I-15) that is a type of compound (I) (to also be indicated as Compound (I-15)). In addition, a compound represented by formula (I-17) (to also be indicated as Compound (I-17)) can be produced by reacting 2 or more equivalents of Grignard's reagent with Compound (I-15).

(Synthesis Example 10)

[Chemical Formula 27]

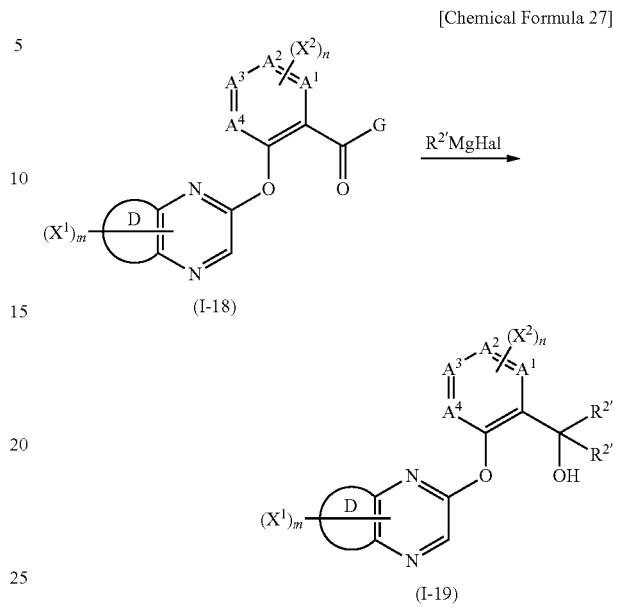

In the above formulas, $R^{2'}$, Hal, $X^1$, m, $X^2$, n, D and $A^1$ to $A^4$ have the same meanings as previously described. G represents a leaving group such as an alkoxy group or halogeno group.

A compound represented by formula (I-19) (to also be indicated as Compound (I-19)) can be produced by reacting 2 equivalents of Grignard's reagent with a compound represented by formula (I-18) that is a type of Compound (I) (to also be indicated as Compound (I-18)). In addition, a compound represented by formula (I-20) (to also be indicated as Compound (I-20)) can be produced by reacting 3 or more equivalents of Grignard's reagent with Compound (I-18).

Salts of Compounds (I) to (VI) according to the present invention can be prepared by contacting an inorganic acid compound, organic acid compound, alkaline metal compound, alkaline earth metal compound, transition metal compound, ammonium compound, or the like, with Compounds (I) to (VI).

In each of these reactions, the target product can be efficiently isolated by carrying out an ordinary post-treatment procedure used in the field of synthetic organic chemistry following completion of the reaction, and carrying out a conventionally known separation and purification means as necessary.

The structure of a target product can be identified and confirmed by, for example, $^1$H-NMR spectral analysis, IR spectral analysis, mass spectrometry or elementary analysis.

2) Agricultural or Horticultural Fungicide

The agricultural or horticultural fungicide according to the present invention contains as an active ingredient thereof at least one type of compound selected from the group consisting of the aforementioned nitrogenated heterocyclic compounds represented by formulas (I) to (VI) and salts thereof.

The fungicide of the present invention demonstrates excellent fungicidal activity against a wide range of fungi types, such as Oomycetes, Ascomycetes, Deuteromycetes or Basidiomycetes.

The fungicide of the present invention can be used to control various diseases that occur during cultivation of agricultural and horticultural crops including flowering plants, lawn grasses and pasture grasses by seed treatment, foliar spraying, soil application, water surface application, or the like.

For example, the fungicide of the present invention may be used to control the followings:

sugar Beets: cercospora leaf spot (*Cercospora beticola*), aphanomyces root rot (*Aphanomyces cochlloides*), root rot (*Thanatephorus cucumeris*), or leaf rot (*Thanatephorus cucumeris*);

peanuts: brown leaf spot (*Mycosphaerella arachidis*), or leaf spot (*Mycosphaerella berkeleyi*);

cucumbers: powdery mildew (*Sphaerotheca fuliginea*), downy mildew (*Pseudoperonospora cubensis*), gummy stem blight (*Mycosphaerella melonis*), stem rot (*Fusarium oxysporum*), sclerotinia rot (*Sclerotinia sclerotiorum*), gray mold (*Botrytis cinerea*), anthracnose (*Colletotrichum obriculare*), scab (*Cladosporium cucumerinum*), corynespora leaf spot (*Corynespora cassicola*), damping-off (*Pythium debaryanam, Rhizoctonia solani* Kuhn), or bacterial spot (*Pseudomonas syringae* pv. Lecrymans);

tomatoes: gray mold (*Botrytis cinerea*), leaf mold (*Cladosporium fulvum*), or late blight (*Phytophthora infestans*);

eggplants: gray mold (*Botrytis cinerea*), black rot (*Corynespora melongenae*), powdery mildew (*Erysiphe cichoracearum*), or leaf mold (*Mycovelloslella nattrassii*);

strawberries: gray mold (*Botrytis cinerea*), powdery mildew (*Sohaerotheca humuli*), anthracnose (*Colletotrichum acutatum, Colletotrichum fragariae*), or blight (*Phytophthora cactorum*);

onions: neck rot (*Botrytis allii*), gray mold (*Botrytis cinerea*), leaf blight (*Botrytis squamosa*), or downy mildew (*Peronospora destructor*);

cabbage: clubroot (*Plasmodiophora brassicae*), bacterial soft rot (*Erwinia carotovora*), or downy mildew (*Peronospora parasitica*);

kidney beans: stem rot (*Sclerotinia sclerotiorum*), or gray mold (*Botrytis cinerea*);

apples: powdery mildew (*Podosphaera leucotricha*), scab (*Venturia inaequalis*), blossom blight (*Monilinia mali*), fruit spot (*Mycosphaerella pomi*), valsa canker (*Valsa mali*), alternaria blotch (*Alternaria mali*), rust (*Gymnosporangium yamadae*), ring rot (*Botryosphaeria berengeriana*), anthracnose (*Glomerella cingulata, Colletotrichum acutatum*), blotch (*Diplocarpon mali*), flyspeck (*Zygophiala jamaicensis*), or sooty blotch (*Gloeodes pomigena*);

persimmons: powdery mildew (*Phyllactinia kakicola*), anthracnose (*Gloeosporium kaki*), or angular leaf spot (*Cercospora kaki*);

peaches: brown rot (*Monilinia fructicola*), scab (*Cladosporium carpophilum*), or phomopsis rot (*Phomopsis* sp.);

Prunus avium: brown rot (*Monolinia fructicola*);

grapes: gray mold (*Botrytis cinerea*), powdery mildew (*Uncinula necator*), ripe rot (*Glomerella cingulata, Colletotrichum acutatum*), downy mildew (*Plasmopara viticola*), anthracnose (*Elsinoe ampelina*), brown spot (*Pseudocercospora vitis*), or black rot (*Guignardia bidwellii*);

pears: scab (*Venturia nashicola*), rust (*Gymnosporangium asiaticum*), black spot (*Alternaria kikuchiana*), ring rot (*Botryosphaeria berengeriana*), or powdery mildew (*Phyllactinia mali*);

tea: gray blight (*Pestalotia theae*), or anthracnose (*Collectotrichum theae-sinensis*);

citrus: scab (*Elsinoe fawcetti*), blue mold (*Penicillium italicum*), common green mold (*Penicillium digitatum*), gray mold (*Botrytis cinerea*), melanose (*Diaporthe citri*), or canker (*Xanthomonas campestris* pv. *Citri*);

wheat: powdery mildew (*Erysiphe graminis* f. sp. *tritici*), fusarium blight (*Gibberella zeae*), leaf rust (*Puccinia recondita*), browning root rot (*Pythium iwayamai*), snow mold (*Monographella nivalis*), eye spot (*Pseudocercosporella herpotrichoides*), speckled leaf blotch (*Septoria tritici*), glume blotch (*Leptosphaeria nodorum*), typhula snow blight (*Typhula incarnata*), sclerotinia snow blight (*Myriosclerotinia borealis*), or take-all (*Gaeumanomyces graminis*);

barley: stripe (*Pyrenophora graminea*), leaf blotch (*Rhynchosporium secalis*), or loose smut (*Ustilago tritici, U. nuda*);

rice: blast (*Pyricularia oryzae*), sheath blight (*Rhizoctonia solani*), bakanae disease (*Gibberella fujikuroi*), brown spot (*Cochliobolus niyabeanus*), seedling blight (*Pythium graminicolum*), bacterial leaf blight (*Xanthomonas oryzae*), bacterial seedling blight (*Burkholderia plantarii*), bacterial brown stripe (*Acidovorax avanae*), or bacterial grain rot (*Burkholderia glumae*);

tobacco: sclerotinia stem-rot (*Sclerotinia sclerotiorum*), or owdery mildew (*Erysiphe cichoracearum*);

tulips: gray mold (*Botrytis cinerea*);

bent grass: sclerotinia snow blight (*Sclerotinia borealis*), or bacterial shoot blight (*Pythium aphanidermatum*);

orchard grass: powdery mildew (*Erysiphe graminis*);

soybeans: purple stain (*Cercospora kikuchii*), Downy mildew (*Peronospora Manshurica*), or stem rot (*Phytophthora sojae*); or potatoes and tomatoes: late blight (*Phytophthora infestans*).

In addition, the fungicide of the present invention also demonstrates excellent fungicidal activity against resistant organisms. Examples of resistant organisms include: gray mold (*Botrytis cinerea*), sugar beet cercospora leaf spot (*Cercospora beticola*), apple scab (*Venturia inaequalis*) and pear scab (*Venturia nashicola*), which exhibit resistance to benzimidazole fungicides, such as thiophanate-methyl, benomyl, or carbendazim; and gray mold (*Botrytis cinerea*), which exhibits resistance to dicarboxiimide bactericides (such as vinclozoline, procymidone, or iprodione).

Examples of diseases for which application of the fungicide of the present invention is more preferable include apple scab, cucumber gray mold, wheat powdery mildew, tomato late blight, wheat leaf rust, rice blast and cucumber stem rot.

In addition, the fungicide of the present invention causes little chemical damage, exhibits low toxicity to fish and warm-blooded animals, and has a high degree of safety.

The fungicide of the present invention can be used in a form able to be adopted by agricultural chemicals, namely in the form of an agricultural chemical preparation such as a wettable powder, granules, powder, emulsion, aqueous solution, suspension or wettable granules.

Examples of additives and carriers used in solid preparations include vegetable powders such as soybean powder or wheat powder, mineral fine powders such as diatomaceous earth, apatite, gypsum, talc, bentonite, pyrophyllite or clay, and organic or inorganic compounds such as sodium benzoate, urea or sodium sulfate.

Examples of solvents used in liquid preparations include kerosene, xylene and petroleum-based aromatic hydrocarbons, cyclohexane, cyclohexanone, dimethylformamide, dimethylsulfoxide, alcohol, acetone, trichloroethylene, methyl isobutyl ketone, mineral oil, vegetable oil and water.

Moreover, a surfactant can be added to these preparations as necessary to obtain a uniform and stable form.

There are no particular limitations on surfactants able to be added. Examples thereof include nonionic surfactants such as polyoxyethylene-added alkyl phenyl ethers, polyoxyethylene-added alkyl ethers, polyoxyethylene-added higher fatty acid esters, polyoxyethylene-added sorbitan fatty acid esters or polyoxyethylene-added tristyryl phenyl ether, and sulfuric acid ester salts of polyoxyethylene-added alkyl phenyl ethers, alkyl benzene sulfonates, sulfuric acid ester salts of higher alcohols, alkyl naphthalene sulfonates, polycarboxylates, lignin sulfonates, formaldehyde condensates of alkyl naphthalene sulfonates and isobutylene-maleic anhydrate copolymers.

Wettable powders, emulsions, flowable agents, aqueous solutions, or wettable granules, obtained in the aforementioned manner, are used by spraying onto plants in the form of solutions, suspensions, or emulsions, after diluting to a prescribed concentration with water. In addition, powders and granules are used by spraying directly onto plants.

Normally, the amount of active ingredient in the fungicide of the present invention is preferably 0.01 to 90% by weight and more preferably 0.05 to 85% by weight based on the total weight of the preparation.

Although the applied amount of the fungicide of the present invention varies according to weather conditions, preparation form, application time, application method, applied location, target control disease, target crop, or the like, it is normally 1 to 1,000 g, and preferably 10 to 100 g, as the amount of active ingredient, per hectare.

In the case of applying by diluting a wettable powder, emulsion, suspension, aqueous solution, wettable granules, or the like, with water, the applied concentration is 1 to 1000 ppm and preferably 10 to 250 ppm.

The fungicide of the present invention can also be mixed with other fungicides, insecticides, acaricides, plant growth regulators or synergists.

Typical examples of other fungicides, insecticides, acaricides, and plant growth regulators, able to be used by mixing with the fungicide of the present invention, are indicated below.

Fungicides:

(1) Benzoimidazole-based fungicides: benomyl, carbendazim, fuberidazole, thiabendazole, thiophanate-methyl, and the like;

(2) Dicarboxylmide-based fungicides: chlozolinate, iprodione, procymidone, vinclozolin, and the like;

(3) DMI-fungicides: imazalil, oxpoconazole, pefurazoate, prochloraz, triflumizole, triforine, pyrifenox, fenarimol, nuarimol, azaconazole, bitertanol, bromuconazole, cyproconazole, difenoconazole, diniconazole, epoxyconazole, fenbuconazole, fluquinconazole, flusilazole, flutriafol, hexaconazol, imibenconazole, ipconazole, metconazole, miclobutanil, penconazole, propiconazole, prothioconazole, simeconazole, tebuconazole, tetraconazole, triadimefon, triadimenol, triticonazole, etaconazole, furconazole-cis, and the like;

(4) Phenylamide-based fungicides: benalaxyl, furalaxyl, metalaxyl, metalaxyl-M, oxadixyl, ofurace, and the like;

(5) Amine-based fungicides: aldimorph, dodemorph, fenpropimorph, tridemorph, fenpropidine, piperalin, spiroxamine, and the like;

(6) Phosphothiolate-based fungicides: EDDP, iprobenfos, pyrazophos, and the like;

(7) Dithiolane-based fungicides: isoprothiolane, and the like;

(8) Carboxamide-based fungicides: benodanil, boscalid, carboxin, fenfuram, flutolanil, furametpyr, mepronil, oxycarboxin, penthiopyrad, thifluzamide, and the like;

(9) Hydroxy-(2-amino)pyrimidine-based fungicides: bupirimate, dimethirimol, ethirimol, and the like;

(10) AP (anilinopyrimidine-based) fungicides: cyprodinil, mepanipyrim, pyrimethanil, and the like;

(11) N-phenylcarbamate-based fungicides: diethofencarb, and the like;

(12) QoI-based fungicides (Qo inhibitors): azoxystrobin, picoxystrobin, pyraclostrobin, kresoxim-methyl, trifloxystrobin, dimoxystrobin, metominostrobin, orysastrobin, famoxadone, fluoxastrobin, fenamidone, metominofen, and the like;

(13) PP (phenylpyrrole)-based fungicides: fenpiconil, fludioxonil, and the like;

(14) Quinoline-based fungicides: quinoxyfen, and the like;

(15) AH (aromatic hydrocarbon)-based fungicides: biphenyl, chloroneb, dicloran, quintozene, tecnazene, tructophos methyl, and the like;

(16) MBI-R-based fungicides: fthalide, pyroquilon, triclazole, and the like;

(17) MBI-D-based fungicides: carpropamide, diclocymet, fenoxanil, and the like;

(18) SBI-based fungicides: fenhexamid, pyributicarb, terbinafine, and the like;

(19) Phenylurea-based fungicides: pencycuron, and the like;

(20) QiI-based fungicides (Qi inhibitors): cyazofamid, and the like;

(21) Benzamide-based fungicides: zoxamide, and the like;

(22) Enopyranuron-based fungicides: blasticidin, mildiomycin, and the like;

(23) Hexopyranosil-based fungicides: kasugamycin, and the like;

(24) Glucopyranosil-based fungicides: streptomycin, validamycin, and the like;

(25) Cyanoacetoamide-based fungicides: cymoxanil, and the like;

(26) Carbamate-based fungicides: iodocarb, propamocarb, prothiocarb, polycarbamate, and the like;

(27) Uncoupling agent-based fungicides: binapacryl, dinocap, ferimzone, fluazinam, and the like;

(28) Organic tin compound-based fungicides: triphenyltin acetate, triphenyltin chloride, triphenyltin hydroxide, and the like;

(29) Phosphoric acid esters: phosphorous acid, tolclophos-methyl, fosetyl, and the like;

(30) Phthalamic acid-based fungicides: tecloftalam, and the like;

(31) Benzotriazine-based fungicides: triazoxide, and the like;

(32) Benzenesulfonamide-based fungicides: flusulfamide, and the like;

(33) Pyridazinone-based fungicides: diclomezine, and the like;

(34) CAA (carbonic acid amide)-based fungicides, and the like: dimethomorph, flumorph, benthiavalicarb, iprovalicarb, mandipropamide, and the like;

(35) Tetracycline-based fungicides: oxytetracycline, and the like;

(36) Thiocarbamate-based fungicides: metasulfocarb, and the like;

(37) Other compounds: etridiazole, polyoxin, oxolinic acid, hydroxyisoxazole, octinolin, silthiofam, diflumetorim, acibenzolar-S-methyl, probenazole, tiadinil, etapoxam, cyflufenamid, proquinazid, metrafenone, fluopicolid, cupric hydroxide, organic copper, sulfur, ferbam, manzeb, maneb, metiram, propineb, thiuram, zineb, ziram, captan, captafol, folpet, chlorothalonil, dichlofluanid, tolylfluanid, dodine, guazatine, iminoctadine acetate, iminoctaddne dodecylbenzenesulfonate, anilazine, dithianon, chloropicrin, dazomet, qinomethionate, cyprofuram, silthiofam, *agrobacterium*, fluoroimide, and the like.

Insecticides/Acaricides, Nematocides, Soil Disease Control Agents, Anthelmintic Agents:

(1) Organic (thio)phosphate-based agents: acephate, azamethiphos, azinphos-methyl, azinphos-ethyl, bromophos-ethyl, bromphenvinphos, BRP, chlorpyriphos, chlorpyriphos-methyl, chlorpyriphos-ethyl, chlorfenvinphos, cadusaphos, carbophenothion, chlorethoxyfos, chlormephos, coumaphos, cyanofenphos, cyanophos, CYAP, diazinon, dichlorvos, dicrotophos, dimethoate, disulfoton, dimeton-S-methyl, dimethylvinphos, dimeton-S-methylsulfone, dialifos, diazinon, dichlofenthion, dioxabenzofos, disulfoton, ethion, ethoprophos, etrimfos, EPN, fenamiphos, fenitrothion, fenthion, fensulfothion, flupyrazophos, fonofos, formothion, fosmetilan, heptenophos, isazofos, iodofenphos, isofenphos, isoxathion, iprobenfos, malathion, mevinphos, metamidophos, methidathion, monocrotophos, mecarbam, methacrifos, naled, omethoate, oxydemeton-methyl, paraoxon, parathion, parathion-methyl, phenthoate, phosalone, phosmet, phosfamid, phorate, phoxim, pirimiphos-methyl, pirimiphos-ethyl, profenofos, prothiofos, fosthiazate, phosphocarb, propaphos, propetamphos, prothoate, pyridafenthion, pyraclofos, quinalphos, salithion, sulprofos, sulfotep, tetrachlorovinphos, terbufos, triazophos, trichlorfon, tebupirimphos, temephos, thiometon, vamidothion;

(2) Carbamate-based agents: alanycarb, aldicarb, bendiocarb, benfuracarb, carbaryl, carbofuran, carbosulfan, fenoxycarb, fenothiocarb, methiocarb, methomyl, oxamyl, pirimicarb, propoxur, thiodicarb, triazamate, ethiophencarb, fenobucarb, MIPC, MPMC, MTMC, pyridafenthion, furathiocarb, XMC, aldoxycarb, allyxycarb, aminocarb, bendiocarb, bufencarb, butacarb, butocarboxim, butoxycarboxim, cloethocarb, dimetilan, formetanate, isoprocarb, metam sodium, metolcarb, promecarb, thiofanox, trimetacarb, xylylcarb;

(3) Pyrethroid-based agents: allethrin, bifenthrin, cyfluthrin, beta-cyfluthrin, cyhalothrin, lambda-cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, permethrin, prallethrin, pyrethrin, pyrethrin I, pyrethrin II, resmethrin, silafluofen, fluvalinate, tefluthrin, tetramethrin, tralomethrin, transfluthrin, profluthrin, dimefluthrin, acrinathrin, cycloprothrin, halfenprox, flucythrinate, bioallethrin, bioethanomethrin, biopermethrin, bioresmethrin, transpermethrin, empenthrin, fenfluthrin, fenpyrithrin, flubrocythrinate, flufenprox, flumethrin, metofluthrin, phenothirin, protrifenbute, pyresmethrin, tarellethin;

(4) Growth regulators:

(a) Chitin synthesis inhibitors: chlorfluazuron, diflubenzuron, flucycloxuron, flufenoxuron, hexaflumuron, lufenuron, novaluron, teflubenzuron, triflumuron, bistrifluoron, noviflumuron, buprofezine, hexythiazox, etoxazole, clofentezine, fluazuron, penfluoron;

(b) Ecdysone agonists: halofenozide, methoxyfenozide, tebufenozide, chromafenozide, azadirachtin;

(c) Juvenile hormone mimics: pyriproxyfen, methoprene, diofenolan, epofenonate, hydroprene, kinoprene, triprene;

(d) Lipid synthesis inhibitors: spirodiclofen, spiromesifen, spirotetramat, flonicamid;

(5) Nicotine receptor agonists/antagonists: acetamiprid, clothianidin, dinotefuran, imidacloprid, nitenpyram, thiacloprid, thiamethoxam, nithiazine, nicotine, bensultap, cartap, flupyradifurone;

(6) GABA antagonist compounds:

(a) acetoprole, ethiprole, fipronil, vaniliprole, pyrafluoprole, pyriprole;

(b) organic chlorine-based compounds: camphlechlor, chlordane, endosulfan, HCH, γ-HCH, heptachlor, methoxychlor;

(7) Macrocyclic lactone insecticides: abamectin, emamectin benzoate, milbemectin, lepimectin, spinosad, ivermectin, selamectin, doramectin, eprinomectin, moxidectin;

(8) METI I compounds: fenazaquin, pyridaben, tebufenpyrad, tolfenpyrad, flufenerim, hydramethylnon, fenpyroximate, pyrimidifen, dicofol;

(9) METI II and III compounds: acequinocyl, fluacrypyrim, rotenone;

(10) Uncoupling agent compounds: chlorfenapyr, binapacryl, dinobuton, dinocap, DNOC;

(11) Oxidative phosphorylation inhibitor compounds: cyhexatin, diafenthiuron, fenbutatin oxide, propargite azocyclotin;

(12) Molting disrupting compounds: cyromazine;

(13) Mixed function oxidase inhibitor compounds: piperonyl butoxide;

(14) Sodium channel blocking compound: indoxacarb, metaflumizone;

(15) Microbial pesticides: BT agents, insect pathogenic viral agents, insect pathogenic fungal agents, nematode pathogenic fungal agents; *Bacillus* species, *Beauveria bassiana, Metarhizium anisopliae, Paecilomyces* species, *thuringiensin, Verticillium* species;

(16) Latrophilin receptor agonists: depsipeptide, cyclic depsipeptide, 24-membered cyclic depsipeptide, emodepside;

(18) Octopaminergic agonists: amitraz;

(19) Ryanodine derivative agonists: flubendiamide, chlorantraniliprole, cyantraniliprole;

(20) Magnesium-stimulated ATPase inhibitors: thiocyclam, thiosultap, nereistoxin;

(21) Ingestion inhibitors: pymetrozine;

(22) Mite growth inhibitors: clofentezine, ethoxazole;

(23) Others: benclothiaz, bifenazate, pyridalyl, sulfur, cyenopyrafen, cyflumetofen, amidoflumet, tetradifon, chlordimeform, 1,3-dichloropropene, DCIP, fenisobromolate, benzomate, metaldehyde, spinetoram, pyrifluguinazon, benzoximate, bromopropylate, quinomethionate, chlorobenzilate, chloropicrin, clothiazoben, dicyclanil, fenoxacrim, fentrifanil, flubenzimine, fluphenzine, gossyplure, japonilure, metoxadiazone, petroleum, potassium oleate, sulfluramid, tetrasul, triaracene;

(24) Anthelmintic agents (a) Benzimidazole-based agents: fenbendazole, albendazole, triclabendazole, oxybendazole;

(b) Salicylanilide-based agents: closantel, oxyclozanid;

(c) Substituted phenol-based agents: nitroxinil;

(d) Pyrmidine-based agents: pyrantel;

(e) Imidazothiazole-based agents: levamisole;

(f) Tetrahydropyrmidine-based agents: praziquantel;

(g) Other anthelmintic agents: cyclodiene, ryania, clorsulon, metronidazole;

Plant Growth. Regulators

Abscisic acid, indole butyric acid, uniconazole, ethychlozate, ethephon, cloxyfonac, chlormequat, *chlorella* extract, calcium peroxide, cyanamide, dichlorprop, gibberellin, daminozide, decyl alcohol, trinexapac-ethyl, mepiquat chloride, paclobutrazol, paraffin wax, piperonylbutoxide, pyraflufen-ethyl, flurprimidol, prohydrojasmon, prohexadione calcium salt, benzylaminopurine, pendimethalin, forchlorfenuron, potassium hydrazide maleate, 1-naphthylacetoamide, 4-CPA, MCPB, choline, oxyquinoline sulfate, ethychlozate, butralin, 1-methylcyclopropene, and aviglycine hydrochloride.

EXAMPLES

Although the following provides a more detailed explanation of the present invention by indicating examples thereof, the present invention is not limited to the following examples.

Example 1

Synthesis of 3-(2-cyano-pyridin-3-yloxy)-8-fluoro-2-methylquinoline

[Chemical Formula 28]

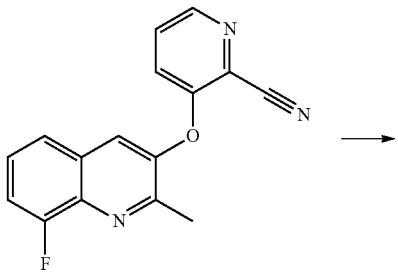

4.9 g of 8-fluoro-3-hydroxy-2-methylquinoline, 3.2 g of 3-chloro-2-cyanopyridine and 3.8 g of potassium carbonate were dissolved in 20 ml of N-methylpyrrolidone followed by stirring for 3 hours at 130° C. Subsequently, the reaction solution was cooled to room temperature followed by addition of water and extraction with ethyl acetate. The extract was washed with saturated saline and dried with magnesium sulfate followed by distilling off the solvent under reduced pressure. The resulting residue was purified by silica gel column chromatography to obtain 5.37 g of 3-(2-cyano-pyridin-3-yloxy)-8-fluoro-2-methylquinoline.

Example 2

Synthesis of 1-[3-(2-methyl-8-fluoroquinolin-3-yloxy)-pyridin-2-yl]-ethanone (Compound No. a-9)

[Chemical Formula 29]

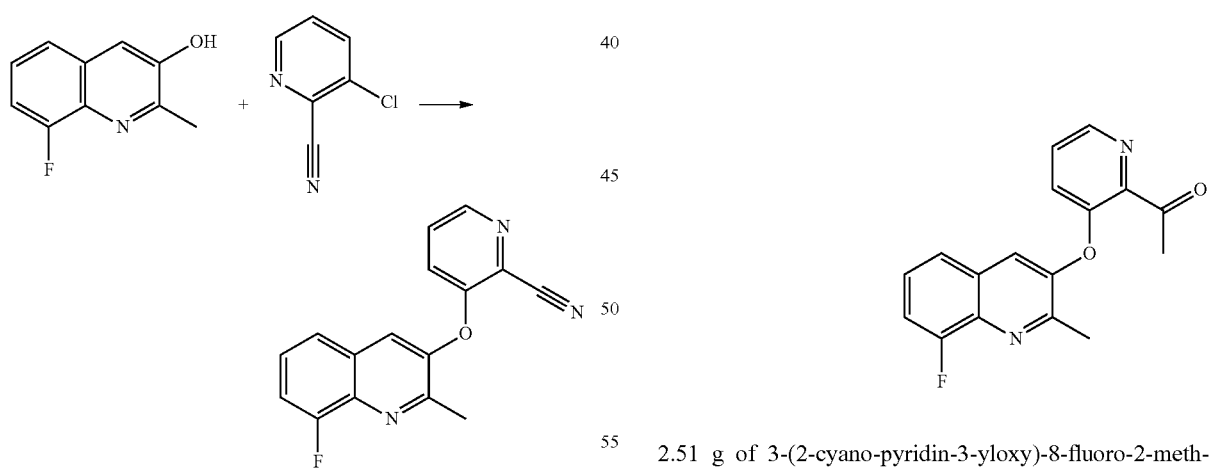

2.51 g of 3-(2-cyano-pyridin-3-yloxy)-8-fluoro-2-methylquinoline were dissolved in 30 ml of dehydrated tetrahydrofuran. 3.6 ml of a 3 M tetrahydrofuran solution of methylmagnesium chloride were dropped therein while cooling with ice followed by stirring the reaction solution for 2 hours while continuing to cool with ice. Subsequently, the reaction solution was added to 1 N hydrochloric acid solution followed by neutralizing with aqueous sodium bicarbonate and then extracting with ethyl acetate. The extract was washed with saturated saline and dried with magnesium sulfate followed by distilling off the solvent under reduced pressure. The resulting residue was purified by silica gel column chromatography to obtain 1.7 g of 1-[3-(2-methyl-8-fluoroquinolin-3-yloxy)-pyridin-2-yl]-ethanone.

Example 3

Synthesis of 2-[(8-fluoro-2-methylquinolin-3-yloxy)pyridine-2-yl]propan-2-ol (Compound No. a-7)

[Chemical Formula 30]

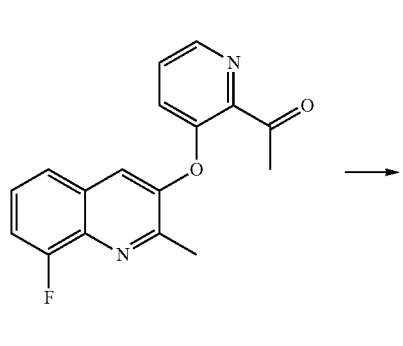

1.58 g of 1-[3-(2-methyl-8-fluoroquinolin-3-yloxy)-pyridin-2-yl]-ethanone were dissolved in 20 ml of dehydrated tetrahydrofuran. 2.7 ml of a 3 M tetrahydrofuran solution of methylmagnesium chloride were dropped therein while cooling with ice followed by stirring the reaction solution for 3 hours while continuing to cool with ice. Subsequently, the reaction solution was added to 1 N hydrochloric acid solution followed by neutralizing with aqueous sodium bicarbonate and then extracting with ethyl acetate. The extract was washed with saturated saline and dried with magnesium sulfate followed by distilling off the solvent under reduced pressure. The resulting residue was purified by silica gel column chromatography to obtain 1.69 g of 2-[(8-fluoro-2-methylquinolin-3-yloxy)pyridin-2-yl]propan-2-ol.

Example 4

Synthesis of 3-[2-(2-methoxy-2-propyl)pyridin-3-yloxy]-8-fluoro-2-methylquinoline (Compound No. a-16)

[Chemical Formula 31]

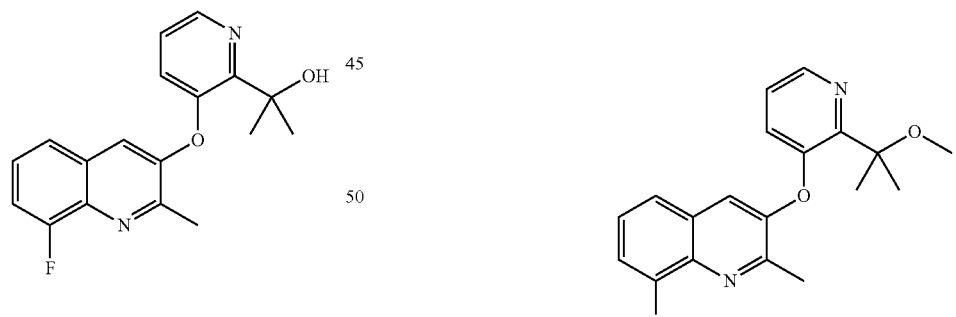

0.50 g of 2-[(8-fluoro-2-methylquinolin-3-yloxy)pyridin-2-yl]propan-2-ol and 0.45 g of methyl iodide were dissolved in 10 ml of dimethylformamide. 64 mg of sodium hydride (60% oil suspension) were added thereto while cooling with ice followed by stirring the reaction solution for 2 hours while continuing to cool with ice. Subsequently, the reaction solution was poured in ice water followed by extraction with ethyl acetate. The extract was washed with saturated saline and dried with magnesium sulfate followed by distilling off the solvent under reduced pressure. The resulting residue was purified by silica gel column chromatography to obtain 0.15 g of 3-[2-(2-methoxy-2-propyl)pyridin-3-yloxy]-8-fluoro-2-methylquinoline.

Example 5

Synthesis of 3-[2-(2-ethoxy-2-propyl)pyridin-3-yloxy]-8-fluoro-2-methylquinoline (Compound No. a-56)

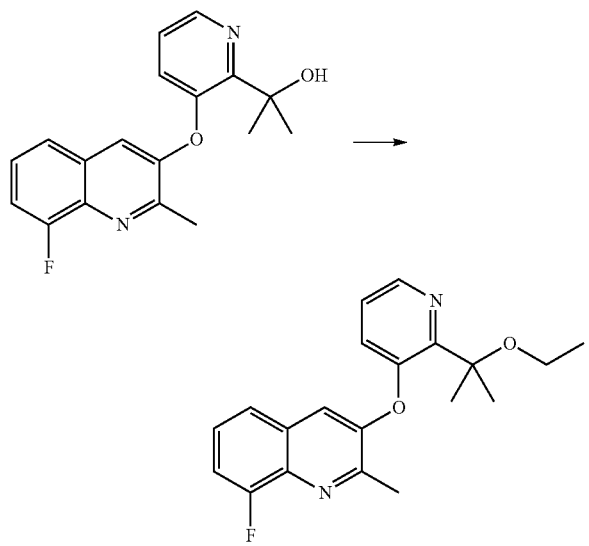

[Chemical Formula 32]

0.53 g of 2-[(8-fluoro-2-methylquinolin-3-yloxy)pyridin-2-yl]propan-2-ol were dissolved in 10 ml of chloroform. 0.61 g of thionyl chloride were added thereto at room temperature followed by stirring for 30 minutes at room temperature. Subsequently, the solvent and excess thionyl chloride were distilled off under reduced pressure, and then the residue was dissolved in ethanol, followed by refluxing for 1 hour. Subsequently, the reaction solution was concentrated under reduced pressure and water was added to the residue followed by extracting with ethyl acetate. The extract was washed with saturated saline and dried with magnesium sulfate followed by distilling off the solvent under reduced pressure. The resulting residue was purified by silica gel column chromatography to obtain 0.19 g of 3-[2-(2-ethoxy-2-propyl)pyridin-3-yloxy]-8-fluoro-2-methylquinoline.

Example 6

Synthesis of 2-[3-(8-fluoro-quinolin-3-yloxy)-pyridin-2-yl]-2-methylpropionitrile (Compound No. a-11)

Step 1) Synthesis of 2-(3-bromo-pyridin-2-yl)-2-methyl-propionitrile 2.25 g of (3-bromo-pyridin-2-yl)-acetonitrile were dissolved in 30 ml of dimethylformamide. 1.09 g of sodium hydride (60% oil suspension) were added thereto at 0° C. Continuing, 3.9 g of methyl iodide were added to the reaction solution followed by stirring for 1.5 hours. Subsequently, dilute hydrochloric acid was added followed by extracting with ethyl acetate. The solvent of the organic layer was distilled off followed by purification with silica gel column chromatography to obtain 2.68 g of 2-(3-bromo-pyridin-2-yl)-2-methyl-propionitrile.

Step 2) Synthesis of 2-[3-(8-fluoro-quinolin-3-yloxy)-pyridin-2-yl]-2-methylpropionitrile

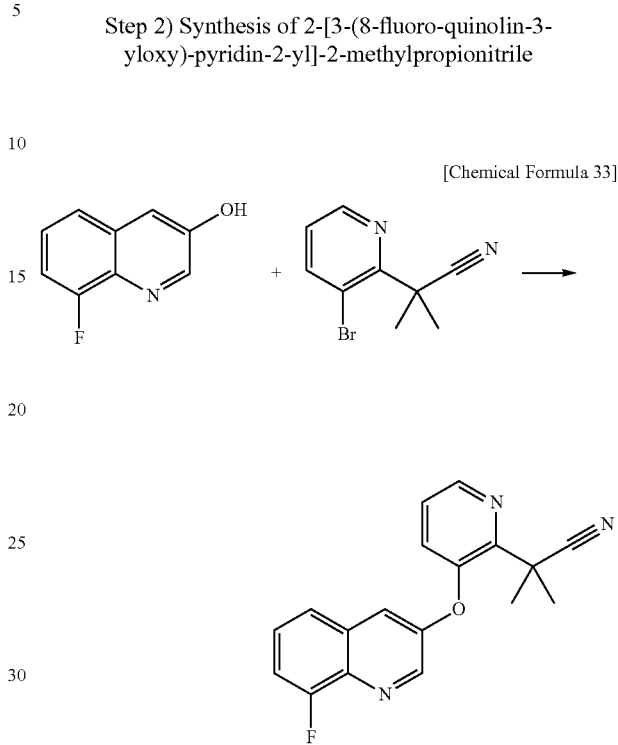

[Chemical Formula 33]

1.35 g of 2-(3-bromo-pyridin-2-yl)-2-methyl-propionitrile were dissolved in 6 ml of N-methylpyrrolidone. 0.82 g of 8-fluoro-3-hydroxyquinoline, 1.95 g of cesium carbonate, 0.18 g of dipivaloylmethane and 0.50 g of copper (I) chloride were added thereto followed by stirring for 23 hours at 130° C. Subsequently, the reaction mixture was cooled to room temperature and purified by silica gel column chromatography to obtain 0.46 g of 2-[3-(8-fluoro-quinolin-3-yloxy)-pyridin-2-yl]-2-methylpropionitrile.

Example 7

Synthesis of 2-[3-(8-fluoro-quinolin-3-yloxy)-pyridin-2-yl]-2-methylpropionic acid ethyl ester (Compound No. a-12)

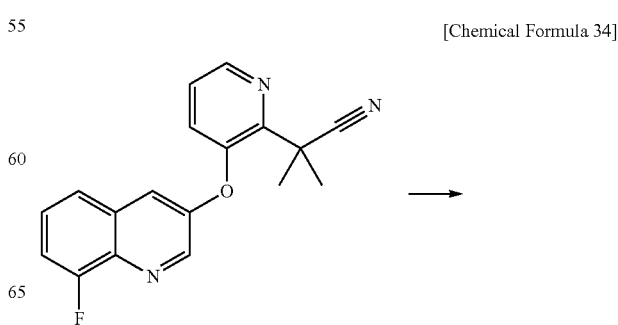

[Chemical Formula 34]

-continued

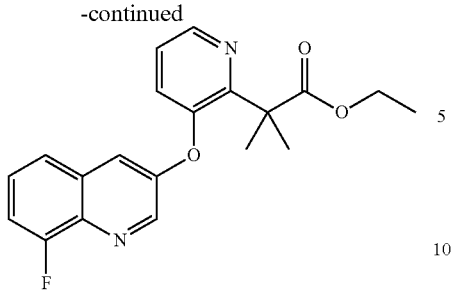

2 ml of ethanol and 2 ml of concentrated sulfuric acid were added to 0.38 g of 2-[3-(8-fluoro-quinolin-3-yloxy)-pyridin-2-yl]-2-methylpropionitrile. The mixture was stirred for 6 hours at 100° C. Subsequently, saturated aqueous sodium hydrogen carbonate solution was added thereto to stop the reaction. The resultant was then extracted with ethyl acetate followed by distilling off the solvent of the organic layer. Subsequently, the resultant was purified by silica gel column chromatography to obtain 0.24 g of 2-[3-(8-fluoro-quinolin-3-yloxy)-pyridin-2-yl]-2-methylpropionic acid ethyl ester.

Example 8

Synthesis of 2-[3-(8-fluoro-quinolin-3-yloxy)-pyridin-2-yl]-2-methylpropionic acid (Compound No. a-19)

[Chemical Formula 35]

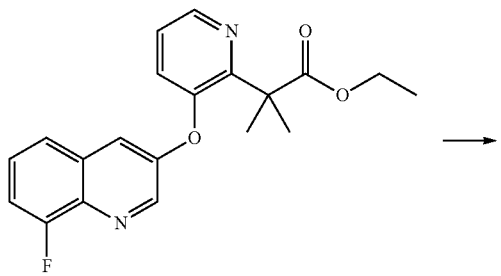

0.33 g of 2-[3-(8-fluoro-quinolin-3-yloxy)-pyridin-2-yl]-2-methylpropionic acid ethyl ester were dissolved in 1 ml of ethanol. 2 ml of 4N aqueous sodium hydroxide solution were added thereto followed by heating to reflux for 48 hours. Subsequently, dilute hydrochloric acid was added thereto followed by extracting with ethyl acetate and distilling off the solvent of the organic layer to obtain 0.25 g of 2-[3-(8-fluoro-quinolin-3-yloxy)-pyridin-2-yl]-2-methylpropionic acid.

Example 9

Synthesis of N-ethyl-2-[3-(8-fluoro-quinolin-3-yloxy)-pyridin-2-yl]-isobutylamide (Compound No. a-55)

[Chemical Formula 36]

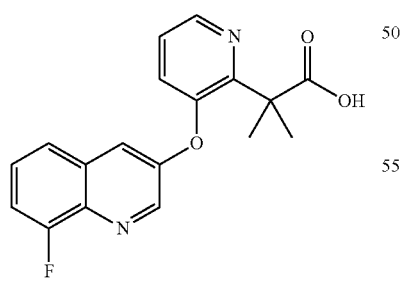

0.10 g of 2-[3-(8-fluoro-quinolin-3-yloxy)-pyridin-2-yl]-2-methylpropionic acid and 0.08 g of diisopropylethylamine were dissolved in 1.2 ml of dimethylformamide. 0.3 ml of a 2.0 M tetrahydrofuran solution of ethylamine and 0.17 g of 0-(benzotriazol-1-yl)-N,N,N',N'-tetramethyluronium hexafluorophosphate were added thereto followed by stirring for 14 hours at room temperature. Subsequently, the reaction solution was extracted with ethyl acetate followed by distilling off the solvent of the organic layer. The resultant was then purified by silica gel column chromatography to obtain 0.10 g of N-ethyl-2-[3-(8-fluoro-quinolin-3-yloxy)-pyridin-2-yl]-isobutylamide.

Example 10

Synthesis of 2-[3-(8-fluoro-quinolin-3-yloxy)-pyridin-2-yl]-2-methyl-propioaldehyde (Compound No. a-21)

Step 1) Synthesis of 2-(3-bromo-pyridin-2-yl)-2-methyl-propioaldehyde 1.8 g of 2-(3-bromo-pyridin-2-yl)-2-methyl-propionitrile were dissolved in 20 ml of toluene. 5.9 ml of a 25% by weight toluene solution of diisobutylaluminum hydride were added thereto at 0° C. The mixture was stirred for 17 hours at room temperature. Subsequently, dilute hydrochloric acid was added thereto to dissolve the unreacted diisobutylaluminum hydride. Continuing, aqueous saturated sodium hydrogen carbonate solution was added thereto followed by extracting with ethyl acetate. The solvent of the organic phase was distilled off followed by purifying by silica gel column chromatography to obtain 0.44 g of 2-(3-bromo-pyridin-2-yl)-2-methyl-propioaldehyde.

Step 2) Synthesis of 2-[3-(8-fluoro-quinolin-3-yloxy)-pyridin-2-yl]-2-methyl-propioaldehyde

[Chemical Formula 37]

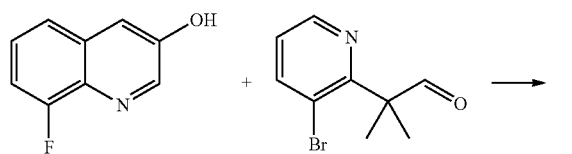

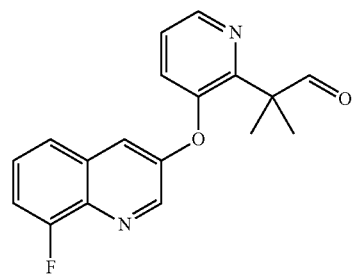

0.41 g of 2-(3-bromo-pyridin-2-yl)-2-methyl-propioaldehyde were dissolved in 4 ml of N-methylpyrrolidone. 0.59 g of 8-fluoro-3-hydroxyquinoline, 1.2 g of cesium carbonate, 0.07 g of dipivaloylmethane and 0.18 g of copper (I) chloride were added thereto followed by stirring for 16 hours at 130° C. Subsequently, the reaction solution was cooled to room temperature and purified by silica gel column chromatography to obtain 0.19 g of 2-[3-(8-fluoro-quinolin-3-yloxy)-pyridin-2-yl]-2-methyl-propioaldehyde.

Example 11

Synthesis of 3-[3-(8-fluoro-quinolin-3-yloxy)-pyridin-2-yl]-3-methyl-butan-2-ol

[Chemical Formula 38]

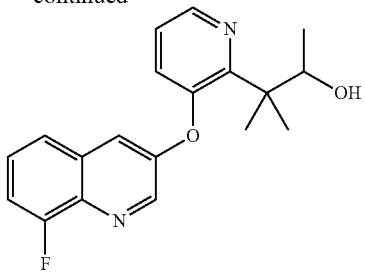

0.10 g of 2-[3-(8-fluoro-quinolin-3-yloxy)-pyridin-2-yl]-2-methyl-propioaldehyde were dissolved in 3 ml of tetrahydrofuran. 0.2 ml of a 3.0 M tetrahydrofuran solution of methylmagnesium chloride were added thereto followed by stirring for 30 minutes at 0° C. Subsequently, water was added thereto to stop the reaction. The resultant was then extracted with ethyl acetate followed by distilling off the solvent of the organic layer and purifying by silica gel column chromatography to obtain 0.07 g of 3-[3-(8-fluoro-quinolin-3-yloxy)-pyridin-2-yl]-3-methyl-butan-2-ol.

Example 12

Synthesis of 3-[3-(8-fluoro-quinolin-3-yloxy)-pyridin-2-yl]-3-methyl-butan-2-one (Compound No. a-15)

[Chemical Formula 39]

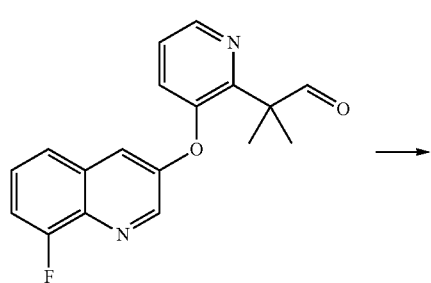

0.07 g of 3-[3-(8-fluoro-quinolin-3-yloxy)-pyridin-2-yl]-3-methyl-butan-2-ol were dissolved in 3 ml of dichloromethane. 0.27 g of Dess-Martin reagent were added thereto at 0° C. followed by stirring for 30 minutes. Subsequently, the reaction solution was concentrated followed by purifying by silica gel column chromatography to obtain 0.04 g of 3-[3-(8-fluoro-quinolin-3-yloxy)-pyridin-2-yl]-3-methyl-butan-2-one.

Although the following provides a more detailed explanation of production intermediates of the compound according to the present invention using reference examples, the production intermediates are not limited to the following reference examples.

Reference Example 1

Synthesis of 7,8-difluoro-3-hydroxy-2-methylquinoline

Step 1) Synthesis of 6,7-difluoroisatin

[Chemical Formula 40]

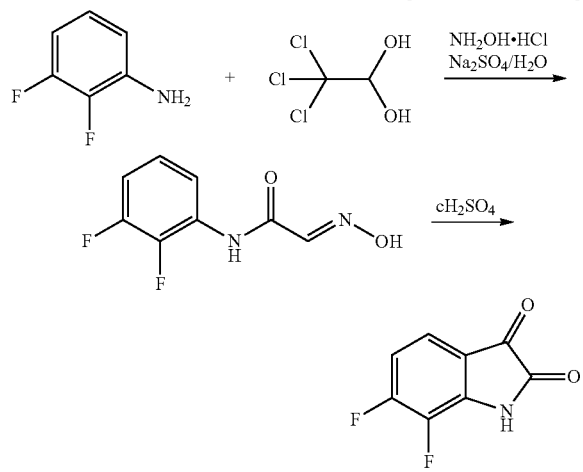

15.7 g of 2,3-difluoroaniline were added to 825 ml of water followed by adding 24.2 g of trichloroacetaldehyde, 30.8 g of hydroxyamine hydrochloride and 138.6 g of anhydrous sodium sulfate and stirring the mixture for 10 hours at 50° C. After allowing to cool to room temperature, 44 mL of 2N hydrochloric acid were added thereto, followed by stirring the mixture for 30 minutes. Subsequently, crystals were removed by filtration. The resulting crystals were dried, and then added to hot concentrated sulfuric acid at 70° C., followed by stirring the mixture for 1 hour at 80° C. to 90° C. The reaction solution was then poured over ice and extracted with ethyl acetate. The organic layer was washed with saturated saline and dried with magnesium sulfate followed by distilling off the solvent under reduced pressure to obtain 26 g of a crude product of 6,7-difluoroisatin.

Step 2) Synthesis of 7,8-difluoro-3-hydroxy-2-methylquinoline

[Chemical Formula 41]

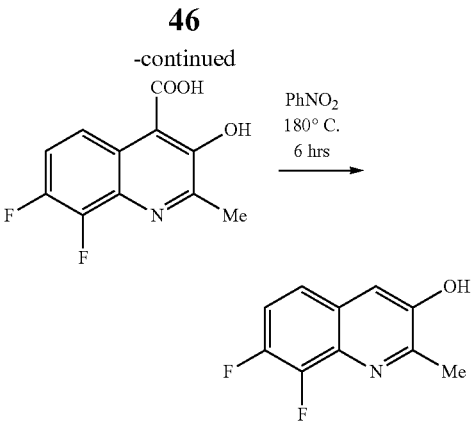

41 g of the crude product of 6,7-difluoroisatin were added to 200 mL of water followed the addition of 75.3 g (6 equivalents) of potassium hydroxide while cooling with ice and stirring the mixture for 30 minutes. 42 g (1.4 equivalents) of bromoacetophenone were dropped into the resultant suspension at a temperature of 20° C. to 25° C. Following completion of dropping, the reaction mixture was stirred overnight at room temperature. The resultant was then neutralized with concentrated hydrochloric acid. The precipitated crystals were removed by filtration and washed with a small amount of water. The resulting crystals were dried, and then added to 100 mL of nitrobenzene a little at a time at 130° C. to 140° C. Following completion of addition, the reaction mixture was stirred for 1 hour at 150° C. After cooling the reaction mixture to room temperature, the precipitated crystals were washed with chloroform to obtain 26.3 g of 7,8-difluoro-3-hydroxy-2-methylquinoline.

The results of NMR analysis of the product were as indicated below.

$^1$H-NMR (300 MHz, DMSO-d6) δ2.57 (s, 3H), 7.4-7.7 (m, 3H), 10.60 (bs, 1H)

8-fluoro-3-hydroxy-2-methylquinoline was produced according to the same method.

The results of NMR analysis of the product were as indicated below.

$^1$H-NMR (300 MHz, DMSO-d6) δ2.56 (s, 3H), 7.2-7.6 (m, 4H), 10.53 (bs, 1H)

Reference Example 2

Synthesis of 7,8-difluoro-3-hydroxyquinoline

Step 1) Synthesis of 7,8-difluoroquinoline

[Chemical Formula 42]

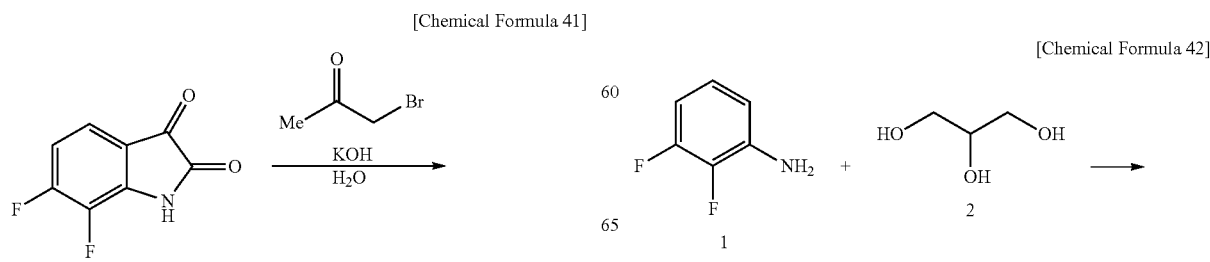

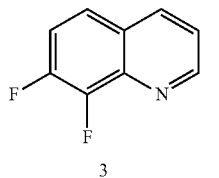

3

607.7 g (49.57 mol) of 80% sulfuric acid were placed in a 3 L eggplant flask containing a stirrer followed by cooling to 0° C. 160.0 g (1.24 mol) of 2,3-difluoroaniline were gradually added thereto. Following completion of addition, the reaction mixture was stirred for 1 hour at room temperature. 1.85 g (12.3 mmol) of sodium iodide were then added thereto followed by heating with an oil bath at 150° C. When the liquid temperature reached 150° C., 125.5 g (1.36 mol) of glycerin were dropped therein over the course of 1 hour. Following completion of dropping, the reaction mixture was stirred for 1 hour at 150° C. Next, the temperature of the oil bath was raised to 180° C. Water was distilled off over the course of 2 hours using a distillation apparatus. After confirming elimination of the raw materials, the reaction mixture was neutralized with 10 N aqueous sodium hydroxide solution while cooling in an ice water bath (internal temperature: 60° C. to 70° C.). Following neutralization, the reaction mixture was extracted with ethyl acetate before the internal temperature returned to room temperature, and then the extract was dried with magnesium sulfate, filtered, and concentrated. The resulting crude product was purified by silica gel column chromatography (n-hexane:ethyl acetate) to obtain 185.5 g (91%) of 7,8-difluoroquinoline in the form of a light brown solid.

Step 2) Synthesis of 7,8-difluoro-3-iodoquinoline

[Chemical Formula 43]

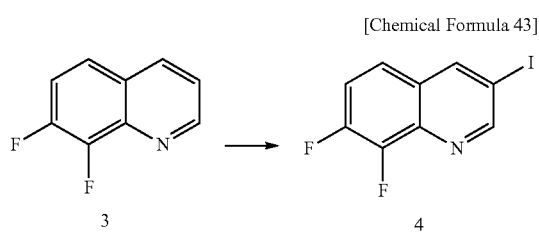 [SMILES: Fc1ccc2cccnc2c1F ; Fc1ccc2cc(I)cnc2c1F]

185.5 g (1.12 mol) of 7,8-difluoroquinoline, 505.4 g (2.25 mol) of N-iodosuccinimide and 927 mL of acetic acid were placed in a 3 L eggplant flask containing a stirrer, followed by stirring the mixture for 30 hours at 90° C. After cooling the resultant, the precipitated crystals were filtered and dried.

The filtrate was concentrated under reduced pressure and the remaining acetic acid was neutralized with sodium hydrogen carbonate followed by extracting with ethyl acetate. The extract was dried with magnesium sulfate, filtered and concentrated. The resulting crude product was purified by silica gel column chromatography (n-hexane:ethyl acetate).

The resultant was combined with the previously obtained crystals to obtain 227.2 g (70%) of 8-difluoro-3-iodoquinoline in the form of a light brown solid.

The results of NMR analysis of the product were as indicated below.

$^1$H-NMR (300 MHz, CDCl3) δ7.39-7.51 (m, 2H), 8.55 (m, 1H), 9.08 (d, 1H, J=2.1 Hz)

Step 3) Synthesis of 7,8-difluoro-3-hydroxyquinoline

[Chemical Formula 44]

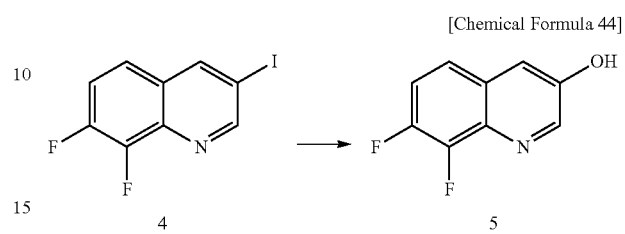

227.2 g (0.78 mol) of 7,8-difluoro-3-iodoquinoline, 600 mL of dimethylsulfoxide and 600 mL of water were placed in a 3 L eggplant flask, followed by the addition thereto of 131.5 g (2.34 mol) of potassium hydroxide, 14.8 g (0.078 mol) of CuI and 28.1 g (0.156 mol) of 1,10-phenanthroline. The reaction mixture was heated to 100° C. with an oil bath, followed by stirring the mixture for 24 hours. After allowing to cool, ethyl acetate and water were added thereto followed by removal of the organic layer. The resulting aqueous layer was neutralized with concentrated hydrochloric acid. The precipitated crystals were filtered and dried.

The filtrate was extracted with ethyl acetate followed by drying with magnesium sulfate, filtering and concentrating. The resulting crude product was purified by silica gel column chromatography (n-hexane:ethyl acetate).

The resultant was combined with the previously obtained crystals to obtain 133.7 g (95%) of 7,8-difluoro-3-hydroxyquinoline in the form of a light brown solid.

The results of NMR analysis of the product were as indicated below.

$^1$H-NMR (300 MHz, CD3OD) δ7.39-7.60 (m, 3H), 8.59 (d, 1H, J=2.4 Hz)

8-fluoro-3-hydroxyquinoline was produced according to the same method. The results of NMR analysis of the product were as indicated below.

$^1$H-NMR (300 MHz, CDCl3) δ7.16 (m, 1H), 7.34-7.49 (m, 3H), 8.71 (d, 1H, J=2.7 Hz), 9.90 (bs, 1H)

Reference Example 3

Synthesis of 7-fluoro-3-hydroxy-2-methylquinoline

Step 1) Synthesis of 6-fluoroisatin

[Chemical Formula 45]

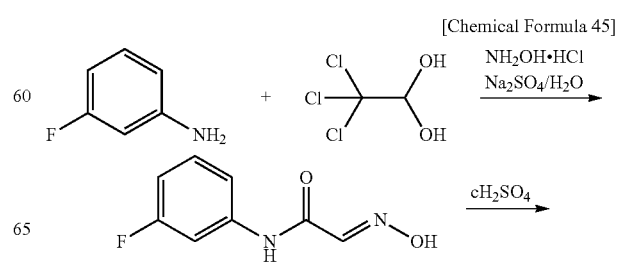

-continued

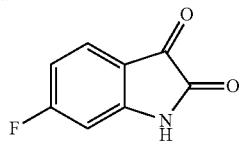

9.6 g of 3-fluoroaniline were added to 590 mL of water followed by the addition of 17.2 g of trichloroacetaldehyde monohydrate, 21.9 g of hydroxyamine hydrochloride and 98.2 g of anhydrous sodium sulfate and stirring the mixture for 5 hours at 50° C. After cooling the resultant to room temperature and allowing to stand overnight, 31 mL of 2 N HCl were added thereto followed by stirring the mixture for 30 minutes and then filtering out the crystals. After drying the resulting crystals, the crystals were added to concentrated sulfuric acid heated to 70° C., followed by stirring the mixture for 1 hour at 80° C. to 90° C. The reaction mixture was poured over ice followed by extracting with ethyl acetate and washing with saturated saline. After drying the organic layer with magnesium sulfate, the solvent was distilled off under reduced pressure to obtain 7.96 g of a crude product of 6-fluoroisatin.

Step 2) Synthesis of 7-fluoro-3-hydroxy-2-methylquinoline

[Chemical Formula 46]

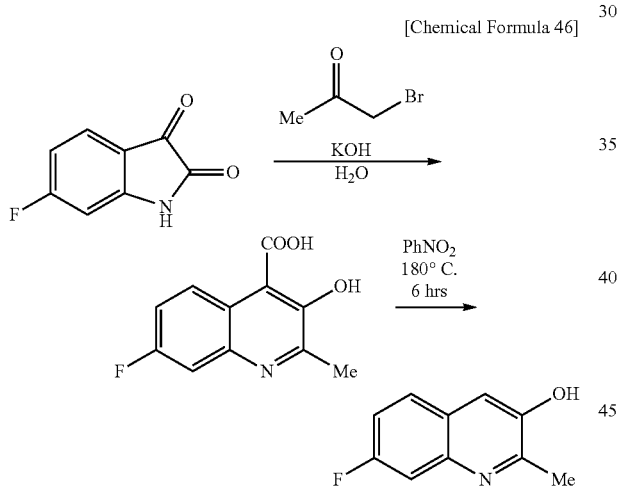

7.96 g of the crude product of 6-fluoroisatin were added to 55 mL of water followed by the addition of 16.2 g (6 equivalents) of KOH while cooling with ice and stirring for 30 minutes. 9.9 g (1.5 equivalents) of bromoacetophenone were dropped into the resultant suspension while holding the internal temperature of the reaction mixture at 20° C. to 25° C. followed by additionally stirring overnight at room temperature. After neutralizing with concentrated hydrochloric acid, the precipitated crystals were filtered out and washed with a small amount of water. After adequately drying the resulting crystals, 70 mL of nitrobenzene heated to 120° C. to 130° C. were added a little at a time followed by further stirring for 1 hour at 140° C. to 150° C. After cooling the reaction mixture to room temperature, the precipitated crystals were washed with chloroform to obtain 5.4 g of 7-fluoro-3-hydroxy-2-methylquinoline.

The results of NMR analysis of the product were as indicated below.

¹H-NMR (300 MHz, DMSO-d6) δ2.56 (s, 3H), 7.32-7.38 (m, 1H), 7.53-7.57 (m, 1H), 7.80-7.84 (m, 1H)

Example 13

Synthesis of 3-[2-fluoro-6-(5-fluoro-quinoxalin-2-yloxy)-phenyl]-3-methyl-butan-2-one

[Chemical Formula 47]

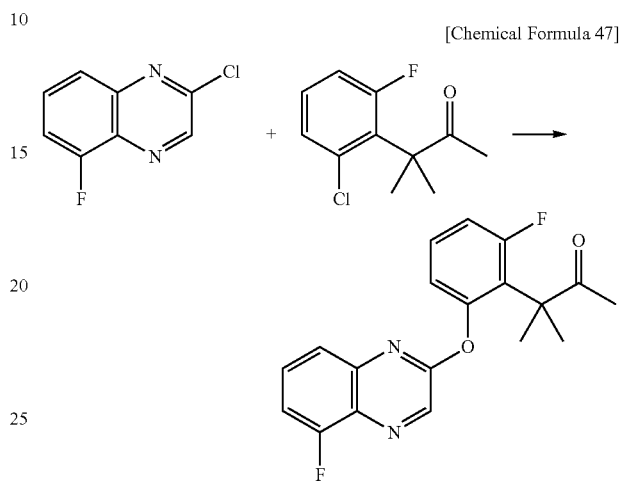

2-chloro-5-fluoro-quinoxaline used as the raw material was synthesized according to the method described in Non-Patent Document 1.

0.32 g of 3-(2-fluoro-6-hydroxy-phenyl)-3-methyl-butan-2-one and 0.28 g of 2-chloro-5-fluoro-quinoxaline were dissolved in 3 ml of dimethylformamide. 0.25 g of potassium carbonate were added thereto followed by stirring for 2 hours at 100° C. Subsequently, the reaction mixture was purified by silica gel column chromatography to obtain 0.14 g of 3-[2-fluoro-6-(5-fluoro-quinoxalin-2-yloxy)-phenyl]-3-methyl-butan-2-one.

Example 14

Synthesis of 2-chloro-6-(5,6,7,8-tetrahydro-quinoxalin-2-yloxy)-benzaldehyde

[Chemical Formula 48]

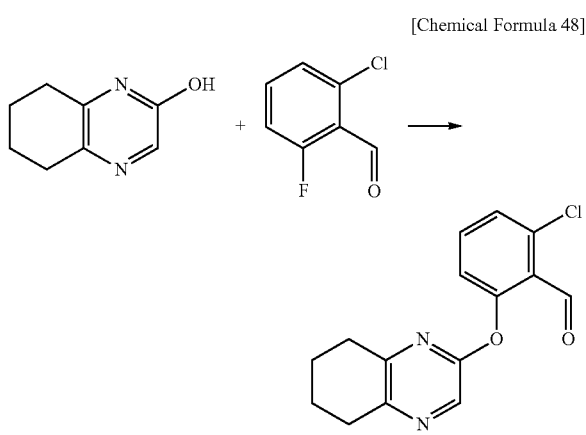

The tetrahydroquinoxalone used as the raw material was synthesized according to the method described in Patent Document 5.

0.3 g of 5,6,7,8-tetrahydroquinoxalin-2-ol were dissolved in 5 ml of dimethylformamide. 0.1 g of sodium hydride were added thereto. 0.35 g of 2-chloro-6-fluoro-benzaldehyde were added to the reaction solution followed by stirring for 3 hours at 100° C. 1 N hydrochloric acid was then added to the reaction solution. Subsequently, the reaction solution was extracted with ethyl acetate and the organic layer was concentrated followed by purifying by silica gel column chromatography to obtain 0.26 g of 2-chloro-6-(5,6,7,8-tetrahydroquinoxalin-2-yloxy)-benzaldehyde.

Example 15

Synthesis of 5,6-difluoro-2-[2-(1-methoxy-1-methyl-ethyl)-pyridin-3-yloxy]-3-methyl-quinoxaline

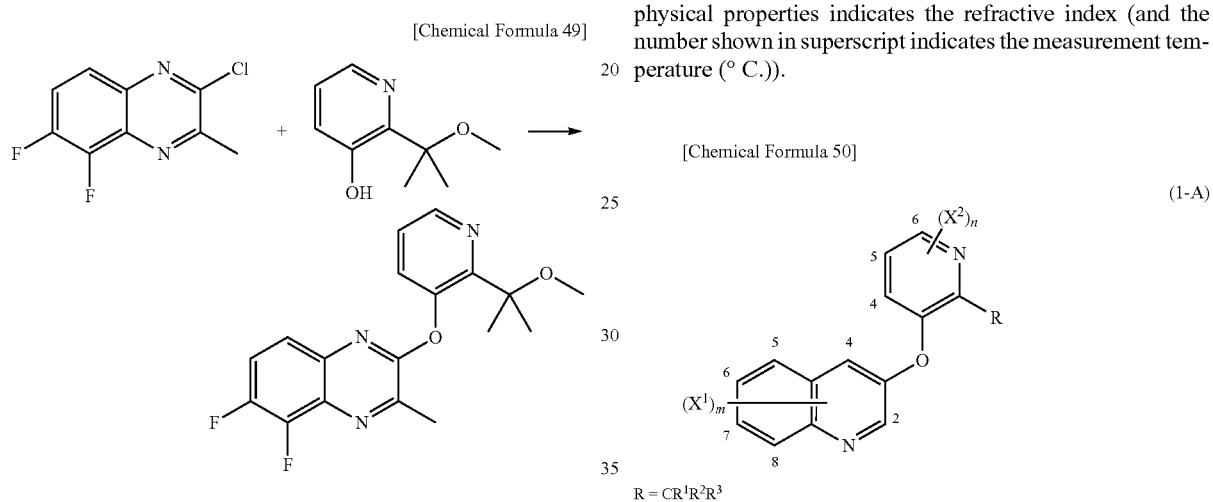

[Chemical Formula 49]

0.17 g of 2-chloro-5,6-difluoro-3-methylquinoxaline were dissolved in 2 mL of N-methylpyrrolidone. 0.13 g of 2-(1-methoxy-1-methyl-ethyl)-pyridin-3-ol and 0.11 g of potassium carbonate were added thereto followed by stirring for 3 hours at 100° C. Subsequently, the reaction solution was purified by silica gel column chromatography to obtain 0.24 g of 5,6-difluoro-2-[2-(1-methoxy-1-methyl-ethyl)-pyridin-3-yloxy]-3-methyl-quinoxaline.

Nitrogenated heterocyclic compounds obtained in the aforementioned examples and nitrogenated heterocyclic compounds synthesized according to methods similar to any of the aforementioned examples are shown in Tables 1 and 2.

In Table 1, $R^1$, $R^2$, $R^3$, $(X^1)_m$ and $(X^2)_n$ represent those groups shown in formula (1-A).

In Table 2, $R^1$, $R^2$, $R^3$, $(X^1)_m$, $A^1$ to $A^4$ and $(X^2)_n$ represent those groups shown in formula (1-B).

In addition, the symbol $n_D$ shown in the column entitled physical properties indicates the refractive index (and the number shown in superscript indicates the measurement temperature (° C.)).

[Chemical Formula 50]

(1-A)

$R = CR^1R^2R^3$

TABLE 1

| Compound No. | $(X^1)_m$ | $R^1$ | $R^2$ | $R^3$ | $(X^2)_n$ | Physical Properties |
|---|---|---|---|---|---|---|
| a-1 | — | | =N | | — | 149-150 |
| a-2 | — | —OH | —CH₃ | —CH₃ | — | * |
| a-3 | 8-F | | =O | —H | — | 138-140 |
| a-4 | 2-$^t$Bu, 8-F | | =O | —H | — | 150-151 |
| a-5 | 8-F | —OH | —H | —$^t$Bu | — | 110-112 |
| a-6 | 8-F | | =O | —$^t$Bu | — | 90-91 |
| a-7 | 2-CH₃, 8-F | —OH | —CH₃ | —CH₃ | — | * |
| a-8 | 8-F | —OH | —CH₃ | —CH₃ | — | * |
| a-9 | 2-CH₃, 8-F | | =O | —CH₃ | — | 133-134 |
| a-10 | 2-CH₃, 8-F | —OH | —CH₃ | —$^t$Bu | — | 133-136 |
| a-11 | 8-F | —CH₃ | —CH₃ | —CN | — | 118-120 |
| a-12 | 8-F | —CH₃ | —CH₃ | —CO₂Et | — | * |
| a-13 | 8-F | —F | —F | —C(CH₃)₂OH | — | |
| a-14 | 8-F | —CH₃ | —CH₃ | —C(CH₃)₂OH | — | 105-107 |
| a-15 | 8-F | —CH₃ | —CH₃ | —COCH₃ | — | 146-148 |
| a-16 | 2-CH₃, 8-F | —OCH₃ | —CH₃ | —CH₃ | — | 105-107 |
| a-17 | 2-CH₃, 8-F | —OCH₂CH=CH₂ | —CH₃ | —CH₃ | — | $n_D^{20.6}$1.574 |
| a-18 | 2-CH₃, 8-F | —OCH₂Ph | —CH₃ | —CH₃ | — | $n_D^{20.6}$1.594 |
| a-19 | 8-F | —CH₃ | —CH₃ | —CO₂H | — | 165-167 |
| a-20 | 8-F | —CH₃ | —CH₃ | —CON(CH₃)OCH₃ | — | * |
| a-21 | 8-F | —CH₃ | —CH₃ | —CHO | — | 105-107 |
| a-22 | 2-CH₃, 8-F | —CH₃ | —CH₃ | —CO₂Et | — | * |
| a-23 | 8-F | —CH₃ | —CH₃ | —CO₂$^i$Pr | — | 93-96 |
| a-24 | 2-CH₃, 8-F | —CH₃ | —CH₃ | —CN | — | 142-144 |
| a-25 | 8-F | —CH₃ | —CH₃ | —CO₂⁻Na⁺ | — | 247-249 |
| a-26 | 7,8-F₂ | | =N | | — | 185-187 |
| a-27 | 7,8-F₂ | | =O | —CH₃ | — | 152-155 |
| a-28 | 7,8-F₂ | —OH | —CH₃ | —CH₃ | — | 100-102 |

TABLE 1-continued

| Compound No. | $(X^1)_m$ | $R^1$ | $R^2$ | $R^3$ | $(X^2)_n$ | Physical Properties |
|---|---|---|---|---|---|---|
| a-29 | 2-CH$_3$, 7,8-F$_2$ | —OH | —CH$_3$ | —CH$_3$ | — | 144-146 |
| a-30 | 2-Et, 7,8-F$_2$ | —OCH$_3$ | —CH$_3$ | —CH$_3$ | — | 95-97 |
| a-31 | 7,8-F$_2$ | —OCH$_3$ | —CH$_3$ | —CH$_3$ | — | 68-71 |
| a-32 | 2-CH$_3$, 7,8-F$_2$ | —OCH$_3$ | —CH$_3$ | —CH$_3$ | — | 114-116 |
| a-33 | 7,8-F$_2$ | —CH$_3$ | —CH$_3$ | —CN | — | * |
| a-34 | 2-CH$_3$, 8-F | —OH | —H | —CH$_3$ | — | 99-101 |
| a-35 | 2-CH$_3$, 8-F | —OCH$_3$ | —H | —CH$_3$ | — | 128-130 |
| a-36 | 2-CH$_3$, 8-F | —OCH$_2$CH=CH$_2$ | —H | —CH$_3$ | — | $n_D^{22.4}$1.576 |
| a-37 | 2-CH$_3$, 8-F | —OCH$_2$CH=C(CH$_3$)$_2$ | —H | —CH$_3$ | — | $n_D^{22.4}$1.5648 |
| a-38 | 2-CH$_3$, 8-F | —OCH$_2$Ph | —H | —CH$_3$ | — | $n_D^{22.6}$1.6084 |
| a-39 | 2-CH$_3$, 8-F | —OCH$_2$Ph | —H | —CH$_3$ | 1-O$^-$ | $n_D^{20.0}$1.626 |
| a-40 | 2-CH$_3$, 8-F | —OH | —CH$_3$ | —Et | — | 115-116 |
| a-41 | 2-CH$_3$, 8-F | =N—OCH$_3$ | | —CH$_3$ | — | 108-109 |
| a-42 | 8-F | —CH$_3$ | —CH$_3$ | —CH$_2$OH | — | 156-158 |
| a-43 | 8-F | —CH$_3$ | —CH$_3$ | —CH(OH)Et | — | * |
| a-44 | 8-F | —CH$_3$ | —CH$_3$ | —CH$_2$OCH$_3$ | — | * |
| a-45 | 8-F | —CH$_3$ | —CH$_3$ | —COEt | — | * |
| a-46 | 8-F | —CH$_3$ | —Et | —CN | — | * |
| a-47 | 8-F | —CH$_3$ | —Ph | —CN | — | 192-194 |
| a-48 | 8-F | —CH$_3$ | —Et | —CO$_2$Et | — | * |
| a-49 | 8-F | —CH$_3$ | —Ph | —CO$_2$Et | — | $n_D^{23.9}$15808 |
| a-50 | 2-CH$_3$, 8-F | —OCH$_3$ | —CH$_3$ | —Et | — | 101-102 |
| a-51 | 2-CH$_3$, 8-F | —OCH$_2$C≡CH | —CH$_3$ | —CH$_3$ | — | 113-115 |
| a-52 | 2-CH$_3$, 8-F | =N—OEt | | —CH$_3$ | — | 112-113 |
| a-53 | 8-OH | —CH$_3$ | —CH$_3$ | —CONHBn | — | 161-163 |
| a-54 | 8-F | —CH$_3$ | —CH$_3$ | —CON(CH$_3$)Et | — | 120-123 |
| a-55 | 8-F | —CH$_3$ | —CH$_3$ | —CONHEt | — | 155-158 |
| a-56 | 2-CH$_3$, 8-F | —OEt | —CH$_3$ | —CH$_3$ | — | 102-103 |
| a-57 | 2-CH$_3$, 8-F | —OEt | —CH$_3$ | —Et | — | |
| a-58 | 2-CH$_3$, 8-F | —O$^i$Pr | —CH$_3$ | —CH$_3$ | — | |
| a-59 | 2-CH$_3$, 8-F | —O$^n$Pr | —CH$_3$ | —CH$_3$ | — | |
| a-60 | 2-CH$_3$, 8-F | —CH$_2$CN | —CH$_3$ | —CH$_3$ | — | |
| a-61 | 2-CH$_3$, 8-F | —OCH$_2$(Py-3-yl) | —CH$_3$ | —CH$_3$ | — | |
| a-62 | 2-CH$_3$, 7,8-F$_2$ | —OCH$_2$CH=CH$_2$ | —CH$_3$ | —CH$_3$ | — | |
| a-63 | 2-CH$_3$, 7,8-F$_2$ | —OCH$_2$Ph | —CH$_3$ | —CH$_3$ | — | |
| a-64 | 8-F | —CH$_3$ | —CH$_3$ | —CO$_2$Et | — | |
| a-65 | 8-F | —CH$_3$ | —CH$_3$ | —CO$_2$$^n$Pr | — | |
| a-66 | 8-F | —CH$_3$ | —CH$_3$ | —CO$_2$$^t$Bu | — | |
| a-67 | 8-F | —CH$_3$ | —CH$_3$ | —CO$_2$C$_2$H$_4$OCH$_3$ | — | |
| a-68 | 8-F | —CH$_3$ | —CH$_3$ | —CO$_2$C$_2$H$_4$N(CH$_3$)$_2$ | — | |
| a-69 | 8-F | —CH$_3$ | —CH$_3$ | —CO$_2$CH$_2$CH=CH$_2$ | — | |
| a-70 | 8-F | —CH$_3$ | —CH$_3$ | —CON(CH$_3$)CH$_2$CF$_3$ | — | |
| a-71 | 8-F | —CH$_3$ | —CH$_3$ | —CONH$^i$Pr | — | |
| a-72 | 8-F | —CH$_3$ | —CH$_3$ | —CO(pyrrolidin-1-yl) | — | |
| a-73 | 8-F | —CH$_3$ | —CH$_3$ | —COC$_2$H$_4$OCH$_3$ | — | |
| a-74 | 7,8-F$_2$ | —CH$_3$ | —CH$_3$ | —CO$_2$$^i$Pr | — | * |
| a-75 | 8-F | —CH$_3$ | —CH$_3$ | —CO$_2$CH$_3$ | — | * |
| a-76 | 2-CH$_3$, 8-F | —CH$_3$ | —CH$_3$ | —CO$_2$$^i$Pr | — | * |
| a-77 | 2-CH$_3$, 7,8-F$_2$ | —CH$_3$ | —CH$_3$ | —CO$_2$$^i$Pr | — | * |
| a-78 | 2-CH$_3$, 8-F | —OSi(CH$_3$)$_3$ | —CH$_3$ | —CF$_3$ | — | * |
| a-79 | 2-CH$_3$, 8-F | —OH | —CH$_3$ | —CF$_3$ | — | * |
| a-80 | 2-CH$_3$, 8-F | =CH$_2$ | | —CH$_3$ | — | 102-103 |
| a-81 | 2-CH$_3$, 7,8-F$_2$ | —OEt | —CH$_3$ | —CH$_3$ | — | 135-136 |
| a-82 | 2-CH$_3$, 7,8-F$_2$ | —OH | —CH$_3$ | —Et | — | 157-159 |
| a-83 | 2-CH$_3$, 7,8-F$_2$ | —OCH$_3$ | —CH$_3$ | —Et | — | 99-100 |
| a-84 | 2-CH$_3$, 8-Cl | —OH | —CH$_3$ | —CH$_3$ | — | 131-132 |
| a-85 | 2-CH$_3$, 8-Cl | —OCH$_3$ | —CH$_3$ | —CH$_3$ | — | 130-131 |
| a-86 | 2-CH$_3$, 7,8-F$_2$ | —OCH$_2$C≡CH | —CH$_3$ | —CH$_3$ | — | * |
| a-87 | 2,8-(CH$_3$)$_2$ | —OCH$_3$ | —CH$_3$ | —CH$_3$ | — | 101-103 |
| a-88 | 2-CH$_3$, 7,8-F$_2$ | —OEt | —CH$_3$ | —Et | — | * |
| a-89 | 2-CH$_3$, 8-Cl | =O | | —CH$_3$ | — | 159-160 |
| a-90 | 2-CH$_3$, 7,8-F$_2$ | =CHCH$_3$ | | —CH$_3$ | — | 72-74 |
| a-91 | 2-CH$_3$, 7-F | —OCH$_3$ | —CH$_3$ | —CH$_3$ | — | 106-108 |
| a-92 | 2-CH$_3$, 7-F | —OEt | —CH$_3$ | —CH$_3$ | — | 81-82 |
| a-93 | 2-CH$_3$, 7-F | —OCH$_3$ | —CH$_3$ | —Et | — | 95-96 |
| a-94 | — | —CH$_3$ | —CH$_3$ | —CO$_2$$^i$Pr | — | $n_D^{20.6}$1551 |
| a-95 | 2-CH$_3$, 7-F | —CH$_3$ | —CH$_3$ | —CO$_2$$^i$Pr | — | 108-110 |
| a-96 | 2-CH$_3$, 7-F | —OCH$_2$C≡CH | —CH$_3$ | —CH$_3$ | — | * |
| a-97 | 2-CH$_3$, 8-F | —CH$_3$ | —CH$_3$ | —CO$_2$$^c$Pen | — | 124-126 |
| a-98 | 2-CH$_3$, 8-F | —CH$_3$ | —CH$_3$ | —CO$_2$CH(CH$_3$)CH$_2$OCH$_3$ | — | * |
| a-99 | 2-CH$_3$ | —CH$_3$ | —CH$_3$ | —CO$_2$$^i$Pr | — | 122-124 |
| a-100 | 2-CH$_3$, 7-F | —OH | —CH$_3$ | —CH$_3$ | — | 152-153 |
| a-101 | 2-CH$_3$, 8-F | —OCH$_3$ | —CH$_3$ | —CH$_3$ | 6-Cl | 101-102 |
| a-102 | 2-CH$_3$, 8-F | —OCH$_3$ | —CH$_3$ | —CH$_3$ | 6-CH$_3$ | 103-105 |
| a-103 | 2-CH$_3$, 8-OCH$_3$ | —OCH$_3$ | —CH$_3$ | —CH$_3$ | 6-OCH$_3$ | 129-131 |
| a-104 | 2-CH$_3$, 6-OCH$_3$ | —OH | —CH$_3$ | —CH$_3$ | — | * |

[Chemical Formula 51]

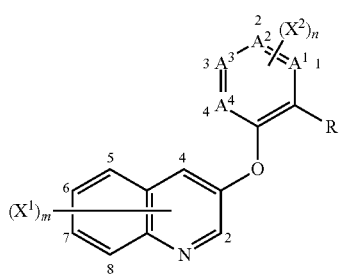

$R = CR^1R^2R^3$

Compound a-74: 1.09 (d, 6H), 1.64 (s, 3H), 4.83 (m, 1H), 7.19-7.26 (m, 2H), 7.43-7.46 (m, 2H), 7.59 (s, 1H), 8.44 (m, 1H), 8.81 (d, 1H)

Compound a-75: 1.67 (s, 6H), 3.43 (s, 3H), 7.22-7.38 (m, 3H), 7.48-7.50 (m, 2H), 7.60 (m, 1H), 8.45 (m, 1H), 8.75 (d, 1H)

Compound a-76: 1.05 (d, 6H), 1.66 (s, 6H), 2.80 (s, 3H), 4.78 (m, 1H), 7.20-7.33 (m, 3H), 7.38-7.40 (m, 3H), 8.44 (m, 1H)

Compound a-77: 1.05 (d, 6H), 1.65 (s, 6H), 2.80 (s, 3H), 4.77 (m, 1H), 7.17-7.26 (m, 2H), 7.32-7.38 (m, 3H), 8.44 (m, 1H)

Compound a-78: −0.07 (s, 9H), 1.55 (s, 3H), 2.81 (s, 3H), 7.20-7.36 (m, 6H), 1668.46 (m, 1H)

Compound a-79: 1.93 (s, 3H), 2.77 (s, 3H), 6.59 (s, 1H), 7.25-7.42 (m, 6H), 8.45 (m, 1H)

Compound a-86: 1.75 (s, 6H), 2.06 (t, 1H), 2.85 (s, 3H), 3.93 (d, 2H), 7.23-7.33 (m, 5H), 8.43 (m, 1H)

TABLE 2

| Compound No. | $(X^1)_m$ | $R^1$ | $R^2$ | $R^3$ | $A^1, A^2, A^3, A^4$ | $(X^2)_n$ | Physical Properties |
|---|---|---|---|---|---|---|---|
| b-1 | — | —F | —F | —F | C, C, C, N | — | * |
| b-2 | — | —OH | —CH$_3$ | —CH$_3$ | C, C, C, N | — | 146-147 |
| b-3 | 2-CH$_3$, 8-F | =O | | —OEt | C, C, C, N | — | 119-121 |
| b-4 | 2-CH$_3$, 8-F | —OH | —CH$_3$ | —CH$_3$ | C, C, C, N | — | 140-142 |
| b-5 | 2-CH$_3$, 8-F | —OCH$_3$ | —CH$_3$ | —CH$_3$ | C, C, C, N | — | * |
| c-1 | 2-CH$_3$, 8-F | —OH | —CH$_3$ | —Et | C, C, N, C | 1-Cl | 105-107 |

The $^1$H-NMR spectra (300 MHz, CDCl$_3$) δ were measured for compounds indicated in the aforementioned tables having an asterisk in the physical properties column. A portion of the measurement results are shown below.

Compound a-2: 1.67 (s, 6H), 6.00 (s, 1H), 7.54-7.61 (m, 2H), 7.66-7.74 (m, 2H), 8.14 (d, 1H), 8.38 (t, 1H), 8.80 (d, 1H)

Compound a-7: 1.66 (s, 6H), 2.81 (s, 3H), 6.02 (s, 1H), 7.19-7.43 (m, 6H), 8.40 (d, 1H)

Compound a-8: 1.65 (s, 6H), 5.96 (s, 1H), 7.25-7.39 (m, 3H), 7.48-7.58 (m, 3H), 8.41 (m, 1H), 8.85 (d, 1H)

Compound a-12: 1.07 (t, 3H), 1.66 (s, 6H), 3.88 (q, 2H), 7.23-7.27 (m, 2H), 7.34 (m, 1H), 7.46-7.50 (m, 2H), 7.58 (m, 1H), 8.45 (d, 1H), 8.76 (d, 1H)

Compound a-20: 1.65 (s, 6H), 2.98 (s, 3H), 3.23 (s, 3H), 7.17-7.22 (m, 2H), 7.34 (m, 1H), 7.46-7.52 (m, 2H), 7.64 (m, 1H), 8.44 (dd, 1H), 8.75 (d, 1H)

Compound a-22: 1.05 (t, 3H), 1.66 (s, 6H), 2.79 (s, 3H), 3.80 (q, 2H), 7.25-7.35 (m, 3H), 7.40-7.50 (m, 3H), 8.45 (m, 1H)

Compound a-33: 1.88 (s, 6H), 7.10-7.29 (m, 2H), 7.40-7.50 (m, 2H), 7.70 (m, 1H), 8.42 (d, 1H), 8.91 (d, 1H)

Compound a-43: 1.08 (t, 3H), 1.46-1.65 (m, 2H), 3.88 (d, 1H), 4.63 (br, 1H), 7.20-7.34 (m, 3H), 7.48-7.50 (m, 3H), 8.39 (m, 1H), 8.83 (d, 1H)

Compound a-44: 1.58 (s, 6H), 3.17 (s, 3H), 3.69 (s, 2H), 7.18-7.26 (m, 2H), 7.34 (m, 1H), 7.44-7.49 (m, 3H), 8.48 (m, 1H), 8.86 (d, 1H)

Compound a-45: 0.96 (t, 3H), 1.59 (s, 6H), 2.50 (q, 2H), 7.19-7.23 (m, 2H), 7.34 (m, 1H), 7.48-7.51 (m, 2H), 7.57 (m, 1H), 8.47 (m, 1H), 8.74 (d, 1H)

Compound a-46: 1.07 (t, 3H), 1.84 (s, 3H), 2.05 (m, 1H), 2.38 (m, 1H), 7.24-7.40 (m, 3H), 7.49-7.51 (m, 2H), 7.66 (m, 1H), 8.43 (d, 1H), 8.85 (d, 1H)

Compound a-48: 0.85 (t, 3H), 1.07 (t, 3H), 1.61 (s, 6H), 2.04-2.26 (m, 2H), 3.86 (q, 2H), 7.24-7.26 (m, 2H), 7.34 (m, 1H), 7.48-7.50 (m, 2H), 7.58 (m, 1H), 8.46 (m, 1H), 8.76 (d, 1H)

Compound a-88: 0.8-0.9 (m, 6H), 1.66 (s, 3H), 2.0-2.2 (m, 2H), 2.84 (s, 3H), 3.1-3.4 (m, 2H), 7.19-7.33 (m, 5H), 8.45 (m, 1H)

Compound a-96: 1.76 (s, 6H), 2.10 (t, 1H), 2.77 (s, 3H), 3.95 (d, 2H), 7.18-7.25 (m, 3H), 7.5-7.6 (m, 2H), 8.39 (m, 1H)

Compound a-98: 1.04 (d, 3H), 1.68 (s, 6H), 2.79 (s, 3H), 3.17 (s, 3H), 3.26 (m, 2H), 4.90 (m, 1H), 7.15-7.23 (m, 2H), 7.26-7.40 (m, 3H), 7.47 (s, 1H), 8.42 (m, 1H)

Compound a-104: 1.68 (s, 6H), 2.70 (s, 3H), 3.88 (s, 3H), 6.06 (bs, 1H), 6.91 (d, 1H), 7.14-7.34 (m, 3H), 7.94 (d, 1H), 8.36 (dd, 1H)

Compound b-1: 7.13 (m, 1H), 7.54 (m, 1H), 7.69 (m, 1H), 7.79 (m, 1H), 7.96-8.04 (m, 2H), 8.14 (d, 1H), 8.25 (br, 1H), 8.83 (d, 1H)

Compound b-5: 1.73 (s, 6H), 2.65 (s, 3H), 3.30 (s, 3H), 7.06 (m, 1H), 7.3-7.5 (m, 3H), 7.71 (d, 1H), 7.91 (dd, 1H), 7.98 (m, 1H)

Nitrogenated heterocyclic compounds obtained in the aforementioned examples and nitrogenated heterocyclic compounds synthesized according to methods similar to any of the aforementioned examples are shown in Tables 3 and 4.

In Table 3, $R^1$, $R^2$, $R^3$, $(X^1)_m$, $A^1$ and $(X^2)_n$ represent those groups shown in formula (2).

In Table 4, $R^1$, $R^2$, $R^3$, $(X^1)_m$, B, $A^1$ and $(X^2)_n$ represent those groups shown in formula (3).

In addition, the symbol $n_D$ shown in the column entitled physical properties indicates the refractive index (and the number shown in superscript indicates the measurement temperature (° C.)).

[Chemical Formula 52]

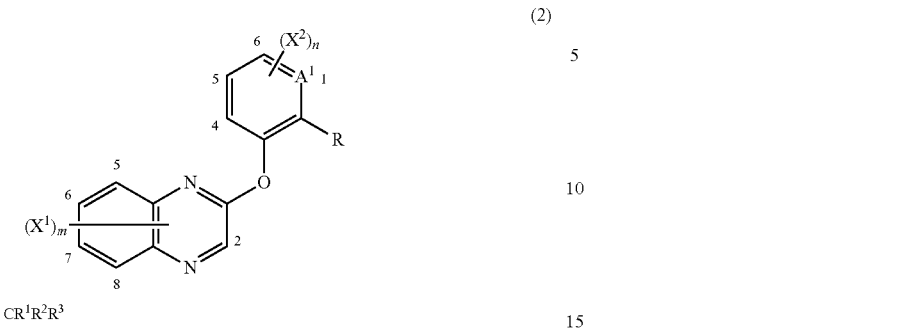

(2)

R = CR¹R²R³

TABLE 3

| Compound No. | $(X^1)_m$ | $R^1$ | $R^2$ | $R^3$ | $A^1$ | $(X^2)_n$ | Physical Properties |
|---|---|---|---|---|---|---|---|
| 1-1 | — | —CH₃ | —CH₃ | —CH₃ | C | — | * |
| 1-2 | — | —CH₃ | —CH₃ | —C(CH₃)₂—OH | C | — | * |
| 1-3 | — | =O | | —OCH₃ | C | — | 105-107 |
| 1-4 | — | —CH₃ | —CH₃ | —COCH₃ | C | 1-F | 110-112 |
| 1-5 | — | —OCH₃ | —CH₃ | —CH₃ | C | 1-F | 104-105 |
| 1-6 | 8-F | —OCH₃ | —CH₃ | —CH₃ | C | 1-F | 125-127 |
| 1-7 | 2-CH₃, 8-F | —OCH₃ | —CH₃ | —CH₃ | C | 1-F | 105-107 |
| 1-8 | 8-F | —OCH₃ | —H | —CH₃ | C | 1-Cl | 95-97 |
| 1-9 | — | —OCH₃ | —H | —CH₃ | C | 1-Cl | * |
| 1-10 | 8-F | —CH₃ | —CH₃ | —COCH₃ | C | 1-F | 115-118 |
| 1-11 | 2-CH₃, 8-F | —CH₃ | —CH₃ | —COCH₃ | C | 1-F | 111-113 |
| 1-12 | 7,8-F₂ | —CH₃ | —CH₃ | —CH₃ | C | 1-F | 150-152 |
| 1-13 | 2-CH₃, 7,8-F₂ | —OCH₃ | —CH₃ | —CH₃ | C | 1-F | 144-146 |
| 1-14 | 7,8-F₂ | —CH₃ | —CH₃ | —COCH₃ | C | 1-F | 133-135 |
| 1-15 | 2-CH₃, 7,8-F₂ | —CH₃ | —CH₃ | —COCH₃ | C | 1-F | 140-142 |
| 1-16 | 2-CH₃, 8-F | F | F | —COCH₃ | N | — | 114-116 |
| 1-17 | 2-CH₃, 8-F | F | F | —C(CH₃)₂—OH | N | — | * |
| 1-18 | 8-F | —CH₃ | —CH₃ | —CO₂$^t$Bu | C | — | 96-98 |
| 1-19 | 8-F | —CH₃ | —CH₃ | —CO₂$^i$Pr | C | — | * |
| 1-20 | 8-F | —CH₃ | —CH₃ | —CN | N | — | 125-127 |
| 1-21 | 8-F | —CH₃ | —CH₃ | —CO₂Et | N | — | 69-73 |
| 1-22 | 8-F | —CH₃ | —CH₃ | —CO₂$^c$Pen | C | — | 99-101 |
| 1-23 | 2-CH₃, 8-F | —CH₃ | —CH₃ | —CO₂$^i$Pr | C | — | 109-109 |
| 1-24 | 7,8-F₂ | —CH₃ | —CH₃ | —CO₂$^i$Pr | C | — | * |
| 1-25 | 2-CH₃, 7,8-F₂ | —CH₃ | —CH₃ | —CO₂$^i$Pr | C | — | 136-138 |
| 1-25 | 8-F | —OCH₃ | —CH₃ | —CH₃ | N | — | 88-90 |
| 1-27 | 2-CH₃, 8-F | —OCH₃ | —CH₃ | —CH₃ | N | — | 110-112 |
| 1-28 | 7,8-F₂ | —OCH₃ | —CH₃ | —CH₃ | N | — | 111-112 |
| 1-29 | 8-F | —OCH₂CH=CH₂ | —CH₃ | —CH₃ | N | — | 75-78 |
| 1-30 | 2-CH₃, 8-F | —OCH₂CH=CH₂ | —CH₃ | —CH₃ | N | — | 121-123 |
| 1-31 | 7,8-F₂ | —OCH₂CH=CH₂ | —CH₃ | —CH₃ | N | — | 100-102 |
| 1-32 | 2-CH₃, 8-F | —OCH₃ | —CH₃ | —CH₃ | N | 1-O⁻ | 187-189 |
| 1-33 | 2-CH₃, 8-F | —O$^n$Pr | —CH₃ | —CH₃ | N | — | * |
| 1-34 | 8-F | —CH₃ | —CH₃ | —CO₂$^i$Pr | C | 1-F | * |
| 1-35 | 2-CH₃, 7,8-F₂ | —OCH₃ | —CH₃ | —CH₃ | N | — | 161-163 |
| 1-36 | — | —CH₃ | —CH₃ | —CO₂$^i$Pr | N | — | 48-50 |
| 1-37 | 8-F | —CH₃ | —CH₃ | —CO₂$^i$Pr | N | — | 109-111 |
| 1-38 | 7,8-F₂ | —CH₃ | —CH₃ | —CO₂$^i$Pr | N | — | 72-74 |
| 1-39 | 7,8-F₂ | —CH₃ | —CH₃ | —CO₂CH₃ | N | — | 123-125 |
| 1-40 | 2-CH₃, 7,8-F₂ | —OCH₃ | —CH₃ | —Et | N | — | 139-142 |
| 1-41 | 7,8-F₂ | —Et | —CH₃ | —CN | N | — | 140-141 |
| 1-42 | 7,8-F₂ | —Et | —CH₃ | —CO₂$^i$Pr | N | — | * |
| 1-43 | 7,8-F₂ | —OCH₃ | —Et | —Et | N | — | 110-112 |
| 1-44 | 2-CH₃, 7,8-F₂ | —OCH₃ | —Et | —Et | N | — | 155-157 |
| 1-45 | 2-CH₃, 7,8-F₂ | —OCH₃ | —CH₃ | —CH₂CH=CH₂ | N | — | 108-110 |
| 1-46 | 2-CH₃, 7-F | —CH₃ | —CH₃ | —CO₂$^i$Pr | N | — | 58-61 |
| 1-47 | 2-CH₃, 7-F | —OCH₃ | —CH₃ | —Et | N | — | 105-106 |
| 1-48 | 2-CH₃, 7,8-F₂ | —CH₃ | —CH₃ | —CO₂$^i$Pr | N | — | 109-113 |
| 1-49 | 2-CH₃, 7,8-F₂ | —OCH₃ | —CH₃ | —$^n$Pr | N | — | 115-116 |
| 1-50 | 2-CH₃, 8-F | —OCH₃ | —CH₃ | —Et | N | — | 110-111 |
| 1-51 | 2-CH₃, 7,8-F₂ | —OEt | —CH₃ | —CH₃ | N | — | 116-118 |
| 1-52 | 7,8-F₂ | —CH₂CH₂— | | —CO₂$^i$Pr | N | — | 107-109 |
| 1-53 | 2-CH₃, 7,8-F₂ | —CH₂CH₂— | | —CO₂$^i$Pr | N | — | 111-113 |
| 1-54 | 2-CH₃, 7-F | —OCH₃ | —CH₃ | —CH₂CH=CH₂ | N | — | 94-96 |
| 1-55 | 7,8-F₂ | —OCH₃ | —CH₃ | —CH₂CH=CH₂ | N | — | 68-70 |

TABLE 3-continued

| Compound No. | $(X^1)_m$ | $R^1$ | $R^2$ | $R^3$ | $A^1$ | $(X^2)_n$ | Physical Properties |
|---|---|---|---|---|---|---|---|
| 1-56 | 2-CH$_3$, 7,8-F$_2$ | —OCH$_2$CH=CH$_2$ | —CH$_3$ | —CH$_3$ | N | — | 99-101 |
| 1-57 | 7,8-F$_2$ | —CH$_3$ | —CH$_3$ | —CON(CH$_3$)$^n$Bu | N | — | $n_D^{23.8}$1.553 |
| 1-58 | 7,8-F$_2$ | —CH$_3$ | —CH$_3$ | —CON(Et)$^n$Bu | N | — | $n_D^{23.5}$1.547 |
| 1-59 | 2-CH$_3$, 7-F | —OCH$_3$ | —CH$_3$ | —$^n$Pr | N | — | $n_D^{23.2}$1.566 |
| 1-60 | 2-CH$_3$, 7-F | —OCH$_3$ | —CH$_3$ | —CH$_3$ | N | — | 105-106 |
| 1-61 | 2,8-(CH$_3$)$_2$ | —CH$_3$ | —CH$_3$ | —CO$_2$$^i$Pr | N | — | 84-86 |
| 1-62 | 2,8-(CH$_3$)$_2$ | —OCH$_3$ | —CH$_3$ | —CH$_3$ | N | — | 98-100 |
| 1-63 | 2-CH$_3$ | —CH$_3$ | —CH$_3$ | —CO$_2$$^i$Pr | N | — | 110-112 |
| 1-64 | 2-CH$_3$, 7-F | —CH$_3$ | —CH$_3$ | —OEt | N | — | 89-91 |
| 1-65 | 2-CH$_3$, 7-F | —CH$_3$ | —CH$_3$ | —OCH$_2$CH=CH$_2$ | N | — | 39-41 |
| 1-66 | 7,8-F$_2$ | —CH$_3$ | —CH$_3$ | —CO$_2$CH(CH$_3$)Et | N | — | 75-77 |
| 1-67 | 7,8-F$_2$ | —CH$_3$ | —CH$_3$ | —CO$_2$$^c$Pen | N | — | 75-77 |
| 1-68 | 7,8-F$_2$ | —CH$_3$ | —CH$_3$ | —CO$_2$CH(CH$_3$)CH$_2$OCH$_3$ | N | — | * |
| 1-69 | 7,8-F$_2$ | —CH$_3$ | —CH$_3$ | —CO$_2$(Tetrahydro-furan-3-yl) | N | — | * |
| 1-70 | 7-F | —CH$_3$ | —CH$_3$ | —CO$_2$$^i$Pr | N | — | 61-63 |
| 1-71 | 2-CH$_3$, 8-Cl | —CH$_3$ | —CH$_3$ | —OEt | N | — | 167-169 |
| 1-72 | — | —CH$_3$ | —CH$_3$ | —CO$_2$$^c$Pen | N | — | 114-116 |
| 1-73 | 2-CH$_3$ | —CH$_3$ | —CH$_3$ | —CO$_2$$^c$Pen | N | — | 151-153 |
| 1-74 | 7-F | —CH$_3$ | —CH$_3$ | —CO$_2$$^c$Pen | N | — | 80-82 |
| 1-75 | 2-Cl | —CH$_3$ | —CH$_3$ | —CO$_2$$^i$Pr | N | — | 158-160 |
| 1-76 | 2-CH$_3$, 8-Cl | —CH$_3$ | —CH$_3$ | —OEt | N | — | 114-116 |
| 1-77 | 2-CH$_3$, 8-Cl | —CH$_3$ | —CH$_3$ | —CO$_2$$^i$Pr | N | — | 117-119 |
| 1-78 | 2-SCH$_3$ | —CH$_3$ | —CH$_3$ | —CO$_2$$^i$Pr | N | — | 155-157 |
| 1-79 | 2-CH$_3$, 7-F | —CH$_3$ | —CH$_3$ | —CN | N | — | 114-115 |
| 1-80 | 2-CH$_3$, 7,8-F2 | —CH$_3$ | —CH$_3$ | —CN | N | — | 145-147 |
| 1-81 | 2-CH$_3$, 7,8-F$_2$ | | =O | —OCH$_3$ | C | — | 138-140 |
| 1-82 | 2-CH$_3$, 7,8-F$_2$ | | =O | —N(CH$_3$)$_2$ | C | — | 152-153 |
| 1-83 | 2-CH$_3$, 7,8-F$_2$ | | | =N | C | — | 158-161 |
| 1-84 | 2-CH$_3$, 7,8-F$_2$ | —Et | —CH$_3$ | —CN | N | — | 129-132 |
| 1-85 | 2-CH$_3$, 7,8-F$_2$ | —Et | —CH$_3$ | —CN | N | — | 143-145 |

[Chemical Formula 53]

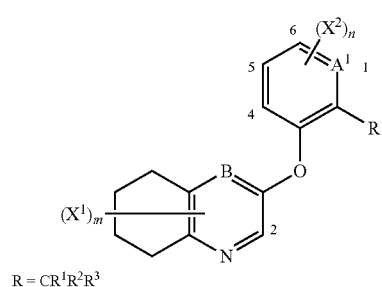

$R = CR^1R^2R^3$

TABLE 4

| Compound No. | $(X^1)_m$ | $R^1$ | $R^2$ | $R^3$ | B | $A^1$ | $(X^2)_n$ | Physical Properties |
|---|---|---|---|---|---|---|---|---|
| 2-1 | — | | =O | —H | N | C | 1-Cl | 107-109 |
| 2-2 | — | —OH | —H | —CH$_3$ | N | C | 1-Cl | 91-93 |
| 2-3 | — | | =O | —H | N | C | 1-F | 106-108 |
| 2-4 | — | —OCH$_3$ | —CH$_3$ | —CH$_3$ | C | N | — | * |
| 2-5 | — | —OCH$_3$ | —CH$_3$ | —CH$_3$ | N | N | — | |
| 2-6 | — | | =N | | C | N | — | 114-116 |
| 2-7 | — | —OH | —CH$_3$ | —CH$_3$ | C | N | — | 74-75 |
| 2-8 | — | —OCH$_3$ | —CH$_3$ | —CH$_3$ | N | C | — | |
| 2-9 | — | —CH$_3$ | —CH$_3$ | —CO$_2$$^i$Pr | C | C | — | |
| 2-10 | — | —CH$_3$ | —CH$_3$ | —CO$_2$$^i$Pr | C | N | — | |
| 2-11 | — | —CH$_3$ | —CH$_3$ | —CO$_2$$^i$Pr | N | C | — | |
| 2-12 | — | —CH$_3$ | —CH$_3$ | —CO$_2$$^i$Pr | N | N | — | |

The $^1$H-NMR spectra (300 MHz, CDCl$_3$) δ were measured for compounds indicated in the aforementioned tables having an asterisk in the physical properties column. A portion of the measurement results are shown below.

Compound 1-1: 1.41 (s, 9H), 7.13 (d, 1H), 4.22-7.28 (m, 2H), 7.49 (m, 1H), 7.59-7.69 (m, 2H), 7.80 (d, 1H), 8.07 (d, 1H), 8.67 (s, 1H)

Compound 1-2: 1.22 (s, 6H), 1.50 (s, 6H), 1.97 (s, 1H), 7.09 (m, 1H), 7.23-7.33 (m, 2H), 7.57-7.68 (m, 3H), 7.77 (m, 1H), 8.07 (m, 1H), 8.67 (s, 1H)

Compound 1-9: 1.58 (d, 3H), 3.00 (s, 3H), 4.95 (q, 1H), 7.13 (m, 1H), 7.28-7.37 (m, 3H), 7.57-7.71 (m, 3H), 8.07 (m, 1H), 8.72 (s, 1H)

Compound 1-17: 1.40 (s, 6H), 2.89 (s, 3H), 5.26 (s, 1H), 7.30 (m, 1H), 7.42 (d, 1H), 7.48-7.61 (m, 2H), 7.86 (m, 1H), 8.55 (d, 1H)

Compound 1-19: 1.05 (d, 6H), 1.54 (s, 6H), 4.75 (m, 1H), 7.28-7.36 (m, 4H), 7.50 (d, 1H), 7.58-7.59 (m, 2H), 8.65 (s, 1H)

Compound 1-24: 1.05 (d, 6H), 1.52 (s, 6H), 4.74 (m, 1H), 7.26-7.36 (m, 3H), 7.48-7.56 (m, 3H), 8.66 (s, 1H)

Compound 1-33: 0.38 (t, 3H), 0.73 (m, 2H), 1.69 (s, 6H), 2.93 (s, 3H), 2.98 (t, 2H), 7.27 (m, 1H), 7.35-7.49 (m, 3H), 7.63 (d, 1H), 8.51 (d, 1H)

Compound 1-34: 1.12 (d, 6H), 1.59 (s, 6H), 4.86 (m, 1H), 6.97-7.05 (m, 2H), 7.25-7.36 (m, 2H), 7.56-7.63 (m, 2H), 8.65 (s, 1H)

Compound 1-42: 0.77 (t, 3H), 1.03 (d, 6H), 1.51 (s, 3H), 2.11 (q, 2H), 4.77 (m, 1H), 7.33 (dd, 1H), 7.50-7.58 (m, 2H), 7.73 (dd, 1H), 8.52 (dd, 1H), 8.70 (s, 1H)

Compound 1-68: 1.05 (d, 3H), 1.59 (s, 6H), 3.19 (s, 3H), 3.21-3.30 (m, 2H), 4.95 (m, 1H), 7.33 (dd, 1H), 7.54-7.58 (m, 2H), 7.78 (dd, 1H), 8.51 (dd, 1H), 8.74 (s, 1H)

Compound 1-69: 1.58 (s, 6H), 1.75-1.92 (m, 2H), 3.58-3.70 (m, 4H), 4.93 (m, 1H), 7.34 (dd, 1H), 7.54-7.59 (m, 2H), 7.72 (dd, 1H), 8.52 (dd, 1H), 8.72 (s, 1H)

Compound 2-4: 1.68 (s, 6H), 1.76-1.82 (m, 2H), 1.86-1.92 (m, 2H), 2.73 (t, 2H), 2.89 (t, 2H), 3.14 (s, 3H), 6.98 (d, 1H), 7.15-7.16 (m, 2H), 8.09 (d, 1H), 8.35 (d, 1H)

Nitrogenated heterocyclic compounds synthesized according to methods similar to any of the aforementioned examples are shown in Tables 5 and 6.

In Table 5, $R^1$, $R^2$, $R^3$, B, $A^1$ and $(X^2)_n$ represent those groups shown in formula (4).

In Table 6, $R^1$, $R^2$, $R^3$, B, $A^1$ and $(X^2)_n$ represent those groups shown in formula (5).

[Chemical Formula 54]

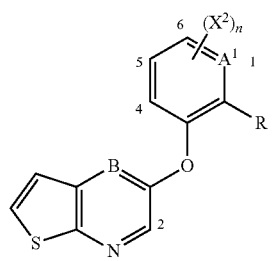

(4)

R = $CR^1R^2R^3$

[Chemical Formula 55]

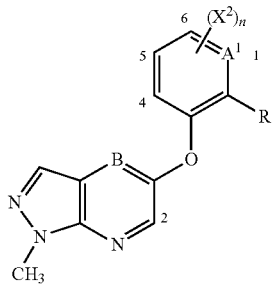

(5)

R = $CR^1R^2R^3$

TABLE 6

| Compound No. | $R^1$ | $R^2$ | $R^3$ | B | $A^1$ | $(X^2)_n$ | Physical Properties |
|---|---|---|---|---|---|---|---|
| 4-1 | | =O | —H | N | C | 1-Cl | |
| 4-2 | —OH | —H | —CH₃ | N | C | 1-Cl | |
| 4-3 | | =O | —H | N | C | 1-F | |
| 4-4 | —OCH₃ | —CH₃ | —CH₃ | C | N | — | |
| 4-5 | —OCH₃ | —CH₃ | —CH₃ | N | N | — | |
| 4-6 | —OCH₃ | —CH₃ | —CH₃ | N | C | — | |
| 4-7 | —CH₃ | —CH₃ | —CO₂$^i$Pr | C | C | — | |
| 4-8 | —CH₃ | —CH₃ | —CO₂$^i$Pr | C | N | — | |
| 4-9 | —CH₃ | —CH₃ | —CO₂$^i$Pr | N | C | — | |
| 4-10 | —CH₃ | —CH₃ | —CO₂$^i$Pr | N | N | — | |

Preparations

Although the following indicates examples of agricultural or horticultural fungicides according to the present invention, the additives used and ratios at which they are added are not limited to those shown in the examples, but rather can be varied over a wide range. In addition, the term "parts" in the preparation examples indicates parts by weight.

Preparation Example 1

Wettable Powder

| | |
|---|---|
| Compound of present invention | 40 parts |
| Clay | 48 parts |
| Sodium dioctylsulfosuccinate | 4 parts |
| Sodium lignin sulfonate | 8 parts |

The above components were uniformly mixed and finely pulverized to obtain a wettable powder containing 40% of the active ingredient.

Preparation Example 2

Emulsion

| | |
|---|---|
| Compound of present invention | 10 parts |
| Solvesso 200 | 53 parts |
| Cyclohexanone | 26 parts |
| Calcium dodecylbenzenesulfonate | 1 part |
| Polyoxyethylene alkyl aryl ether | 10 parts |

TABLE 5

| Compound No. | $R^1$ | $R^2$ | $R^3$ | B | $A^1$ | $(X^2)_n$ | Physical Properties |
|---|---|---|---|---|---|---|---|
| 3-1 | | =O | —H | N | C | 1-Cl | |
| 3-2 | —OH | —H | —CH₃ | N | C | 1-Cl | |
| 3-3 | | =O | —H | N | C | 1-F | |
| 3-4 | —OCH₃ | —CH₃ | —CH₃ | C | N | — | 101-103 |
| 3-5 | | ≡N | | C | N | — | 171-172 |
| 3-6 | | =O | —CH₃ | C | N | — | 94-96 |
| 3-7 | —OCH₃ | —CH₃ | —CH₃ | N | N | — | |
| 3-8 | —OCH₃ | —CH₃ | —CH₃ | N | C | — | |
| 3-9 | —CH₃ | —CH₃ | —CO₂$^i$Pr | C | C | — | |
| 3-10 | —CH₃ | —CH₃ | —CO₂$^i$Pr | C | N | — | |
| 3-11 | —CH₃ | —CH₃ | —CO₂$^i$Pr | N | C | — | |
| 3-12 | —CH₃ | —CH₃ | —CO₂$^i$Pr | N | N | — | |

The above components were mixed and dissolved to obtain an emulsion containing 10% of the active ingredient.

Preparation Example 3

Powder

| Compound of present invention | 10 parts |
|---|---|
| Clay | 90 parts |

The above components were uniformly mixed and finely pulverized to obtain a powder containing 10% of the active ingredient.

Preparation Example 4

Granules

| Compound of present invention | 5 parts |
|---|---|
| Clay | 73 parts |
| Bentonite | 20 parts |
| Sodium dioctylsulfosuccinate | 1 part |
| Potassium phosphate | 1 part |

The above components were pulverized and mixed well followed by the addition of water, mixing well, granulating and drying to obtain granules containing 5% of the active ingredient.

Preparation Example 5

Suspension

| Compound of present invention | 10 parts |
|---|---|
| Polyoxyethylene alkyl aryl ether | 4 parts |
| Sodium polycarbonate | 2 parts |
| Glycerin | 10 parts |
| Xanthan gum | 0.2 parts |
| Water | 73.8 parts |

The above components were mixed followed by wet-pulverizing to a particle size of 3 microns or less to obtain a suspension containing 10% of the active ingredient.

Preparation Example 6

Wettable Granules

| Compound of present invention | 40 parts |
|---|---|
| Clay | 36 parts |
| Potassium chloride | 10 parts |
| Sodium alkylbenzenesulfonate | 1 part |
| Sodium lignin sulfonate | 8 parts |
| Formaldehyde condensation product of sodium alkylbenzenesulfonate | 5 parts |

The above components were uniformly mixed and finely pulverized followed by adding a suitable amount of water and kneading to form a clay-like mixture. The clay-like mixture was granulated and dried to obtain wettable granules containing 40% of the active ingredient.

Biological Test Example 1-1

Apple Scab Control Test

Emulsions of compounds of the present invention were sprayed at an active ingredient concentration of 100 ppm onto apple seedlings (variety: Ralls Janet, leaf stage: 3 to 4) cultivated in unglazed pots and allowed to air-dry at room temperature. Subsequently, the seedlings were inoculated with conidiospores of apple scab pathogen (*Venturia inaequalis*) followed by holding for 2 weeks indoors at 20° C. and high humidity using a 12 hour light/dark cycle. The appearance of lesions on the leaves was compared with untreated seedlings to determine control effects.

Apple scab control tests were carried out on compound nos. a-2, a-3, a-4, a-5, a-6, a-7, a-8, a-9, a-10, a-11, a-12, a-14, a-15, a-16, a-17, a-18, a-19, a-20, a-21, a-22, a-23, a-27, a-28, a-29, a-30, a-31, a-32, a-33, a-34, a-35, a-36, a-37, a-38, a-39, a-40, a-41, a-42, a-43, a-44, a-45, a-46, a-47, a-48, a-49, a-50, a-51, a-52, a-53, a-54, a-55, a-56, a-74, a-75, a-76, a-77, a-78, a-79, a-80, a-81, a-82, a-83, a-84, a-85, a-86, a-87, a-88, a-89, a-90, a-91, a-92, a-93, a-94, a-95, a-96, b-2 and c-1. As a result, all of the compounds demonstrated control values of 75% or more.

Apple scab control tests were carried out on compound nos. 1-1, 1-2, 1-4, 1-5, 1-6, 1-7, 1-8, 1-9, 1-10, 1-11, 1-12, 1-14, 1-15, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-70 and 2-2. As a result, all of the compounds demonstrated control values of 75% or more.

Biological Test Example 1-2

Apple Scab Control Test

Emulsions of compounds of the present invention were sprayed at an active ingredient concentration of 125 ppm onto apple seedlings (variety: Ralls Janet, leaf stage: 3 to 4) cultivated in unglazed pots and allowed to air-dry at room temperature. Subsequently, the seedlings were inoculated with conidiospores of apple scab pathogen (*Venturia inaequalis*) followed by holding for 2 weeks indoors at 20° C. and high humidity using a 12 hour light/dark cycle. The appearance of lesions on the leaves was compared with untreated seedlings to determine control effects.

Apple scab control tests were carried out on compound nos. a-97, a-98, a-99 and a-100. As a result, all of the compounds demonstrated control values of 75% or more.

Apple scab control tests were carried out on compound nos. 1-69, 1-71, 1-72, 1-73, 1-74, 1-75, 1-76, 1-77, 1-79 and 1-80. As a result, all of the compounds demonstrated control values of 75% or more.

Biological Test Example 2

Cucumber Gray Mold Control Test

Emulsions of compounds of the present invention were sprayed at an active ingredient concentration of 100 ppm onto cucumber seedlings (variety: *Sagami Hanjiro*, leaf stage: cotyledon) cultivated in unglazed pots and allowed to air-dry at room temperature. Subsequently, the seedlings were drip-inoculated with conidiospore suspensions of cucumber gray mold pathogen (*Botrytis cinerea*) followed by holding for 4 days in a dark room at 20° C. and high humidity. The appearance of lesions on the leaves was compared with untreated seedlings to determine control effects.

Cucumber gray mold control tests were carried out on compound nos. a-2, a-5, a-6, a-7, a-8, a-10, a-11, a-12, a-14, a-15, a-16, a-17, a-18, a-20, a-21, a-22, a-23, a-24, a-28, a-29, a-30, a-31, a-32, a-33, a-36, a-37, a-38, a-40, a-42, a-43, a-45, a-46, a-48, a-49, a-50, a-51, a-54, a-56, a-74, a-75, a-76, a-77, a-78, a-79, a-80, a-81, a-82, a-83, a-84, a-85, a-86, a-87, a-88, a-90, a-91, a-92, a-93, a-94, a-95, a-96, a-97, a-98, a-99, a-100, a-101, a-102, b-5 and c-1. As a result, all of the compounds demonstrated control values of 75% or more.

Cucumber gray mold control tests were carried out on compound nos. 1-2, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-33, 1-34, 1-35, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-79, 1-80, 1-81, 1-83, 1-84, 1-85, 2-4 and 3-4. As a result, all of the compounds demonstrated control values of 75% or more.

Biological Test Example 3

Rice Blast Submerged Application Test (2 Days)

Rice seedlings (variety: *Koshihikari*, leaf stage: 1) were cultivated in pots filled with commercially available potting soil and inundated with water, and emulsions of compounds of the present invention were dropped onto the water surface at an active ingredient concentration of 400 ppm. Two days later, seedlings were inoculated by spraying with conidiospore suspensions of rice blast pathogen (*Magnaporthe grisea*) followed by holding for 2 days in a dark room at 25° C. and high humidity. Next, the seedlings were held for 8 days indoors at 25° C. using a light/dark cycle of 12 hours. The appearance of lesions on the leaves was compared with untreated seedlings, and control effects were evaluated based on the criteria indicated below.

A: Control value of 60% or more
B: Control value of 40% to less than 60%

Rice blast soil application tests were carried out on compound nos. a-6, a-38, a-46, a-54, a-92, a-95 and b-1. As a result, the control effects of compound nos. a-6, a-38, a-46, a-54 and a-92 were evaluated as A. The control effects of compound nos. a-95 and b-1 were evaluated as B.

Rice blast submerged application tests were carried out on compound nos. 1-20, 1-24, 1-35, 1-57 and 1-68. As a result, the control effects of compound nos. 1-20, 1-35, 1-57 and 1-68 were evaluated as A. The control effects of compound no. 1-24 were evaluated as B.

Biological Test Example 4

Rice Blast Submerged Application Test (14 Days)

Rice seedlings (variety: *Koshihikari*, leaf stage: 1) were cultivated in pots filled with commercially available potting soil and inundated with water, and emulsions of compounds of the present invention were dropped onto the water surface at an active ingredient concentration of 400 ppm. 14 days later, seedlings were inoculated by spraying with conidiospore suspensions of rice blast pathogen (*Magnaporthe grisea*) followed by holding for 2 days in a dark room at 25° C. and high humidity, and then holding for 8 days indoors at 25° C. using a light/dark cycle of 12 hours. The appearance of lesions on the leaves was compared with untreated seedlings, and control effects were evaluated based on the criteria indicated below.

A: Control value of 60% or more
B: Control value of 40% to less than 60%

Rice blast submerged application tests were carried out on compound nos. a-6, a-8, a-12, a-15, a-16, a-23, a-56, a-74, a-86, a-92 and a-94. As a result, the control effects of compound nos. a-6, a-12, a-15, a-16, a-23, a-56, a-74, a-86, a-92 and a-94 were evaluated as A. The control effects of compound no. a-8 were evaluated as B.

Rice blast submerged application tests were carried out on compound nos. 1-2, 1-4, 1-5, 1-6, 1-7, 1-10, 1-11, 1-14, 1-15, 1-26, 1-27, 1-29, 1-30, 1-31, 1-35, 1-51 and 1-70. As a result, the control effects of all of the compounds were evaluated as A.

Biological Test Example 5

Cucumber Stem Rot Seed Treatment Test

Cucumber seeds (variety: *Sagami Hanjiro*) infected with cucumber seed rot pathogen (*Fusarium oxysporum*) were treated with emulsions of compounds of the present invention having an active ingredient concentration of 1 g/kg of seeds. The seeds were then sown and the degree of disease onset was compared with untreated seeds 3 weeks later to determine control effects.

Seed treatment tests on seeds infected with cucumber stem rot were carried out on compound nos. a-6, a-7, a-8, a-16, a-38, a-45, a-46, a-54, a-86, a-92 and a-95. As a result, all of the compounds demonstrated control values of 75% or more.

Seed treatment tests on seeds infected with cucumber stem rot were carried out on compound nos. 1-14, 1-15, 1-20, 1-24, 1-30, 1-35, 1-38, 1-57, 1-64, 1-68 and 1-79. As a result, all of the compounds demonstrated control values of 75% or more.

Biological Test Example 6

Cucumber Seed Treatment Test in Soil Infected with Cucumber Stem Rot

Cucumber seeds (variety: *Sagami Hanjiro*) were treated with emulsions of compounds of the present invention having an active ingredient concentration of 1 g/kg of seeds. The seeds were sown in soil infected with cucumber stem rot pathogen (*Fusarium oxysporum*), and the degree of disease onset was compared with untreated seeds 3 weeks later to determine control effects.

Seed treatment tests on soil infected with cucumber stem rot were carried out on compound nos. a-7, a-16, a-38, a-45, a-46, a-54, a-86 and a-92. As a result, all of the compounds demonstrated control values of 75% or more.

Seed treatment tests on soil infected with cucumber stem rot were carried out on compound nos. 1-4, 1-5, 1-6, 1-7, 1-14, 1-15, 1-20, 1-24, 1-30, 1-35, 1-57, 1-64 and 1-68. As a result, all of the compounds demonstrated control values of 75% or more.

INDUSTRIAL APPLICABILITY

The nitrogenated heterocyclic compound of the present invention is a novel compound that is useful as an active ingredient of an agricultural or horticultural fungicide.

The agricultural or horticultural fungicide of the present invention is a safe chemical agent that has reliable and excellent control effects, does not cause chemical damage to plants, and has little toxicity to humans, livestock or fish and has little effect on the environment.

The invention claimed is:

1. A nitrogenated heterocyclic compound represented by formula (I), or a salt thereof:

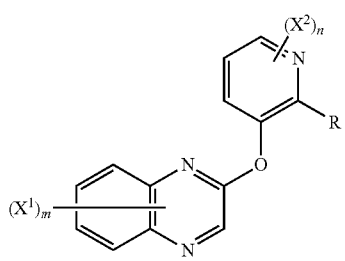

wherein,

R represents a group represented by $CR^1R^2R^3$;

$R^1$ to $R^3$ respectively and independently represent a hydrogen atom, an unsubstituted or substituted C1-8 alkyl group, an unsubstituted or substituted C2-8 alkenyl group, an unsubstituted or substituted C2-8 alkynyl group, an unsubstituted or substituted C3-8 cycloalkyl group, an unsubstituted or substituted C4-8 cycloalkenyl group, an unsubstituted or substituted C6-10 aryl group, an unsubstituted or substituted heterocyclic group, an unsubstituted or substituted C1-8 acyl group, an unsubstituted or substituted 1-imino C1-8 alkyl group, an unsubstituted or substituted carboxyl group, an unsubstituted or substituted carbamoyl group, an unsubstituted or substituted hydroxyl group, an unsubstituted or substituted amino group, an unsubstituted or substituted mercapto group, a substituted sulfonyl group, a halogeno group, a cyano group or a nitro group, provided that, $R^1$ to $R^3$ are not all hydrogen atoms, $R^1$ to $R^3$ are not all unsubstituted C1-8 alkyl groups, in a case any one of $R^1$ to $R^3$ is a hydrogen atom, the remaining two are not unsubstituted C1-8 alkyl groups, in a case any one of $R^1$ to $R^3$ is an unsubstituted C1-8 alkyl group, the remaining two are not hydrogen atoms;

$X^1$ respectively and independently represents an unsubstituted or substituted C1-8 alkyl group, an unsubstituted or substituted C2-8 alkenyl group, an unsubstituted or substituted C2-8 alkynyl group, an unsubstituted or substituted hydroxyl group, a halogeno group, a cyano group or a nitro group;

m represents a number of $X^1$ and is an integer of 0 to 5;

$X^2$ respectively and independently represents an unsubstituted or substituted C1-8 alkyl group, an unsubstituted or substituted C2-8 alkenyl group, an unsubstituted or substituted C2-8 alkynyl group, an unsubstituted or substituted C3-8 cycloalkyl group, an unsubstituted or substituted C4-8 cycloalkenyl group, an unsubstituted or substituted C6-10 aryl group, an unsubstituted or substituted heterocyclic group, an unsubstituted or substituted C1-8 acyl group, an unsubstituted or substituted 1-imino C1-8 alkyl group, an unsubstituted or substituted carboxyl group, an unsubstituted or substituted carbamoyl group, an unsubstituted or substituted hydroxyl group, an unsubstituted or substituted amino group, an unsubstituted or substituted mercapto group, a substituted sulfonyl group, a halogeno group, a cyano group or a nitro group; and n represents a number of $X^2$ and is an integer of 0 to 3.

2. An agricultural or horticultural fungicide comprising as an active ingredient thereof at least one compound selected from the group consisting of nitrogenated heterocyclic compounds or salts thereof, according to claim 1.

* * * * *